United States Patent [19]
Carpenter et al.

[11] Patent Number: 5,238,843
[45] Date of Patent: Aug. 24, 1993

[54] METHOD FOR CLEANING A SURFACE ON WHICH IS BOUND A GLYCOSIDE-CONTAINING SUBSTANCE

[75] Inventors: Richard S. Carpenter, Cincinnati, Ohio; Irwin J. Goldstein, Ann Arbor, Mich.; Pushkaraj J. Lad, San Mateo, Calif.; Ann M. Wolff, Cincinnati, Ohio

[73] Assignees: Genencor International, Inc., So. San Francisco, Calif.; The Procter & Gamble Company, Cincinnati, Ohio

[21] Appl. No.: 428,361

[22] Filed: Oct. 27, 1989

[51] Int. Cl.$^5$ .................. D06M 16/00; D06M 23/00
[52] U.S. Cl. ................................ 435/264; 435/262; 435/263
[58] Field of Search ................................ 435/262-265

[56] References Cited

U.S. PATENT DOCUMENTS

| | | | |
|---|---|---|---|
| 3,532,599 | 10/1970 | Cooperman | 435/264 |
| 4,355,022 | 10/1982 | Rabussay | 424/50 |
| 4,521,254 | 6/1985 | Anderson et al. | 134/26 |
| 4,566,985 | 1/1986 | Bruno et al. | 435/264 |
| 4,585,488 | 4/1986 | Giefer | 435/264 |
| 4,614,549 | 9/1986 | Ogunbiyi et al. | 435/264 |
| 4,619,825 | 10/1986 | Eigen et al. | 424/49 |
| 4,639,375 | 1/1987 | Tsai | 426/49 |
| 4,710,313 | 12/1987 | Miyajima et al. | 252/105 |
| 4,738,682 | 4/1988 | Boegh et al. | 435/264 |
| 4,749,511 | 6/1988 | Lad et al. | 435/264 |

(List continued on next page.)

FOREIGN PATENT DOCUMENTS

| | | |
|---|---|---|
| 0179449 | 4/1986 | European Pat. Off. . |
| 192401 | 8/1986 | European Pat. Off. . |
| 0219220 | 4/1987 | European Pat. Off. . |
| 0233721 | 8/1987 | European Pat. Off. . |
| 2937964 | 11/1982 | Fed. Rep. of Germany . |
| 8609459 | 12/1987 | France . |
| 49-048825 | 5/1974 | Japan . |
| 55-153709 | 11/1980 | Japan . |

(List continued on next page.)

OTHER PUBLICATIONS

Hughes, R. C., 1983 Glycoproteins, pp. 23–26 (Chapman & Hall, NY,NY).

Thotakura et al., 1987, "Enzymatic Deglycosylation of Glycoproteins", Methods in Enzymology, vol. 138, pp. 350–359.

Boehringer Mannheim, Biochemicals Division, Indianapolis, IN, "Glycohydrolases" Cohen, 1986, B-N14 Acetylglucosaminidase from Phycomyces Blakesleeanus, Plant Science, vol. 43, pp. 93–101.

Abeles et al., 1970, "Preparation and Purification of Glucanase and Chitinase from Beam Leaves", Plant Physiology, vol. 47, pp. 129–134.

Chaiet et al., 1970, "Isolation of a Pure Dextranase from Penicillium funiculosum", Applied Microbiology, vol. 20, No. 3, pp. 421–426.

Montague, M. D., 1964, "The Enzymic Degradation of Cell Walls of Streptococcus Faecalis", Biochim. Biophys. Acta, vol. 86, pp. 588–595.

Anderson et al., 1964, "Studies on Carbohydrate-Metabolizing Enzymes", Biochem. J., vol. 90, pp. 30–35.

Geyer et al., 1984, "Structure of the Oligosaccharides Sensitive to Endo-$\beta$-N-acetylglucosaminidase H in the Glycoprotein of Friend Murine Leukemia Virus", Eur. J. Biochem., vol. 143, pp. 531–539.

Hsieh et al., 1983, "Selective Cleavage by Endo-$\beta$-N-acetylglucosaminidase H at Individual Glycosylation Sites of Sindbis Virion Envelope Glycopro- (List continued on next page.)

*Primary Examiner*—David M. Naff
*Assistant Examiner*—Michael V. Meller
*Attorney, Agent, or Firm*—Margaret A. Horn

[57] ABSTRACT

A method for cleaning a surface on which is bound a glycoside-containing substance. The substance can be blood or components thereof, fecal matter or components thereof or microorganisms. The surface can be fabric, biological tissue, tooth enamel, contact lens, glass, ceramic, metal, metal alloy, plastic, plant, fruit and vegetable. A Type II endoglycosidase is used to carry out the method.

21 Claims, 28 Drawing Sheets

U.S. PATENT DOCUMENTS

| | | |
|---|---|---|
| 4,939,123 | 7/1990 | Neeser et al. .......................... 514/8 |
| 4,963,491 | 10/1990 | Hellgren et al. ..................... 435/264 |
| 4,994,390 | 2/1991 | Waitr .................................. 546/262 |
| 5,041,236 | 8/1991 | Carpenter et al. ............. 252/174.12 |

FOREIGN PATENT DOCUMENTS

| | | |
|---|---|---|
| 57-075926 | 5/1982 | Japan . |
| 59-088086 | 5/1984 | Japan . |
| 61-015827 | 1/1986 | Japan . |
| 62-044180 | 2/1987 | Japan . |
| 62-248487 | 10/1987 | Japan . |
| 63-002911 | 1/1988 | Japan . |
| 867738 | 4/1987 | South Africa . |
| 1272135 | 4/1972 | United Kingdom . |
| 1311375 | 3/1973 | United Kingdom . |
| 2120240 | 11/1983 | United Kingdom . |

OTHER PUBLICATIONS iteins", The Journal of Biological Chemistry, vol. 258, No. 4, issue of Feb. 25, pp. 2555-2561.

Chipman et al., 1969, "Mechanism of Lysozyme Action", Science, vol. 165, pp. 454-465.

Haskell et al., 1970, "Neuraminidase Inhibition and Viral Chemotherapy", Journal of Medicinal Chemistry, vol. 13, No. 4, pp. 697-704.

Tute, MS, 1970, "The Inhibition of Viral Neuraminidase by 1-Phenoxymethyl-3,4-dihydroisoquinolines", Part II, vol. 13, pp. 48-51.

Chang et al., 1986, "Expression and Size Heterogeneity of a 63 Kilodalton Membrane Glycoprotein During Growth and Transformation of Leishmania Mexicana Amazonensis", Molecular and Biochemical Parasitology, vol. 18, pp. 197-210.

Tarentino, A. L. and Maley, F., "Purification and Properties of an Endo-$\beta$-N-acetyl glucosaminidase from Streptomyces griseus", The Journal of Biological Chemistry vol. 249, No. 3, Issue of Feb. 10, pp. 811-817, 1974.

N-LINKED CORE STRUCTURE

Asn-GlcNAc-GlcNAc-Man
|
Z

O-LINKED CORE STRUCTURE

Ser- OR,　　-GalNAc-NeuAc
Thr-

-GalNAc-Gal

-GalNAc-Gal-NeuAc
　　　　　　　|
　　　　　　NeuNAc

-GalNAc-Gal
　　　　　　　　|
　　　　　　　　L-Fuc

Figure-1

| TYPE II ENDOGLYCOSIDASE | SUBSTRATE |
|---|---|
| Glycopeptidase-F (PNGaseF) | Asn-GlcNAc-GlcNAc-Man-v<br>↑ \|<br>(Fuc)<br>Man-W — X<br>Man-Y — Z |
| Endo-H, F, D, $C_I$ | Asn-GlcNAc-GlcNAc-Man-v<br>\| ↑<br>U<br>Man — X / W<br>Man-Y — Z |
| Endo-F-gal type | Asn-GlcNAc-Gal-Man<br>↑<br>Man-<br>Man- |
| Endo-α-N-Acetylgalactosaminidase | $\begin{bmatrix} \text{Ser} \\ \text{or} \\ \text{Thr} \end{bmatrix}$ − galNAc-Gal-<br>↑ |
| Endo-β-N-Galactosidase | ↓<br>$R_1$-GlcNAc-Gal-GlcNAc-$R_2$ |

Figure-2

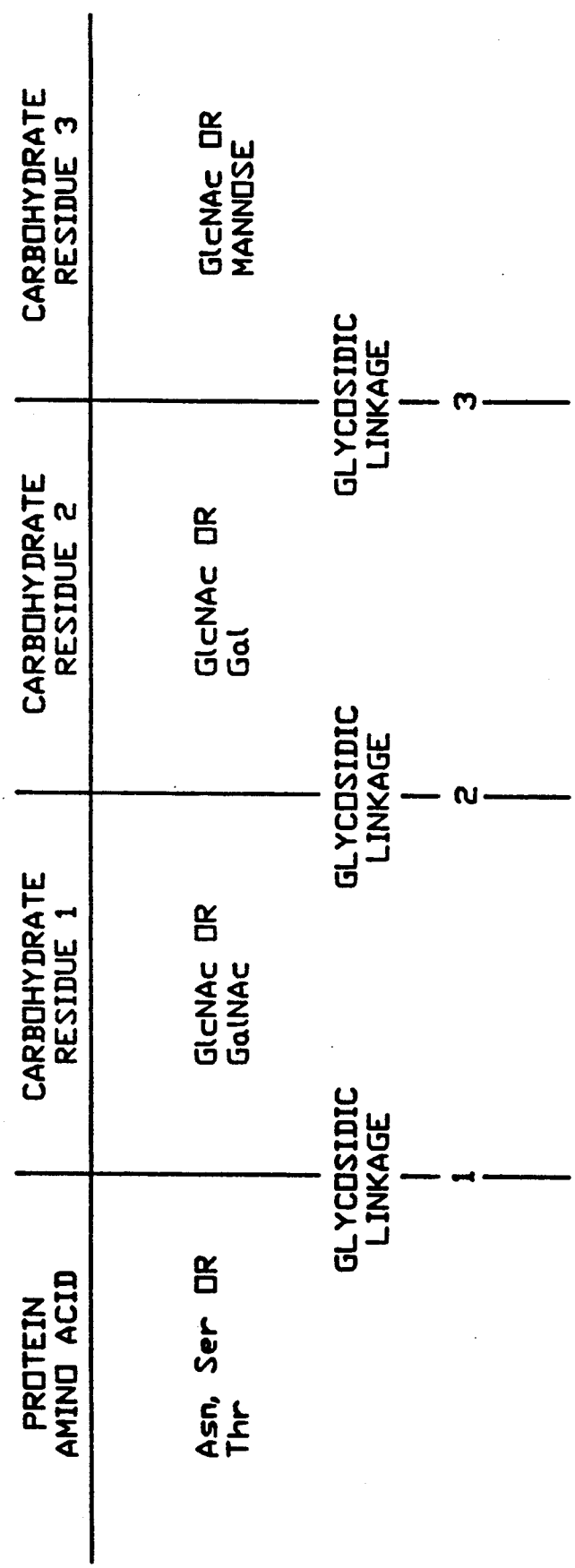
Figure—3

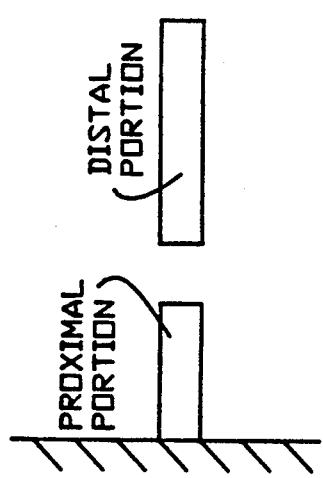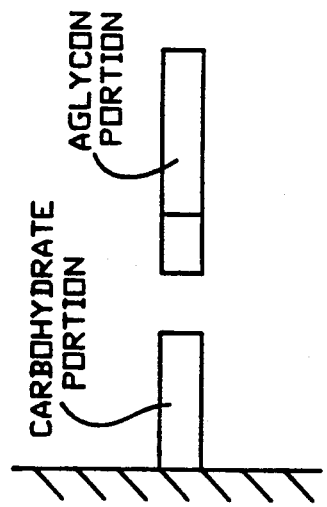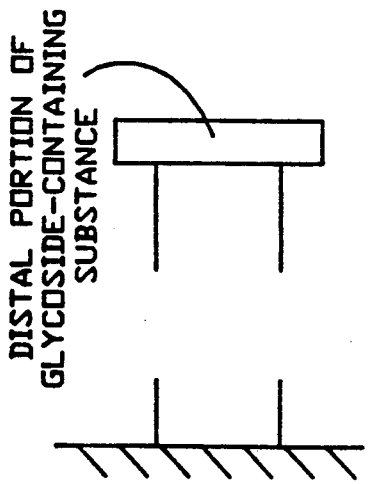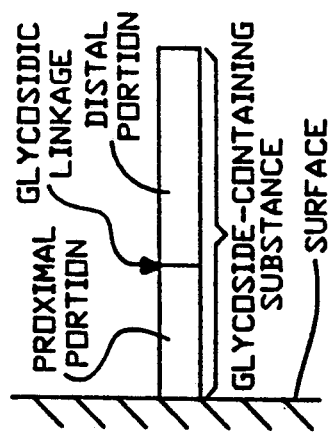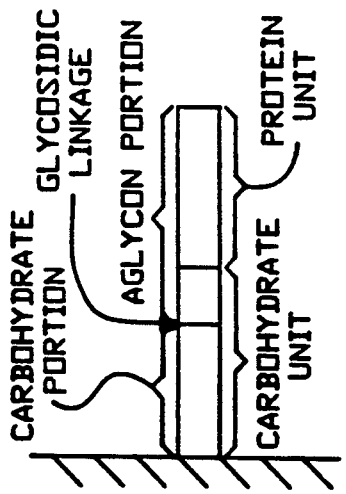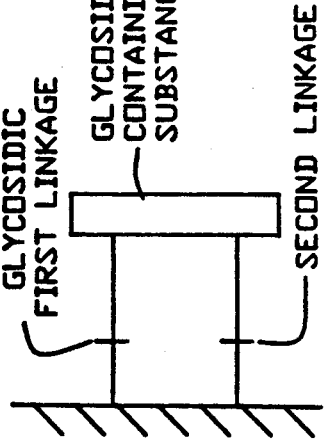
Figure-5A  Figure-5B  Figure-5C

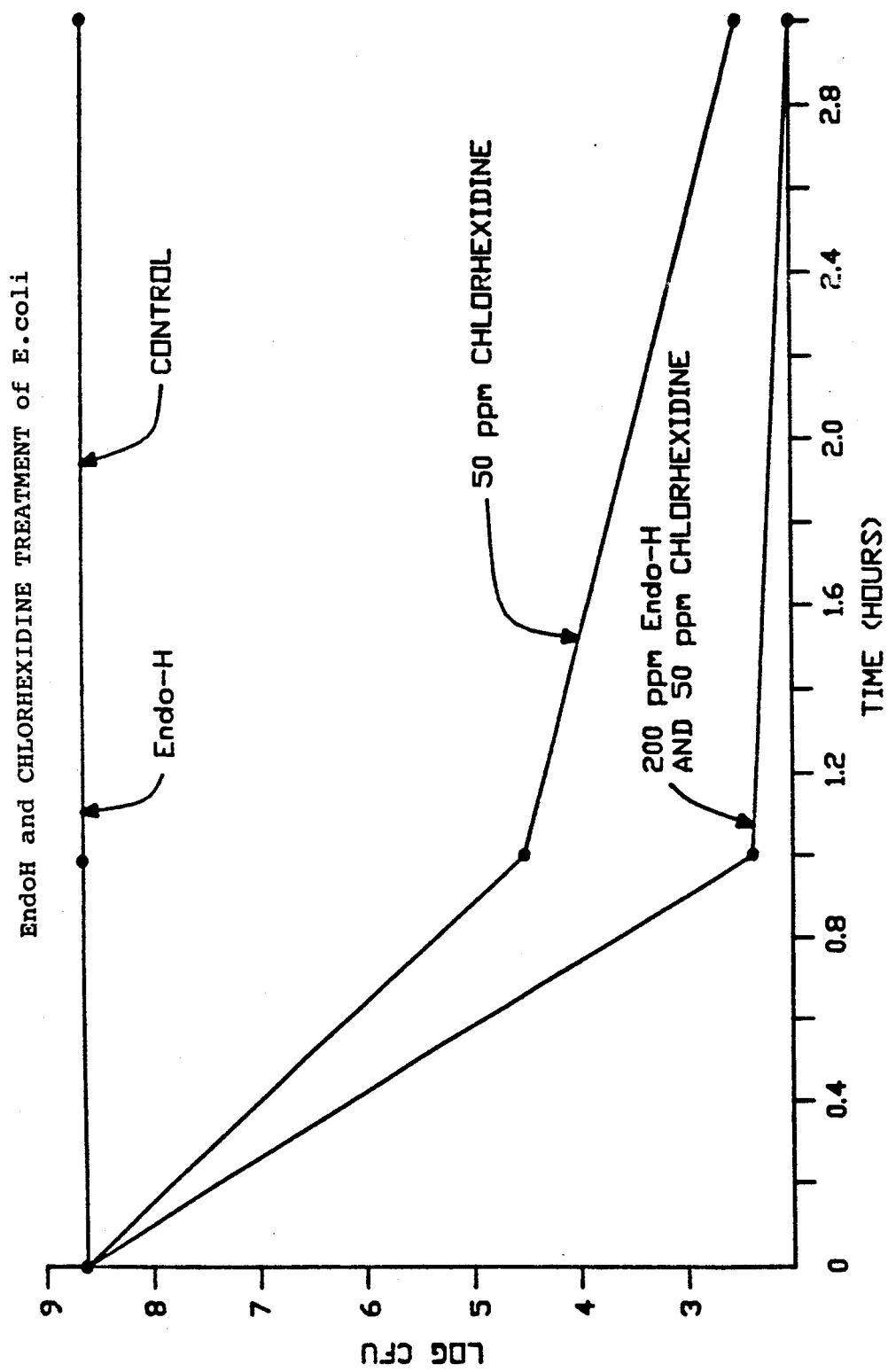
Figure—9

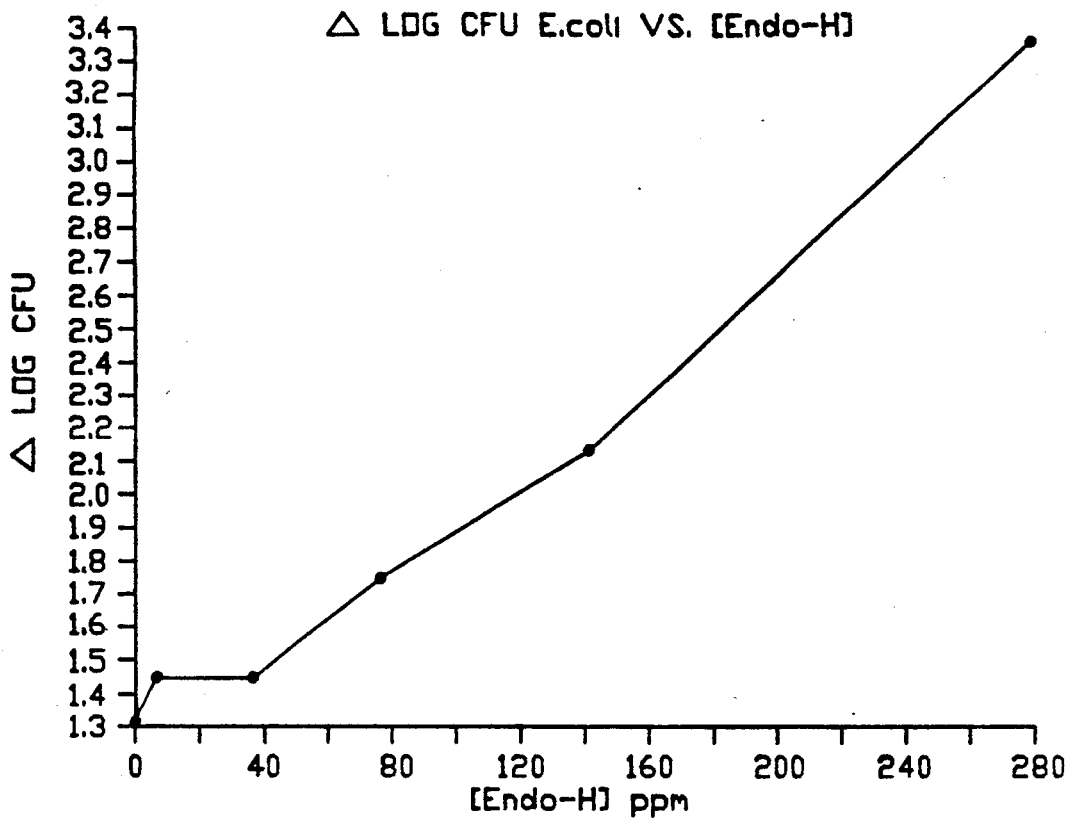
Figure—10A
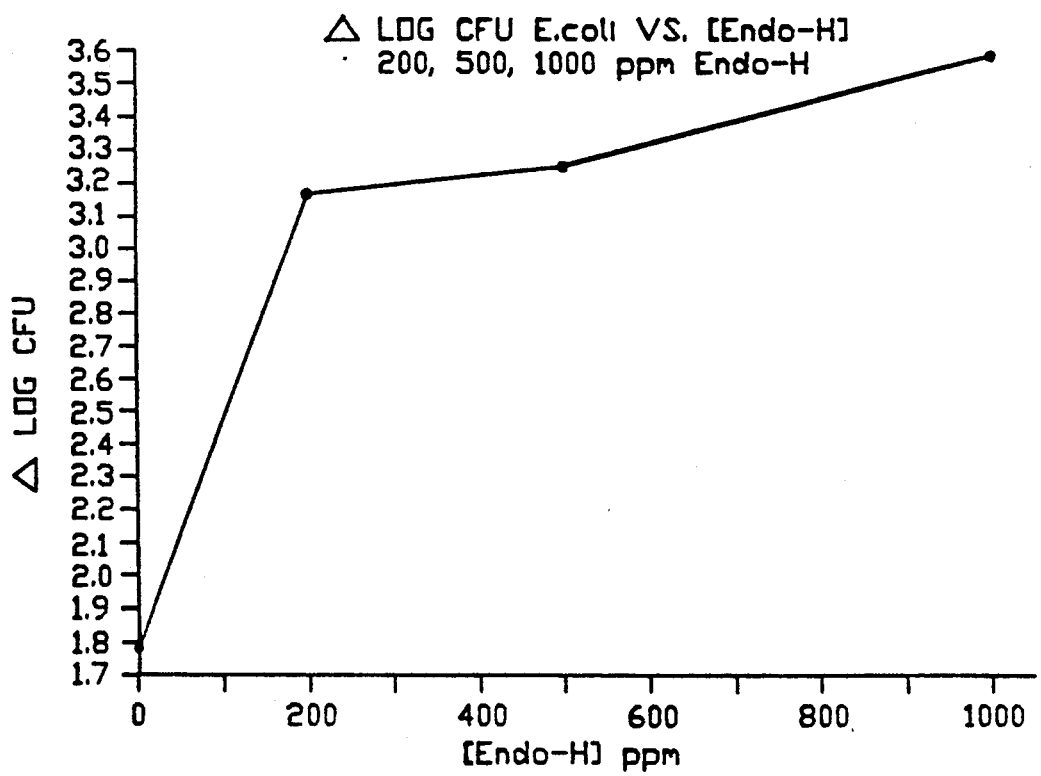
Figure—10B

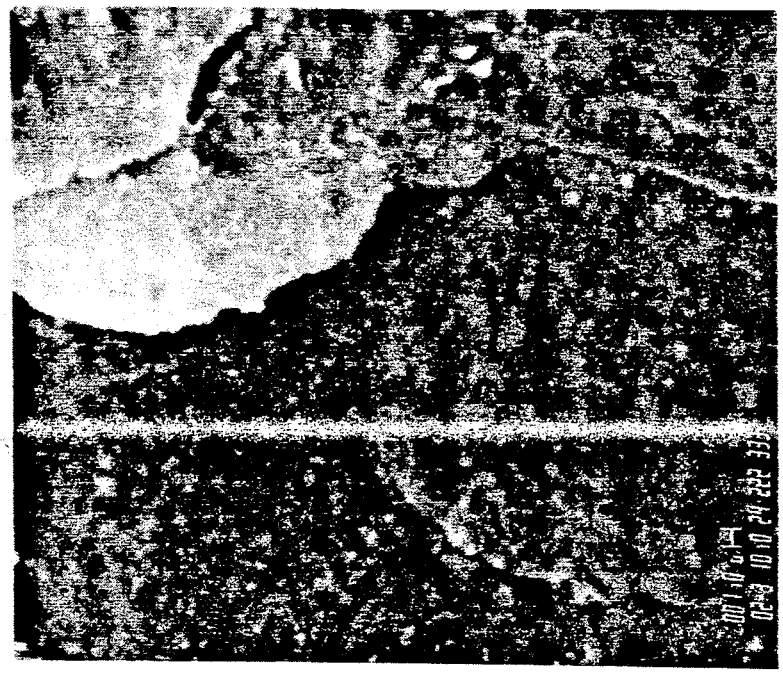
Swine skin, inoculated with *S. aureus*, treated with liquid hand soap plus Endo-H. 2000X.
Figure — 12
Swine skin, inoculated with *S. aureus*, treated with liquid hand soap. 2000X.
Figure — 11

TEM of Candida albicans, treated with buffer at pH 5.5. 5400X.

TEM of Candida albicans, treated with AWA at pH 5.5. Note leakage of material from the organisms. 5400X.

TEM of Sacchromyces cerevisiae, treated with buffer at pH 5.5. 5400X.

TEM of Sacchromyces cerevisiae, treated with AWA at pH 5.5. All that remains of the organisms are small pieces of its membranes, seen in center of micrograph. 5400X.

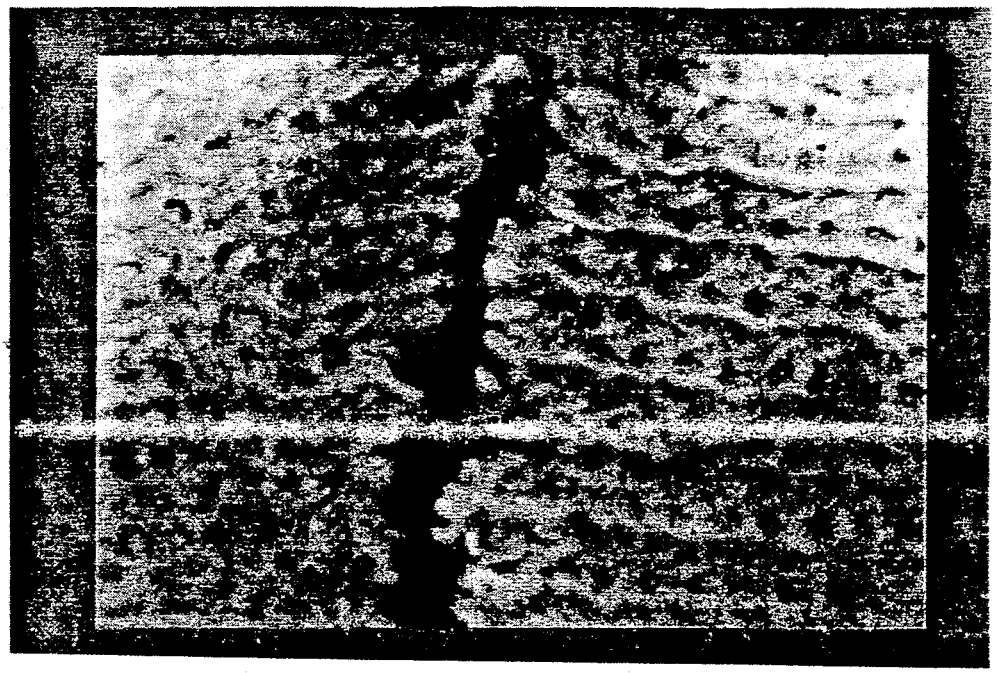
Fecal-stained fabric. Left side washed in protease detergent.
Right side washed in protease detergent plus AWA-Base. 125X.
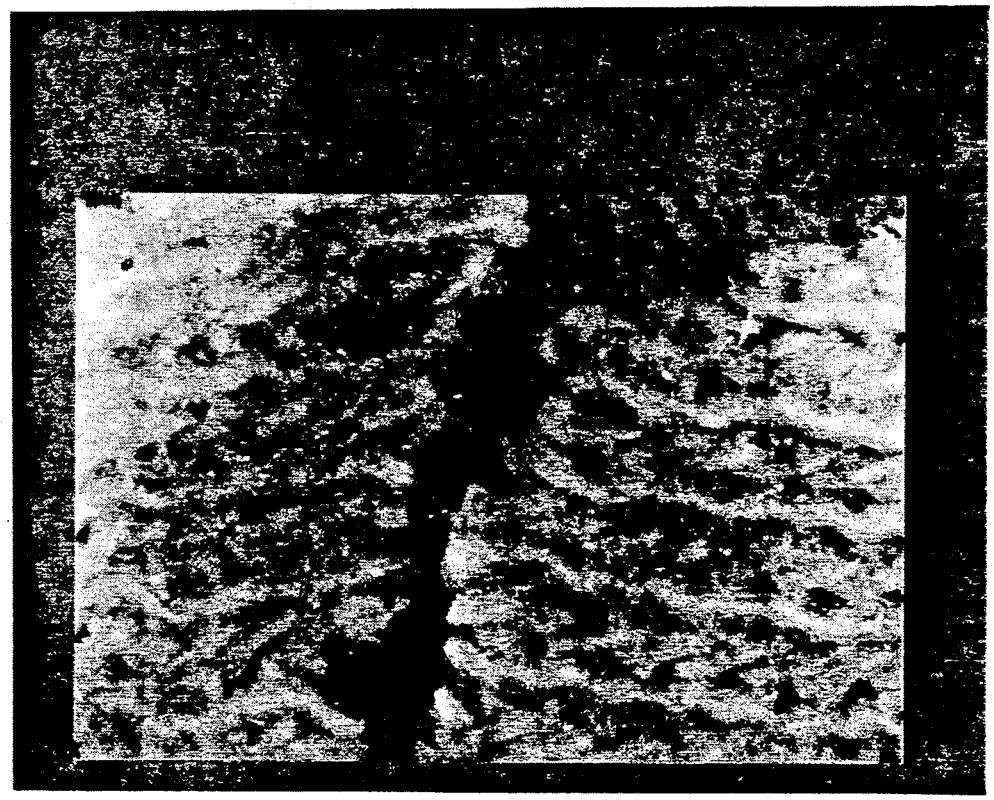
Closeup of same image. 250X.
Figure – 17

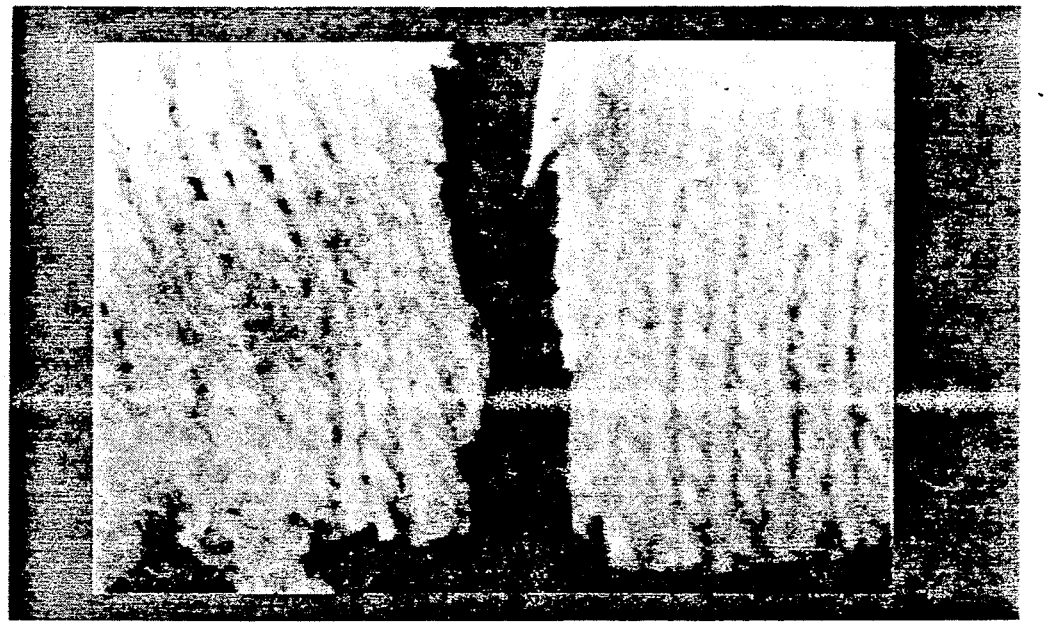
Fecal-stained fabric from another sample. Left side washed in protease detergent. Right side washed in protease detergent plus AWA-Base. 125X.
Closeup of same image. 250X.
Figure − 18

METHOD FOR CLEANING A SURFACE ON WHICH IS BOUND A GLYCOSIDE-CONTAINING SUBSTANCE

FIELD OF THE INVENTION

The present invention relates to methods and formulations for removing glycoside-containing substances, such as glycoproteins, from surfaces by treatment with Type II endoglycosidase alone or in combination with other enzymes and/or detergents.

BACKGROUND OF THE INVENTION

The use of enzymes to remove stains comprising proteins and/or carbohydrates, in combination with various detergents, is well known in the art of detergent formulations. Such enzyme formulations are designed to remove various types of stains from soft surfaces such as cloth and hard surfaces such as porcelain and metal. Thus, for example, proteases such as trypsin, pancreatin, papain and bromelain have reportedly been used in detergent formulations to remove proteinaceous stains with variable degrees of success. Specific glycosidases such as cellulase, lysozyme, amylase and glucanase, on the other hand, have been formulated with various detergents for removal of certain carbohydrate stains. Other detergent formulations have combined proteases and glycosidases for stain treatment.

Some of the glycosidases used in detergent formulations, e.g., β-amylase, α-galactosidase and β-galactosidase, are exoglycosidases which cleave one or more terminal residues from an oligosaccharide or polysaccharide. Other glycosidases, e.g. cellulase and α-amylase are endoglycosidases which are reactive with specific internal linkages within an oligo- or polysaccharide substrate. Such endoglycosidases are referred to herein as Type I endoglycosidases. Although formulations of detergent with one or more proteases and/or glycosidases (including Type I endoglycosidases) have greatly improved stain removal, many stains, e.g. blood, fecal material and body soil stains, often leave a residual stain after treatment.

In the art of contact lens cleaning, similar enzyme/detergent formulations have been used to clean and sterilize hard and soft contact lenses. In many cases, these formulations have been used to degrade the biofilm which forms on the surface of contact lenses and which is used by various ophthalmic pathogens such as *Pseudomonas aeruginosa* and *Staphylococcus epidermidis* to adhere to such lens. See, e.g., Duran, J. A., et al. (1987), *Arch. Ophthalmol*, 105 106-109; Stern, G. A., et al. (1987), *Ophthalmology*, 94, 115-119 (which reports the treatment of mucin coated contact lenses with various enzymes such as pancreatin, papain, trypsin and neuraminidase to inhibit Pseudomonas adherence); and Slucher, M. M., et al. (1987), *Arch. Ophthalmol*, 105, 110-115.

The use of biofilms for microbial adhesion is not limited to contact lenses. Thus, *Streptococcus mutans* reportedly uses extracellular polysaccharides to adhere to tooth enamel. EPO Publication No. 0195672 reports the use of α-1,3 glucanase or α-1,6 glucanase to cleave the extracellular polysaccharides used by *Streptococcus mutans* to adhere to tooth enamel.

The effect of certain enzymes on cells adhered to glass surfaces has also been reported by Danielsson, A., et al. (1977), *Botanica Marina*, 20, 13-17. As reported therein, Pseudomonas species isolated from sea water was adhered to glass slides. Thereafter, the slides were treated with either pronase, trypsin, α-amylase (a Type I endoglycosidase), or lysozyme (also a Type I endoglycosidase). In this report, treatment with the proteolytic enzymes pronase and trypsin resulted in the release of a portion of the population of adhered bacteria, whereas the cell degradative enzyme lysozyme showed diminished activity compared to the proteolytic enzymes. The α-amylase reportedly had no effect at all. In addition to the attachment of microorganisms to contact lenses, tooth enamel and glass surfaces, many other surfaces are subject to microbial attachment. See, e.g., Marrie, T. J., et al. (1984), *J. Clin. Microbiology*, 19, 991-914 (bacterial attachment to cardiac pacemaker leads and powerpacks); Freimer, N. B., et al. (1978), *Acta. Path. Microbiol. Scand. Sectb.*, 86, 53-57 (binding of microorganisms to macrophages); and Mirelman, et al. (1982), *Tokai J. Exp. Clin. Med.*, 7, 77-183 (microbial adherence to mammalian mucosal surfaces). Various mechanisms have been proposed to describe the adhesion of microorganisms, such as bacteria, to non-biological solid surfaces. See, e.g. Fletcher, M. (1987), *Microbiological Sciences*, 4, 133-136, and Duddridge, J. E., et al. (1983), *Factors Affecting the Adhesion of Bacteria to Surfaces in Microbial Corrosion*, Delco Printing Co., Ltd., pp. 28-35. Although these references discuss microbial adherence to various surfaces and the factors which may be involved in such attachment, they do not discuss the control of microorganism growth on such surfaces or their removal therefrom.

Type II endoglycosidases, as used herein, are a category of endoglycosidases which are capable of cleaving specific internal glycosidic linkages found in glycoproteins. These endoglycosidases cleave all or part of the carbohydrate moiety from a glycoprotein depending on the location of the reactive glycosidic linkage in the glycoprotein. Examples include endo-β-N-acetylglucosaminidases (Endo-D, Endo-H, Endo-L, Endo-CI, Endo-CII, Endo-F-Gal type and Endo-F), endo-α-N-acetylgalactosaminidase and endo-β-N-galactosidases. See, e.g. Tarentino, A. L., et al. (1985), *Biochem*, 24, 4665-4671; Arakawa, M., et al. (1974), *J. Biochem.*, 76, 307-317; Plummer, T. H., et al. (1984), *J. Biochem*, 259, 10700-10704; Tarentino, A. L., et al. (1975), *Biochem. and Biophys. Res. Comm.*, 67, 455-462; and Trimble, R. B., et al. (1984), *Anal. Biochem.*, 141, 515-522; and "Glycoprotein and Proteoglycan Techniques" (1985) by J. G. Beeley, Chapter 6, pp. 153-300, Elsevier, Amsterdam, New York, Oxford. In addition to having a specificity for the internal glycosidic linkages of glycoproteins, at least one endoglycosidase (endo-β-N-acetylglucosaminidase H) has also demonstrated a specificity which produces the cleavage of lipid-linked oligosaccharides (Chalifour, R. J., et al. (1983), *Archives of Biochem. and Biophys.*, 29, 386-394) and reportedly di-N-acetylchitobiose linkages in oligosaccharides and glycoproteins (Tarention, A. L., et al. (1974), *J. Biol. Chem.*, 249, 811-817).

Such Type II endoglycosidases, in general, have been used primarily for analytical purposes, e.g. the determination of protein or carbohydrate sequence and/or the structure and function of specific glycoproteins. See, e.g. Hsieh, P., et al. (1982), *J. Biolchem.*, 258, 2555-2561, and Geyar, R., et al. (1984), *Eur. J. Biochem.*, 143, 531-539. In a recent report, a Type II endoglycosidase was reportedly used to analyze a glycoprotein antigen from *Leishmania mexicana amazonensis*. Chin Shen Chang, et al. (1986), *Mol. Biochem. Parasitol* 18, 197-210. This glycoprotein antigen was first immunologically bound to immunobeads. After reacting the immunologically bound glycoprotein with analytical amounts of Endo-H, the immunobeads were washed and boiled in buffer containing 1% SDS in preparation for polyacrylamide gel electrophoresis. This analysis revealed a decrease in molecular weight attributed to the cleavage of carbohydrate from the immunologically bound glycoprotein antigen.

Type II endoglycosidases, however, have not been used to remove substances, including glycoproteins and glycolipids, from surfaces of substances such as fabric, contact lenses, metals, ceramics, cells, tissue and the like. Nor have they been used to control microorganism growth in suspension or on such surfaces.

Glycosidases have been used in combination with other enzymes for removal of various materials. $\beta$-glycosidases are described as carbohydrate-metabolizing enzymes in Anderson, et al. (1964), *Biochem. J.*, 90, 30. Neuraminidase (N-acetylneuraminiate glycohydrolase) inhibitors are viewed as possible anti-viral, antibacterial agents in Khorlin, et al. (1979), *FEBS Letters*, 8, 17; and Haskell, et al. (1970), *J. Med. Chem.*, 13, 48. Dextranase is described as catalyzing hydrolysis of bacterial polysaccharide, dextran ($\alpha$-1,6-glucan), to isomaltose residues in Chaiet, et al. (1970), *Appl. Microbiol.*, 20, 421. Lysozyme (muramidase) is described as hydrolyzing glycosidic linkages in the mucopolysaccharide cell wall structure of a variety of microbes in Chipman, et al. (1969), *Science*, 165, 454 and Montague (1964), *Biochem. Biophys. Acta.*, 86, 588. Lastly, inhibition of lysozyme by D-glucosamine derivatives is described in Neuberger, et al. (1967), *Nature*, 215, 524.

Type II endoglycosidases such as endo-$\beta$-N-acetylglucosaminidase H, D, F and/or PNGase F have not, however, previously been combined with antimicrobial agents to form antimicrobial compositions.

The references discussed above are provided solely for their disclosure prior to the filing date of the instant case, and nothing herein is to be construed as an admission that such references are prior art or that the inventors are not entitled to antedate such disclosure by virtue of prior invention or priority based on earlier filed applications.

SUMMARY OF THE INVENTION

It is an object herein to provide methods utilizing Type II endoglycosidases alone or in combination with other enzymes, detergents, surfactants and/or disulfide cleaving reagents to facilitate the removal of substances including glycoproteins and glycolipids from materials such as fabric, contact lenses, metallic surfaces, plastic surfaces, ceramic surfaces, cell surfaces, tissue and the like.

It is a further object herein to provide formulations containing Type II endoglycosidases useful in practicing such methods.

In accordance with the objects of the invention, methods are provided for removing at least a portion of a substance from a surface to which it is bound, other than by an immunological bond. The substance has a proximal portion bound to a surface, a distal portion extending outwardly from the proximal portion, and a linkage disposed at the juncture of the proximal and distal portions which is reactive with a Type II endoglycosidase. The method comprises contacting the bound substance with a Type II endoglycosidase to cleave the distal portion of the substance from the proximal portion thereby releasing the distal portion from the surface. If such releasing does not remove the distal portion from the surface, such removal may be facilitated by contacting the distal portion with a washing solution, a detergent formulation including those with surfactants or a fluid containing a second enzyme such as a different glycosidase, protease, lipase, nuclease or combinations thereof.

The invention further includes a method for releasing at least a portion of a glycoside-containing substance from a surface to which it is bound by contacting the glycoside-containing substance with at least a first and a second enzyme to release a cleaved portion of the glycoside-containing substance from the surface. The first enzyme is a Type II endoglycosidase reactive with a glycosidic linkage in the glycoside portion of the substance. The second enzyme is reactive with a second linkage in the glycoside-containing substance other than the glycosidic linkage with which the first enzyme is reactive. Such second enzymes may include glycosidases (including a second Type II endoglycosidase), proteases, lipases and combinations thereof. The removal of a portion of the glycoside-containing substance may be facilitated by contacting the cleaved glycoside-containing substance with a detergent including those containing a surfactant.

The invention also includes a method for releasing from a surface at least a portion of a glycoside-containing substance having a carbohydrate portion, an aglycon portion and a glycosidic linkage at the juncture of the carbohydrate and aglycon portions wherein the glycoside containing substance is bound to a surface through the carbohydrate portion. The method comprises cleaving the glycosidic linkage with a Type II endoglycosidase to release the aglycon portion of the glycoside-containing substance from the surface. Removal of the cleaved portion of the glycoside-containing substance may, if necessary, be facilitated by treatment with a second enzyme, detergent and/or surfactant.

In each of the above methods, a disulfide cleaving reagent may be employed to denature protein associated with the glycoside-containing substance thereby facilitating cleavage by the Type II endoglycoside or second enzyme or removal by detergent and/or surfactant.

The invention also includes formulations. One composition comprises at least a first and a second enzyme wherein the first enzyme is a Type II endoglycosidase. The second enzyme is selected from the group of enzymes consisting of proteases, glycosidases, lipases and combinations thereof. Such formulations may also include detergents and/or surfactants as well as disulfide cleaving reagents.

Another composition includes Type II endoglycosidase and detergent and/or surfactant.

BRIEF DESCRIPTION OF THE DRAWINGS

FIG. 1 depicts the common core structure of N-linked and O-linked glycoproteins.

FIG. 2 depicts the substrates and known cleavage sites for various Type II endoglycosidases.

FIG. 3 is a generic presentation of the protein amino acids, carbohydrate residues and cleavage sites of FIG. 2.

FIGS. 5A-5E depict various mechanisms whereby a glycoside-containing substance, microorganisms or substances reactive with Type II endoglycosidase may be released from a surface by treatment with Type II endoglycosidase alone or in combination with a second enzyme.

FIGS. 8, 9 10A and 10B demonstrate the effect of various concentrations of Endo-H and chlorhexidine, alone or in combination, on the viability of E. coli.

FIGS. 11 and 12 demonstrate that a detergent composition containing Endo-H is more effective in the removal of S. aureaus from swine skin than a detergent composition not containing Endo-H.

FIGS. 17 and 18 demonstrate the enhanced removal of fecal matter from diaper material by a detergent composition containing Endo-H.

DETAILED DESCRIPTION OF THE INVENTION

Figure 4:
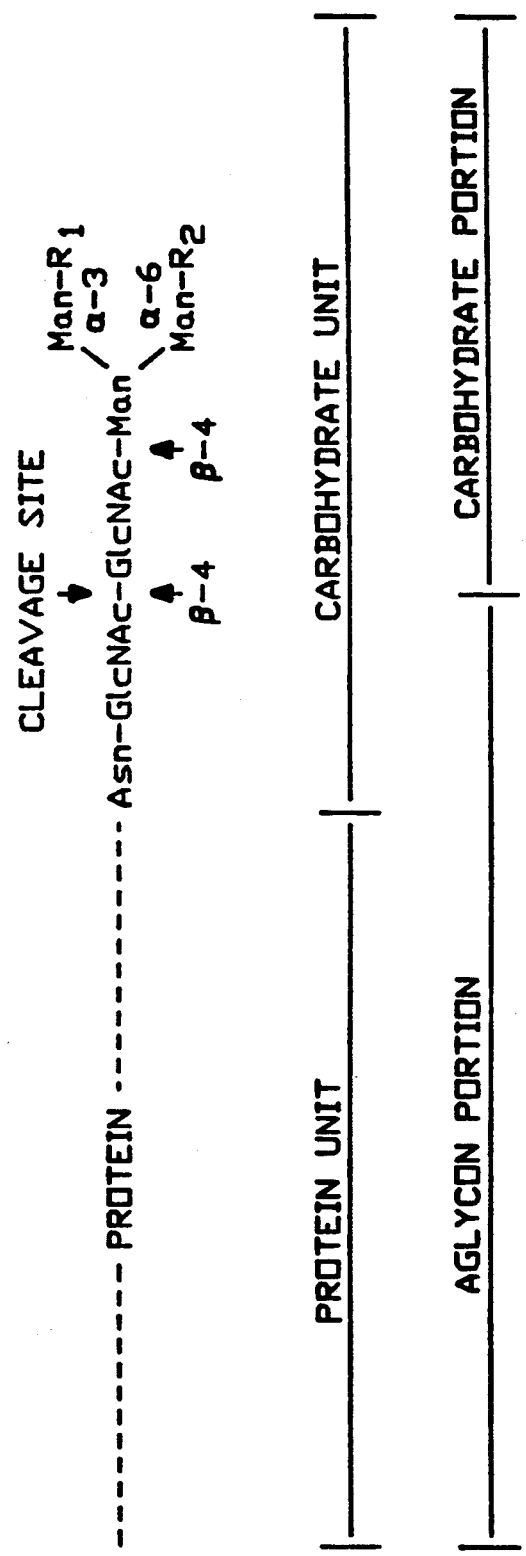
FIG. 4 depicts the core structure of an N-linked glycoprotein, the cleavage site of a Type II endoglycosidase and the relationship between the protein and carbohydrate units and the aglycon and carbohydrate portions produced upon cleavage with a Type II endoglycosidase.

Type II endoglycosidases and formulations employing such endoglycosidases are used in the methods of the present invention to release and/or remove substances reactive with Type II endoglycosidases from a surface. The mechanism of this reactivity is not known with certainty. In some cases, such substances are glycosides or glycoside-containing substances which are believed to have glycosidic linkages that are known cleavage sites for Type II endoglycosidases or linkages which are closely related to such cleavage sites.

As used herein, "Type II endoglycosidases" are enzymes which are capable of cleaving linkages at or near the juncture of the protein and carbohydrate units of a glycoprotein. Preferably, such Type II endoglycosidases are capable of cleaving at least one glycosidic linkage within about three glycosidic linkages of the protein-carbohydrate unit juncture (including the glycosidic linkage comprising the protein-carbohydrate junction). Most preferably, such glycosidic linkages are within about two glycosidic linkages of the protein-carbohydrate unit juncture (see FIGS. 1, 2 and 3).

Type II endoglycosidases are also defined by their specificities for the particular glycosidic linkages shown in FIG. 1 for the known core structures of N-and O- linked glycoproteins. These correspond to the glycosidic linkages between the amino acids serine, threonine or asparagine and the first carbohydrate residue and the glycosidic linkages between at least the first, second and third carbohydrate residues. Although this core structure will be described in more detail hereinafter in terms of the specific glycosidic linkages which exist in known core structures, such specific linkages are not to be construed as limiting to this definition of Type II endoglycosidases. Accordingly, all possible glycosidic linkages between these amino acids and carbohydrate residues define the core structure of N-and O- linked glycoprotein used to identify Type II endoglycosidases.

Type II endoglycosidases are not limited by the present knowledge of the glycoprotein core structure and the specificity of known endoglycosidases for such core structures. A comparison of the core structures in FIG. 1 with the known substrates for Type II endoglycosidases in FIG. 2 indicates that Type II endoglycosidases for each of the possible cleavage sites in the core structures in FIG. 1, if they exist, have not yet been identified. Moreover, other core structures may also exist which have not yet been identified. Endoglycosidases reactive with linkages in such, as yet, unknown core structures are also Type II endoglycosidases. Accordingly, the glycosidic linkages in glycoproteins which define Type II endoglycosidases are not limited to those located within the first three glycosidic linkages closest to the protein unit of the glycoprotein but may extend to more distant glycosidic linkages in the core structure, e.g. to the fourth or fifth glycosidic linkage from the protein unit depending on the core structure identified.

The specificity for the core structure of glycoproteins provides a convenient definition of Type II endoglycosidases which distinguishes them from Type I endoglycosidases. Type I endoglycosidases cleave specific linkages in oligo- or polysaccharides but generally are not reactive with those core structure glycosidic linkages in glycoproteins which define Type II endoglycosidases. Examples of Type I endoglycosidases and the linkages with which they are reactive are shown in Table I.

TABLE I

| Type I Endoglycosidase | Substrate oligo-or polysaccharide |
|---|---|
| α-amylase | α1–4 <br> (Glc—Glc)$_n$ <br> ↑ |
| cellulase | β1–4 <br> (Glc—Glc)$_n$ <br> ↑ |
| hyaluronidase | β1–3   β1–4   β1–3 <br> GlcA—GlcNAc—GlcA—GlcNAc <br> *         ↑ |
| lysozymes: <br> hen egg white lysozyme <br> T4 lysozyme <br> mutanolysin | β1–4   β1–4   β1–4 <br> GlcNAc—MurNAc—GlcNAc—MurNAc <br> ↑         * |
| pullulanase | α1–4  α1–4  α1–6  α1–4 <br> Glc—(Glc—Glc—)Glc—Glc <br> ↑ |

*GlcA is D-Glucuronic Acid
*MurNAc is N-Acetylmuramic Acid
† Indicates cleavage site.

Specific glycosidic linkages in glycoproteins which define Type II endoglycosidases and which identify preferred Type II endoglycosidases are shown in FIG. 2. The cleavage sites are identified by a vertical arrow.

A generic presentation of the protein amino acids, carbohydrate residues and cleavage sites of FIG. 2 is shown in FIG. 3. As can be seen, Type II endoglycosidases preferably cleave the first, second or third glycosidic linkages in N- or O-linked glycoproteins. These linkages comprise the glycosidic linkages (1) between asparagine, serine or threonine in the protein unit and the first carbohydrate residue, (2) between carbohydrate residues 1 and 2 and (3) between carbohydrate residues 2 and 3, respectively. This specificity is defined primarily by the carbohydrate sequence of the glycoprotein with specificity and reactivity being influenced to some extent by the protein unit of the glycoprotein. Thus, with regard to glycosidic linkages 2 and 3 (comprising glycosidic linkages between carbohydrate residues only), Type II endoglycosidases may be reactive with identical or similar glycosidic linkages located in other regions of a glycoprotein, perhaps quite distant from the juncture of the protein and carbohydrate units of the glycoprotein.

An application of the above definition to a particular glycoprotein is illustrative. Bovine thyroglobulin has been analyzed using endo-$\beta$-N-acetylglucosaminidase-H (Endo-H), $\alpha$-mannosidase and $\beta$-mannosidase. Tarentino, A. L. et al. (1973) *J. Biol. Chem.*, 218, 5547. The Endo-H hydrolyzed the glycosidic linkage between the two N-acetyl D-glucosamines, one of which was N-linked to an asparagine in the protein unit of the thyroglobulin. The oligosaccharide or carbohydrate portion of the thyroglobulin released upon treatment with Endo-H was also treated with $\alpha$- and $\beta$-mannosidase. Since neither of these enzymes has a specificity for the substrates corresponding to those shown in FIGS. 1, 2 or 3, they are not Type II endoglycosidases and can be characterized as either an exoglycosidase or Type I endoglycosidase. The specificity of the Endo-H is the same as that shown for Endo-H in FIG. 2 and Endo-H is therefore a Type II endoglycosidase. This is of course a trivial application. But if a new endoglycosidase (e.g. Endo-X) is discovered which also demonstrates this specificity or one or more of the other specificities in FIGS. 1, 2 or 3, that Endo-X would also be a Type II endoglycosidase.

This definition of a Type II endoglycosidase based on its specificity for glycoproteins, however, should not be construed as a limitation on the mechanism utilized by Type II endoglycosidases to release and/or remove a substance from a surface. Although it will be assumed in some instances that Type II endoglycosidases cleave at least a part of a glycoside from a surface by reacting with a glycosidic linkage in the glycoside, the invention is not limited to such cleavage. Rather, the action of Type II endoglycosidases is defined functionally by their ability to cleave from a surface at least a part of any substance reactive with a Type II endoglycosidase.

As used herein, the term "endoglycosidase" comprises Type I and Type II endoglycosidases.

As used herein, "glycoside" refers to a polymer which has one or more "carbohydrate portions" covalently attached through a glycosidic linkage to an "aglycon portion". This definition of glycoside is derived from the common definition of glycoside which refers to a compound that yields on hydrolysis a sugar and an aglycon, the aglycon being the non-sugar compound resulting from such hydrolysis. As used herein, a glycoside produces an aglycon and an oligo- or polysaccharide carbohydrate portion when cleaved by a Type II endoglycosidase. The aglycon unit, however, is not limited to a non-sugar compound since Type II endoglycosidases may hydrolyze a glycoside to produce an aglycon portion containing one or more sugar residues depending on the cleavage site of the Type II endoglycosidase. Further, the aglycon portion may be quite complex as might be the case with peptidoglycans where crosslinked peptides can be found attached to a matrix of carbohydrate. Thus, glycosides include glycoproteins, glycolipids, peptidoglycans and the like which upon treatment with a Type II endoglycosidase produce a carbohydrate portion and aglycon portion wherein the carbohydrate portion and aglycon portion are defined by the cleavage site of the Type II endoglycosidase. This definition of glycoside will be apparent from the discussion which follows.

As used herein, "glycoprotein" refers to a glycoside which has one or more oligo- or polysaccharides covalently attached to a peptide or protein. Oligo-and polysaccharides are sometimes referred to herein as "carbohydrate units". Such carbohydrate units, however, may be different from the "carbohydrate portion" of a glycoside. As shown in FIG. 4, a carbohydrate unit comprises the entire oligo- or polysaccharide attached to a second class of molecule, e.g., to a protein or peptide as in a glycoprotein or to a lipid as in a glycolipid. If the Type II endoglycosidase cleaves the carbohydrate unit at its juncture with, for example, a protein then the carbohydrate unit is synonymous with the carbohydrate portion of a glycoside. If, however, the Type II endoglycosidase cleaves the carbohydrate unit at a glycosidic linkage within the carbohydrate unit, then the carbohydrate portion of the glycoside formed by such cleavage will be less than the entire carbohydrate unit. This difference is shown in FIG. 4 for a Type II endoglycosidase cleavage site indicated by the arrow.

The carbohydrate units of a glycoprotein may be oligosaccharides containing 1 to 10 carbohydrate (sugar) residues or short polysaccharides which usually contain between 10 to 25 carbohydrate residues. Many glycoproteins are produced by higher organisms such as eukaryotes including yeast and mammalian cells. The linkage between the carbohydrate unit and the peptide or protein unit of a glycoprotein is a glycosidic linkage which results from a condensation reaction between an amino acid side chain of the protein unit and the anomeric carbon on the first residue of the carbohydrate unit. Such glycosidic linkages in mammalian glycoproteins are either N-glycosidic linkages (carbohydrate linked to the amido nitrogen of asparagine) or O-glycosidic linkages (carbohydrate linked to the hydroxy oxygen of serine or threonine).

The carbohydrate residues (monosaccharides) of a carbohydrate unit (oligo or polysaccharide) may be joined together in many different ways. Thus, such carbohydrate units may be unbranched, linear structures or may be complex branched structures. In general, however, each of the carbohydrate residues in the carbohydrate unit is linked by way of a glycosidic linkage wherein the anomeric carbon of one carbohydrate residue is condensed with the hydroxyl carbon in another carbohydrate residue. Such glycosidic bonds may be either alpha or beta depending on the configuration of the anomeric carbon. The anomeric carbon of one residue may be combined with any of the hydroxyl carbons in another carbohydrate residue. Thus, the complexity of many glycoproteins arises from the many different glycosidic linkages which are found in the carbohydrate units of such molecules.

Many membrane glycoproteins carry asparagine-linked carbohydrate units (carbohydrate units linked to asparagine in a peptide via an N-glycosidic linkage). The structure of such asparagine linked glycoproteins can be quite complex. See e.g., Schachterh (1984) *Clinical Biochemistry* 17, 3–14. The structure of many of these asparagine linked membranous glycoproteins from a variety of sources (e.g., erythrocyte plasma membrane glycoproteins, viral envelope glycoproteins) as well as the structure of non-membranous soluble glycoproteins indicate that the two types of glycoproteins share many structural features. Id. at 3. The common core structure of such asparagine-linked glycoproteins is shown in FIGS. 1 and 4, wherein GlcNAC is N-acetyl D-glucosamine and Man is mannose. The $\alpha$1-6, $\alpha$1-3 and $\beta$1-4 designations describe the type of glycosidic linkage between the various carbohydrate residues. This core linkage forms the basis of numerous glycoproteins having any of a number of carbohydrate residues attached to the core. Id. at 5.

O-linked glycoproteins contain a core structure wherein the protein unit of the glycoprotein is coupled to the carbohydrate unit through the hydroxyl group of either serine or threonine. A common feature of this core structure is the presence of N-acetyl D-galactosamine (GalNAc) linked to serine or threonine. Other details of such glycoproteins are shown in FIG. 1 where NeuAc is N-acetylneuraminic acid, Gal is Galactose and L-Fuc is L-Fucose. When Gal is the second carbohydrate residue the glycosidic linkage between GalNAc and Gal is usually $\beta$1-3. For review of the structure biosynthesis and function of glycoproteins including N-and O- linked glycoprotein, see Berger E. G. et al. (1982) *Experimentia*, 38, 1229–1258.

Lower organisms such as prokaryotes, e.g., the bacteria *E. coli*, Pseudomonas species, Bacillis species and the like, produce peptidoglycans rather than glycoproteins. Peptidoglycans are found in bacterial cell walls and typically have a polysaccharide backbone of alternating N-acetyl-glucosamine and N-acetylmuramic acids. Peptide side chains are sometimes associated with the N-acetyl-muramic acid residues with cross-linked peptide bridges often being interposed between the peptide side chains. The cell wall of Gram-positive bacteria typically comprises approximately 10% peptidoglycan whereas the cell wall of Gram-negative bacteria typically have a peptidoglycan content of about 50%.

Peptidoglycans, however, are not glycoproteins, at least to the extent that specific glycosidic linkages in glycoproteins are used to define the class of Type II endoglycosidase. Thus, Endo-H is a Type II endoglycosidase because it cleaves the glycosidic linkage between the two N-acetylglucosamine sugar residues found in some glycoproteins containing N-linked oligosaccharides. See FIG. 4. Endo-H, however, may also have an as yet undefined reactivity with peptidoglycan since it is capable of facilitating the removal of fecal matter from a surface such as cloth swatches. Such fecal matter is known to contain peptidoglycans associated with intestinal bacteria. Lysozymes are enzymes which are reactive with peptidoglycan. Lysozymes, such as hen egg white lysozyme, T4 lysozyme and mutanolysin (Goodman, et al. (1981), *J. Bacteriol*, 146, 755), however, are not Type II endoglycosidases. This is because they do not have a substantial reactivity with the unique glycosidic linkages found in N- and O-linked glycoproteins used to define Type II endoglycosidases. They are, however, reactive with peptidoglycans to produce disaccharides of N-acetylglucosamine and N-acetylmuramic acid containing attached peptide side-chains. As such, lysozymes are more appropriately characterized as a Type I endoglycosidase. Thus, even though lysozymes and Endo-H may have an overlap in reactivity with peptidoglycans, they are mutually exclusive, for the most part, with regard to Endo-H's specificity for, and lysozyme's substantial lack of reactivity with, the glycosidic linkages in glycoproteins which define Type II endoglycosidases.

As used herein, a "glycoside containing substance" or "glycoprotein containing substance" is a glycoside or glycoprotein alone or a glycoside or glycoprotein combined with another component. Thus, glycoside-containing substances include glycosides such as glycoprotein enzymes, e.g., alkaline phosphatase, bromelain, carboxypeptidase-Y; glycoprotein hormones, e.g., chorionic gonadotropin, erythropoietin; lectins, e.g., those derived from potato and soybean; serum glycoproteins, e.g., IgG immunoglobulin, thyroglobulin, prothrombin and the like and miscellaneous glycoproteins such as hemoglobin and interferon; and complex carbohydrates. Examples of glycosides combined with another component include glycoproteins comprising membrane constituents, e.g., glycophorin contained by human erythrocytes, hemagglutinin contained by influenza virus, rhodopsin contained in bovine retina and collagen contained by fibroblasts. Further glycoside-containing substances include viral envelope glycoproteins and fecal matter which contains in part peptidoglycans associated with intestinal bacteria. Thus, viruses, fibroblasts, fecal matter etc. are considered glycoside-containing substances.

As used herein, a "microorganism" (sometimes referred to as a glycoside-containing microorganism) is one capable of being cleaved from the surface of a substance to which it is bound by a Type II endoglycosidase. Examples include the intestinal bacteria found in fecal matter and bacteria commonly contaminating contact lens. Other examples include fungi and algae which can be cleaved from a surface by Type II endoglycosidase.

As used herein, the term "in vitro" refers to the environment in which the processes and methods of the invention are practiced. It is used only to distinguish from the term "in vivo" which describes the environment in which Type II endoglycosidases are found naturally, e.g. within organisms which naturally produce Type II endoglycosidase. Accordingly, an in vitro method employing a Type II endoglycosidase is a method or process which does not occur in nature. The term in vitro, however, is not to be construed as a limitation of such methods to "in glass" or to exclude such methods from being practiced on or in a living organism. The methods of the invention may be practiced on a variety of surfaces other than glass including fabric, contact lenses, metallic surfaces, ceramic surfaces, cell surfaces, plastic surfaces, tissue and the like. Further, such in vitro methods may be practiced for example in the human oral cavity as described in more detail hereinafter.

Some known Type II endoglycosidases are listed in Table II together with the natural biological source of such enzymes. The cleavage sites for some Type II endoglycosidases are shown in FIG. 2. See "Glycoprotein and Proteoglycan Techniques" (1985) by J. G. Beeley, Chapter 6, pp. 153–300, Elsevier, Amsterdam, New York, Oxford. A Type II endoglycosidase not listed in Table II is Glycopeptidase F also sometimes referred to as PNGase F. PNGase F may be obtained from *Flavobacterium meningosepticum*. It is also commercially available from Boehringer Mannheim Biochemical, Indianapolis, Ind.

TABLE II

| Enzyme | Source | Typical Substrate |
|---|---|---|
| endo-β-N-Acetylglycosaminidases | | |
| D | *Diplococcus pneumoniae* | N-linked complex type (peripheral sugars removed) |
| H | *Streptomyces plicatus* (*Streptomyces griseus*) | N-linked high-mannose and hybrid types |
| L | *Streptomyces plicatus* | N-linked low mol. wt. only |
| $C_I$ | *Clostridium perfringens* | N-linked complex type (peripheral sugars removed) |
| $C_{II}$ | *Clostridium perfringens* | N-linked high-mannose type |
| F-Gal type | *Sporotricum dimorphosphosphorum* | N-linked complex type (biantennary only, requires terminal Gal) |
| F | *Flavobacterium meminogosepticum* | N-linked high-mannose and complex types |
| endo-α-N-Acetylgalactosaminidase | *Diplococcus pneumoniae* | O-linked, only Gal-α1-3GalNAc1- |
| endo-β-N-Galactosidases | *Diplococcus pneumoniae* | Blood group A and B determinants |
| | *Escherichia freundii* *Flavobacterium keratolyticus* | Keratan sulphate and oligosaccharides containing sequence R GlcNAc-β1-3Gal-β1-4GlcNAc (or Glc) |

As can be seen, Endo-H, F, D, CI and Endo-F-Gal type all cleave the second glycosidic linkage in a glycoprotein. In the case of Endo-F-Gal type, this glycosidic linkage is between GlcNAc and Gal. For Endo-H, F, D, and CI, the cleavage is between two residues comprising GlcNAc, with specificity being defined by the substituents U, V, W, X, Y, and Z.

Endo-H cleaves N-linked glycoproteins having a high mannose content. Thus in FIG. 2, W comprises 2-150 mannose residues, Y comprises 1-2 mannose residues and X,Z,V and U are H (hydrogen). Endo-H also cleaves hybrid structures wherein W comprises 1-2 mannose residues and Y and/or Z comprise NeuNAc-Gal-GlcNAc or similar structures and V comprises H or GlcNAc. Endo-H is the preferred Type II endoglycosidase used in the formulations and methods of the invention.

Endo-D and Endo-CI have similar reactivities although these enzymes are derived from different sources. Endo-D and Endo-CI are active on N-linked oligosaccharides of glycoproteins and cleave a high mannose structure containing more than a 5-mannose carbohydrate residue in which case X comprises mannose linked by way of an α1-3 glycosidic bond to the core structure, W comprises mannose linked by way of an α1-6 glycosidic bond to the core structure and the remaining substituents are H in FIG. 2. Endo-D also cleaves a core portion of a complex or hybrid structure after removal of most antennary residues with exoglycosidases, in which case Y comprises H or GlcNAc and U comprises H or fucose in FIG. 2.

The endoglycosidase Endo-F is active on N-linked glycoproteins having a high mannose content wherein in FIG. 2 X and Y are one or more mannose residues and the remaining substituents are H. Endo-F also cleaves biantennary hybrid structures wherein X and W comprise mannose linked to the core structure by way of α1-3 and α1-6 glycosidic linkages and Y comprises NeuNAc-Gal-GlcNAc or similar structure and U comprises H or fucose. Biantennary complex structures are also cleaved by Endo-F. Such structures comprise the substrate core structure for Endo-F in FIG. 2 wherein X and Y comprise NeuNAc-Gal-GlcNAc or similar structures and U comprises H or fucose.

Endo-L has a similar reactivity in cleaving the second glycosidic linkage in N-linked glycoproteins. It is specific for low molecular weight substrates comprising Man-GlcNAc-GlcNAc-Asn. Endo-CII demonstrates a specificity similar to Endo H. Endo-α-N-acetyl galactosaminidase hydrolyzes glycoprotein containing oligosaccharides O-linked to serine or threorine where GlcNAc and Gal are the first two carbohydrate residues. The specificity of endo-β-N-galactosidase is also shown in FIG. 2 wherein R1 may be one of the mannoses from which antennas in the carbohydrate unit may be formed.

The Type II glycosidase glycopeptidase F (PNGase F) cleaves the first glycosidic linkage in N-linked glycoproteins between asparagine and GlcNAc. It cleaves high mannose structures wherein W, X and Y comprise one or more mannose residues and V and Z comprise H with fucose being absent from the first carbohydrate residue GlcNAc. It also cleaves hybrid structures wherein W and X comprise mannose, Y and/or Z comprise NeuNAc-Gal-GlcNAc or similar structure, V comprises H or GlcNAc with fucose typically being absent from the first carbohydrate residue. Complex structures are also cleaved by glycopeptidase F. Such structures comprise the core structure shown in FIG. 2 wherein Y and W comprise NeuNAc-Gal-GlcNAc or similar structure, X and Z comprise H, NeuNAc-Gal-GlcNAc or similar structure, V comprises H or GlcNAc and fucose is sometimes present on the first carbohydrate residue GlcNAc.

Endo-β-N-galactosidase is known to cleave glycosydic linkages within oligosaccharides on a glycoprotein or glycolipid. A typical glycoprotein substrate together with the cleavage site for Endo-β-N-galactosidase is shown in FIG. 2 where $R_2$ is protein, lipid or carbohydrate, and $R_1$ is a sugar residue or hydrogen.

Of course, the invention is not limited by the present known specificity of endoglycosidases. Until recently, the endoglycosidases which have been commercially available have been expensive due to their relatively low levels of expression in their naturally occurring sources. Accordingly, the reactivity of such enzymes has not been broadly investigated. However, with the advent of molecular cloning, greater amounts of endoglycosidase have been or will be made available. To the extent that alternate reactivity and specificity may be discovered for these or other endoglycosidases, such reactivity is intended to be within the scope of the invention.

Accordingly, as used herein, a "Type II endoglycosidase-reactive substance" (also referred to as a "Type II-reactive substance" or a substance containing a "Type II reactive linkage") is any substance which is reactive with a Type II endoglycosidase. Included within Type II reactive substances, of course, are glycoside-containing substances and glycoprotein. Also included, however, are (1) other, as yet, unknown substrates reactive with Type II endoglycosidase at other than a glycosidic linkage, and (2) multicomponent aggregates containing components having Type II reactive linkages.

For example, microorganisms, such as bacteria, can be removed from surfaces by treatment with Endo-H. It is presently not known how this result occurs. Bacteria are not known to contain linkages which are normally reactive with Endo-H and the details of their attachment to surfaces, other microorganisms and other substances is not well understood. Yet, bacteria removal by Endo-H has been observed.

Further, other stains may involve complex aggregates of substances some of which or all of which are reactive with Type II endoglycosidase. The term Type II reactive substance covers all such situations. Thus, uses of Type II endoglycosidase include (1) cleaning surfaces containing Type II-reactive substances, (2) treating Type II-reactive substances to prevent attachment to a surface, and (3) treating Type II-reactive substances such as microorganisms to produce an antimicrobial effect.

The Type II endoglycosidases used in the invention can be obtained from the organisms listed in Table II according to methods known to those skilled in the art. Some of the Type II endoglycosidases in Table II, e.g., Endo-H from *Streptomyces plicatus* (initially classified as *Streptomyces griseus*) and produced in *S. plicatus* or *S. lividans* and Endo-D from *Diplococcus pneumoniae*, are commercially available from Boehringer Mannheim Biochemical, Indianapolis, Ind. Besides the commercially available preparations, Endo-H may be derived from *E. coli* transformed with a plasmid encoding the Endo-H gene from *Streptomyces plicatus* and the promoter from alkaline phosphatase (Oka, T., et al. (1985) *Proc. Natl. Acad. Sci. USA*, 82, 7212–7216) by methods similar to that reported for the cloning and expression of Endo-H from *Streptomyces plicatus* in *E. coli* (Robbins, et al. (1981) *J. Biol. Chem.* 256; 10 640). See also Trumbly R. J. et al. (1985) *J Biol. Chem.*, 260, 5638. Endo-H may also be derived from Streptomyces cells engineered to express Endo-H derived from *Streptomyces plicatus* (EPO Publication No. 0179449, Apr. 30, 1986). Alternatively, Endo-H may be produced by any appropriate host cell such as *Bacillus subtilis* using techniques well known to those skilled in the art. The amino acid and DNA sequences of Endo-H for *S. plicatus* (*S. griseus*) have been published. Robbins, P. W., et al. (1984) *J. Biol. Chem.*, 259, 7577–7583.

The Endo-H used in the examples herein was obtained commercially or from *E. coli* or *B. subtilis* hosts transformed to express Endo-H from *S. plicatus*.

One unit of Endo-H activity is the amount of enzyme required to release 1$\mu$ mole of ($^3$H)-dansyl-Asn-GlcNAc from ($^3$H)-dansyl-Asn-(GlcNAc)$_4$(Man)$_6$ at pH 5.5 at 37° C. in one minute. Tarentino, A. et al. (1978) *Methods in Enzymology*, 50,574. The unit activity of other Type II endoglycosidases are similarly defined by an appropriate substrate.

Of course, other Type II endoglycosidases may exist which have not yet been identified. Such Type II endoglycosidases as well as the ones described herein, including allelic variations and genetically engineered modifications of such endoglycosidases are within the scope of the present invention.

Glycosides and glycoside-containing substances often become bound to a wide variety of surfaces. Thus, for example, glycoproteins, such as those associated with blood (e.g., glycosylated hemoglobin), can stain the surfaces of fabrics used for clothes, linen and the like. Such stains have heretofore been highly resistant to complete removal by treatment with detergents or detergents in combination with various enzymes not comprising the endoglycosidases utilized in the present invention. A further glycoside-containing substance which stains surfaces such as fabric and which is also difficult to remove by known techniques comprises fecal matter. Such fecal stains include various glycosides and glycoside-containing substances associated with intestinal bacteria (e.g., peptidoglycans), catabolic excretions, including glycoproteins, and non-absorbed nutrients and the like.

Other surfaces to which glycosides or glycoside-containing substances may be bound include the surfaces of hard and soft contact lenses. Soft contact lenses are typically hydrophilic cross-linked polymers having a hydrogel structure or are made of silicon polymers. See, e.g., U.S. Pat. Nos. 3,403,393 and 2,976,576. Hard contact lenses, on the other hand, are typically made of methacrylate or methylmethacrylate polymers. Other surfaces include naturally occurring biofilms, cardiac pacemaker leads and power packs, cellular and mucosal surfaces, tooth enamel, filters used to remove bacteria and particulate material in processing foods; chemicals and the like; air conditioning filters; the surfaces of various structural components exposed to an aqueous environment, e.g., boats, piers and the like; plastics and composites such as formica; and metals or metal alloys such as steel, aluminum, etc.

As will be shown in detail hereinafter, Type II endoglycosidases alone or in combination with a second enzyme such as subtilisin, either with or without detergent, effectively increases the removal of blood and fecal stains from cloth swatches. It is not known precisely how such stains adhere to such swatches. However, the enhanced removal of such substances from these swatches by Type II endoglycosidase, alone or in combination with other agents, suggests that at least one glycosidic linkage is interposed between the fabric and that part of the stain which is released upon treatment with Type II endoglycosidase. Based on these results, the following are proposed mechanisms of the binding of glycoside-containing substances to a surface and the release and/or removal of such substances by Type II endoglycosidase. These proposed mechanisms, however, should not be considered as a limitation to the scope of the invention.

Figures

Thus, as shown in FIG. 5A, a glycoside-containing substance may be bound to a surface other than by an immunological bond. In this regard, an "immunological bond" is one which exists between an antigen and an antibody, specific for that antigen (polyclonal or monoclonal). As shown in FIG. 5A, the glycoside-containing substance has a proximal portion bound to the surface and a distal portion extending outwardly from the proximal portion. The proximal and distal portions are joined by a glycosidic linkage with which Type II endoglycosidase is reactive. As further shown in FIG. 5A, when treated with Type II endoglycosidase, the distal portion of the glycoside-containing substance is "released" from the proximal portion of the glycoside-containing substance. To the extent that this distal portion is not bound by other means to the surface, it is also readily "removed" from the surface and may be washed away with a fluid.

In FIG. 5B, a glycoside-containing substance, in this case a glycoprotein containing a carbohydrate unit and protein unit, is shown bound to a surface. This glycoside-containing substance further contains a carbohydrate portion and an aglycon portion joined by a glycosidic linkage which is reactive with Type II endoglycosidase. In this particular case, the glycoside-containing substance (glycoprotein) is bound to the surface through the carbohydrate portion of the glycoside-containing substance. When treated with Type II endoglycosidase, the aglycon portion is released from the carbohydrate portion of the glycoside-containing substance. As in FIG. 5A, to the extent that the aglycon portion is not further bound to the surface by other means, the aglycon portion is also removed from the surface.

FIG. 5C depicts the situation where a glycoside-containing substance is bound to a surface by way of at least two points of attachment. As indicated, a glycosidic first linkage exists between the surface and the glycoside-containing substance. In addition, a second linkage reactive with a second enzyme is also present between the surface and the portion of the glycoside-containing substance to be removed. If treated only with Type II endoglycosidase, the portion of the glycoside containing substance distal from the first glycosidic linkage is released from the surface at least to the extent that it was bound through the first glycosidic linkage. If contacted with a second enzyme reactive with the second linkage shown, the portion of the glycoside-containing substance as distal from the first glycosidic linkage and the second linkage is released from the surface. To the extent that this distal portion is not otherwise bound to the surface, i.e., by other contact points which may be reactive with other enzymes or susceptible to detergents and/or surfactants, this distal portion is effectively removed from the surface.

Figure 5D:
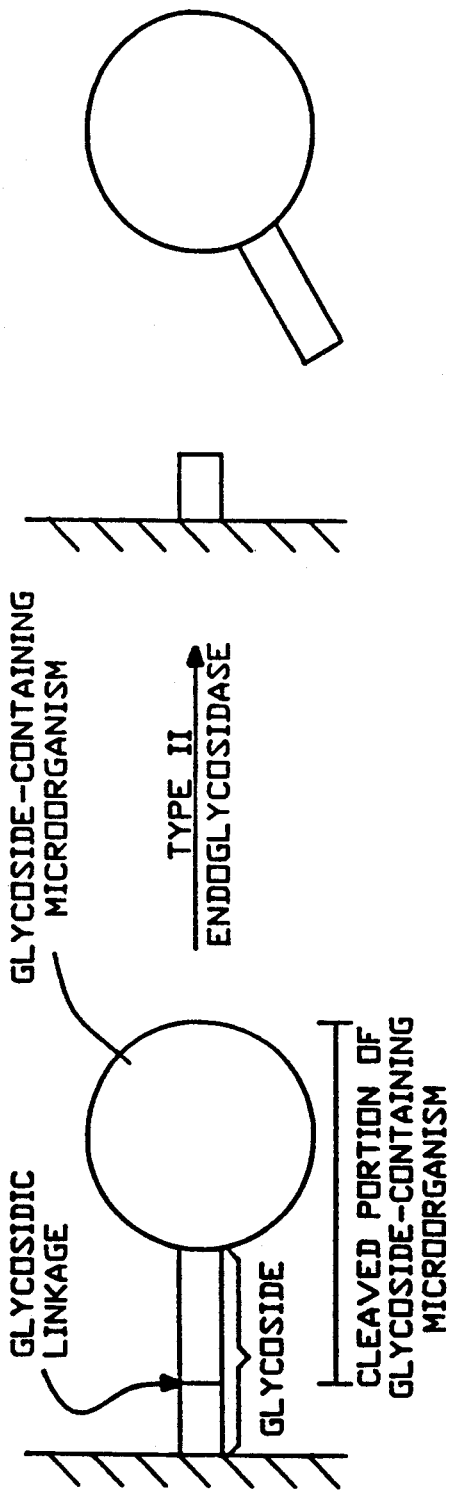

FIG. 5D shows a microorganism bound to a surface through at least part of the glycoside portion of said microorganism. The glycoside portion contains a glycosidic linkage reactive with Type II endoglycosidase. A cleaved portion of the microorganism distal from the glycosidic linkage is released from the surface when treated with Type II endoglycosidase. To the extent that this cleaved portion is not otherwise bound to the surface it is also removed from the surface. However, multiple points of contact may exist with the surface which may require further treatment with other enzymes and/or detergent or surfactant.

Figure 5E:
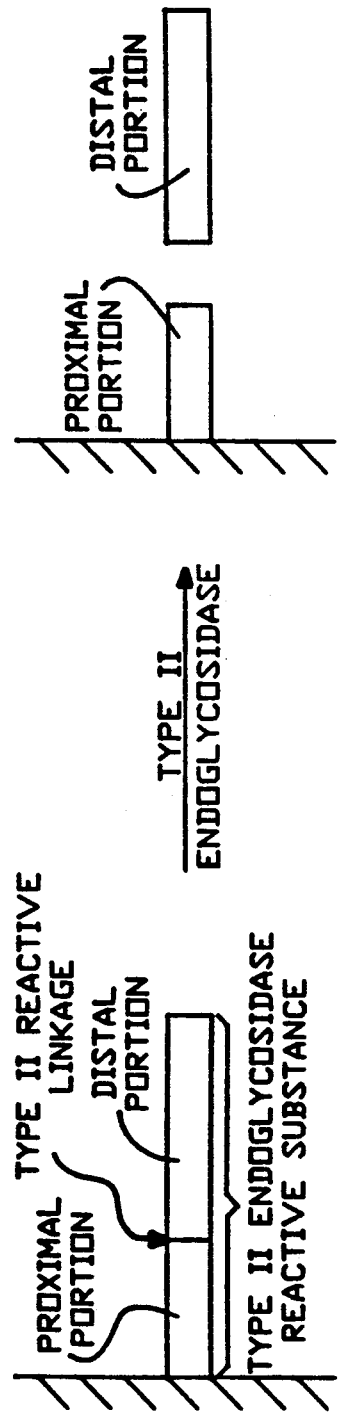

In FIG. 5E, a Type II endoglycosidase-reactive substance is shown bound to a surface. This Type II reactive substance has a proximal portion bound to the surface and a distal portion extending outwardly from the proximal portion. The proximal and distal portions are joined by a Type II reactive linkage which refers to a linkage reactive with a Type II endoglycosidase. When treated with Type II endoglycosidase, the distal portion of the Type II reactive substance is "released" from the proximal portion of the Type II reactive substance. It is to be understood that Type II reactive substances may comprise molecules, microorganisms or aggregates of various components which may become attached to a surface. To the extent that the distal portion of the Type II reactive substance is not bound by other means to the surface, it is also readily "removed" from the surface and may be washed away with a fluid.

The amount of Type II endoglycosidase used to produce the removal of the substances identified in the figures is defined functionally as an "amount effective" for removal of the particular substance from a surface. This amount may vary depending on the substance and surface to be treated. Typical amounts are disclosed in more detail herein with regard to the specific embodiments disclosed.

Second Enzymes

"Second enzymes" include proteases, lipases, glycosidases such as lysozyme and combinations thereof. Various proteases which may be combined with Type II endoglycosidase include subtilisin, bromilain, papaine, trypsin, chymotrypsin, pancreatin, lysozyme and combinations thereof. Such enzymes may be derived from natural sources, e.g., subtilisin from *Bacillius subtilis* or from genetically engineered clones, e.g., subtilisin and mutant subtilisins as described in EPO Publication No. 0130756. See also, Wells, J. A., et al. (1983) *Nucleic Acids Res.*, 11, 7911–7915; Yang, M., et al. (1984) *J. Bacteriology*, 160, 15–21; Estell, D. A., et al. (1985) *J. Biological Chemistry*, 260, 6518–6521. Many such enzymes, of course, are available from commercial sources.

In addition, Type II endoglycosidases may be combined with lipases such as bacterial, mammalian and fungal lipases and combinations thereof.

Glycosidases which may be used as a second enzyme include exoglycosidases, a second Type II endoglycosidase and Type I endoglycosidases. Examples include α- and β-amylase, cellulase, pectinase, hemicellulase, dextranase, various glucanases, and the like and combinations thereof.

Moreover, Type II endoglycosidase may be combined with more than one of the above classes of second enzymes to facilitate the removal of a glycoside-containing substance from a surface.

When a Type II endoglycosidase is combined with one or more second enzymes, the ratio of Type II endoglycosidase to second enzyme is preferably about 0.01 to 100 and most preferably 1 to 1.

Disulfide Cleaving Reagents

Type II endoglycosidases may also be used in combination with detergents, either alone or in combination with one or more second enzymes and/or disulfide-cleaving reagents to form a detergent formulation. Substances capable of cleaving disulfide bonds are varied, but fall generally into three categories: oxidizing agents, reducing agents, and miscellaneous addition substrates such as those exemplified by fumaric acid and sodium sulfite. Suitable oxidizing agents include hydrogen peroxide, performic acid, sodium perborate, and oxidizing bleaches. Effective reducing agents include dithiothreitol (DTT), β-mercaptoethanol (BME), sodium borohydride, and the like.

Alternate disulfide cleavage reagents which are not easily classified include mercuric chloride, nitroprusside, tributylphosphine, and phosphothiolate. A particularly useful cleavage reagent is sodium sulfite, which results in sulfitolysis of the disulfide according to the reaction: $R\text{-}S\text{-}S\text{-}R + SO_3^{-2} \; R\text{-}S\text{-}SO_3^{-2} + \text{-}SR$. The equilibrium of this reaction may be shifted by removal of the thiol anion using heavy metal ions or oxidizing agents. The oxidizing power may be provided by aeration or an oxidizing agent, such as $CuSO_4$ or sodium perborate.

The foregoing list of substances capable of cleaving disulfides is not meant to be comprehensive, and conversely does include substances which are effective but not necessarily appropriate for a commercial product. In order to be successful commercially, the added substance must be relatively inexpensive and must not have undesirable properties for its intended use. Thus, for example, while the use of mercuric chloride would be workable in carrying out the process of the invention, it would not be suitable for ordinary detergent products intended for commercial use. β-mercaptoethanol and DTT are feasible commercially, except that they have mildly offensive odors. Particularly preferred substances, therefore, for commercial formulation, are sodium sulfite (preferably in combination with an oxidizing agent) or hydrogen peroxide, which are inexpensive and are relatively safe. Reviews of materials which are useful in the cleavage of disulfide bonds are found, for example, in *Chemical Modification of Proteins*, Means, G. E., et al., eds (1971), Holden-Day, Inc. San Francisco, Calif., Ch 8; and *Chemical Reagents for Protein Modification*, Lundbald, R. L. et al., eds (1984), CRC Press, Inc., Boca Raton, Fla., Ch. 7.

Typically, the Type II endoglycosidase alone or in combination with one or more second enzymes forms 0.01–3% wt/wt of the detergent compositions of the invention, and may include disulfide-cleaving reagents, ranging from about 10–40% wt/wt thereof. The amounts present depend, of course, on the nature of the endoglycosidase (and second enzyme, if used) and the disulfide cleavage reagent, the dilution of the detergent in the wash solution, and the conditions of the wash. However, the ranges given are generally typical.

In one embodiment of the invention, surfaces having glycoprotein containing substances bound thereto are treated with the combination (simultaneous or sequential) of a disulfide cleaving reagent, a Type II endoglycosidase and a second enzyme at suitable pH, temperature, for an appropriate period of time. These conditions are, of course, variable according to convenience, and the selection of the Type II endoglycosidase, protease and the substance to cleave disulfides to some extent depends on this selection. However, convenient conditions frequently encountered are pH values between 5 and 12. Temperatures of 20°–55° C., particularly around 40°–55° C., and times of up to 20 minutes, usually around 10–15 minutes are typical and preferred. The preferred times and temperatures are those generally utilized in household washing machines, neighborhood laundromats, and professional laundry services, since in order to be commercially practical, the process needs to be conducted under conditions ordinarily available to the user.

In another embodiment of the invention, conventional washing procedures using commercial detergents are used and the Type II endoglycosidase, second enzyme and disulfide-cleaving substance are provided, either separately or together, as an additive, much in the manner of the methods in which bleach is used. Thus, these may be added along with the detergent at the beginning of the wash cycle or at some intermediate point, for example, after approximately half of the wash cycle is completed. If handled in this way, assuming an approximately 1:500 dilution of a solid or liquid detergent composition (approximately 2 mg/ml of the solid), arbitrary amounts of the Type II endoglycosidase, second enzyme and disulfide cleaving reagents may be added without the upper limit imposed by this dilution. (If the Type II endoglycosidase, second enzyme and disulfide cleaving reagent had been added to the detergent composition originally, and if, for example, the disulfide cleaving reagent constituted 50% of the composition, only 1 mg/ml would result in the final wash solution. However, if these materials are added separately, amounts most effective for the particular Type II endoglycosidase, disulfide cleaving reagent and second enzyme may be added.)

With respect to the Type II endoglycosidase and second enzyme, only very small quantities are usually required. Typically, the Type II endoglycosidase and second enzyme are added to a final concentration of approximately 1–500 μg/ml of wash solution for each enzyme. In the case of the disulfide-cleaving reagent, however, larger amounts than would be permitted by the dilution of the detergent may be desirable. For example, cleavage of disulfide bonds using sodium borohydride may conveniently be carried out with concentrations as high as 0.2M reagent in the present of similar quantities of buffer (Lundbald, R. L., et al., *Chemical Reagents for Protein Modification*, supra).

Although such high amounts are conventional, they are not necessarily required, and lower concentrations are workable. Sulfitolysis is ordinarily carried out in sodium sulfite concentrations of the order of 0.1M, although concentrations as low as 0.01M and lower can also be used. DTT is effective when supplied at concentrations of the order of 0.02–0.1M. In short, the disulfide-cleaving reagent concentration can be varied over a wide range for any of these reagents and effectiveness maintained. The optimum concentration for a particular application will, of course, depend on the nature of the stain and the nature of the reagent, as well as the conditions of the wash procedure, including time, temperature, and pH.

In an alternative and more convenient approach, the Type II endoglycosidase, second enzyme and disulfide-cleaving substance are added to the original detergent composition, and the process is conducted as a standard wash procedure using these modified detergents. Under these circumstances, the detergent composition will correspond to that described above, but the amount of the composition can also be varied over the range of approximately 0.5 mg/ml–10 mg/ml or greater of the wash solution, depending, again, on the conditions of the wash solution and procedure, and on the solubilities of the detergent components. In any case, the inclusion of the Type II endoglycosidase, disulfide-cleaving reagent and second enzyme in the detergent limits the concentrations of these components in accordance with the dilution of the detergent. Thus, even if a 1:100 dilution is used (10 mg/ml), and the disulfide-cleaving reagent for example, is limited to 50% of the detergent composition, a maximum concentration of 5 mg/ml disulfide-cleaving reagent in the resulting wash solution is an upper limit. Typically, of course, the concentration of disulfide-cleaving reagent in the detergent will be less than 50%, mandating even lower concentrations of the disulfide-cleaving reagent.

The detergent compositions of the invention contain mostly detergent active substances, relatively smaller amounts of disulfide-cleaving reagent, if used, and quite small amounts of Type II endoglycosidase and second enzyme, if used, which is especially desirable in view of the cost of enzymic components. Thus, in general, the preparation will contain 60–90% detergent active substances, including conventional commercial detergent additives such as surfactant builders and whiteners, 0.01–3% Type II endoglycosidase and second enzyme, and approximately 10–40% disulfide cleavage reagent.

Of course, it is also possible to add only one of these three additives to the original detergent and to supply the other separately to the wash liquid. In particular, the Type II endoglycosidase may be added to a prewash, followed by a detergent containing the second enzyme, or addition of the detergent containing endoglycosidase may be followed or preceded by treatment with the second enzyme.

Cleaning Compositions

Endo D, F and H are preferred Type II endoglycosidases for use in cleaning compositions. Endo-H is most preferred.

For removal of glycoside-containing substances, the compositions herein preferably comprise from about 0.1 ppm (parts per million) to 1200 ppm, more preferably from about 1 ppm to 1000 ppm, most preferably from about 20 ppm to about 200 ppm, of Type II endoglycosidase, depending on the type of composition. Cleaning compositions are preferred. Laundry detergent compositions are most preferred for use herein, and preferably comprise from about 0.1 ppm to 1200 ppm of Type II endoglycosidase, preferably from about 20 ppm to 200 ppm of Endo D, F or H, most preferably from about 50 ppm to 125 ppm Endo H.

When used to control or remove microorganisms, the compositions preferably comprise from about 0.1 ppm to 1200 ppm, more preferably from about 1 ppm to 1000 ppm, most preferably from about 20 ppm to 400 ppm, of Type II endoglycosidase, preferably Endo-H. Cleaning compositions are preferred and preferably comprise the same amounts of Type II endoglycosidase, preferably Endo-H.

Described below are suggested types of compositions which comprise Type II endoglycosidase for removal of glycoside-containing substances and/or microorganisms. The compositions can be made and used in any way which does not destroy enzyme activity. They can be made up of any ingredients which do not unduly hinder the activity of the enzyme. The compositions can be laundry detergents, dishwashing detergents, hard surface cleaners, dental enamel cleaners, liquid and bar soaps, anti-acne compositions, antiperspirants, shampoos, face creams, fruit and vegetable surface preservatives, or fabric softeners.

In addition to the cleaning of fabrics using common cycles in washing machines, the cleaning compositions herein may also be used for removing glycoside-containing substances and/or microorganisms from other surfaces such as metals and metal alloys such as found in surgical instruments, pipelines, metal containers and the like, and plastics and composite materials such as Formica and the surfaces of boats, piers and the like. Depending upon the particular application, the composition may comprise Type II endoglycosidase alone or in combination with a disulfide cleaving reagent, second enzyme and/or detergent surfactant.

Type II endoglycosidase may also be formulated in a composition for removing glycoside-containing substances and/or microorganisms including yeast, fungi, algae and bacteria from "biological surfaces" such as surfaces of skin, skin pores, hair, hair follicles and tissue. Thus, those skilled in the art of shampoo formulations, conditioner formulations, soap formulations and the medicinal arts can readily adapt the above disclosure for detergent formulations to employ Type II endoglycosidase in such applications. When so formulated, such compositions are useful in removing glycoside-containing substances which may adhere to such surfaces.

Type II endoglycosidase may also be formulated in a composition for removing glycoside-containing substances and/or microorganisms, especially yeast and fungus, from the surfaces of plants such as fruits and vegetables. Such compositions preferably include nonionic surfactant.

In addition, Type II endoglycosidase may be formulated in deodorant compositions in a manner known to those skilled in the art to provide endoglycosidase activity to remove glycoside-containing substances and/or microorganisms responsible for undesirable odors. Such deodorant formulations employing Type II endoglycosidase may include modifications of formulations for stick, creams and aerosol deodorants known to those skilled in the art.

Further, Type II endoglycosidase may be formulated for the treatment of acne which usually results from inflammation, at least to the extent that glycoside-containing substances and/or microorgansims responsible for or involved in such inflamation are bound to a surface. As with the above formulations, those skilled in the art are capable of modifying known acne formulations to incorporate a Type II endoglycosidase alone or in combination with other enzymes, detergents and/or surfactants.

When used to treat contact lens, Type II endoglycosidase suitably is supplied at a concentration of about 0.1–20 $\mu$g/ml in the cleaning compositions, and the concentration of a second enzyme such as a protease is in the same range if such second enzymes are utilized. Treatment times can vary from about five minutes to about 15 hours, but a standard convenient cleaning time is overnight, so that the wearer can allow the lenses to soak while he sleeps. A variety of protocols are suitable, but ones that are particularly preferred are the use of a single solution containing Type II endoglycosidase and the second enzyme (if used) conducted from 10 minutes to two hours or overnight at room temperature, or a 10-minute to two-hour presoak in the presence of Type II endoglycosidase solution, followed by a similar overnight treatment with a solution containing a second enzyme.

Preferred general purpose second enzymes for contact lens formulation include proteases such as papain, pancreatin and subtilisin. The preferred Type II endoglycosidase enzyme is Endo-H from *Streptomyces plicatus*. A single second enzyme protease may be used, or the composition may contain a mixture of second enzymes.

In addition, the contact lens compositions may include additional components which aid in the overall enzymatic degradation. Particularly useful among these are disulfide cleavage reagents such as 2-mercaptoethanol, cysteine hydrochloride, dithiothreitol, dithioerythritol, sodium bisulfate, sodium metabisulfite, thiourea, and the like, generally preferred in a range of about 0.01–5% by weight preferably 0.05–1% by weight. In addition, detergents may be included in the composition to aid in the wetting of the lens with the enzyme-containing solution. Suitable detergents include sodium dodecyl sulfate, sodium monolaurate, nonionic surfactants such as alcohol ethoxylates (e.g., polyethoxyethanol) anionic surfactants such as ether sulfonates, linear alkylbenzene sulfonates, sodium lauryl sulfate, and the like.

Suitable buffers and stabilizers for contact lens cleaning may also be used and include sodium or potassium citrate, citric acid, boric acid, sodium EDTA, various mixed phosphate buffers and $NaHCO_3$. Generally buffers and stabilizers may be used in amounts ranging from about 0.001 to about 2.5% and preferably about 0.1 to 1% by weight. It should be understood that the foregoing description of the amounts of the various compounds which may be used in the present invention for cleaning contact lens are stated in percentage of ingredients in solution (wt/vol). The formulation may also take the form of one or more conventional solid dosage forms such as tablets suitable for use in measured quantity of a suitable solvent such as water. The percentage composition of the solid dosage forms is such that when dissolved in a specified volume of water, the solution will have the percentage composition within the ranges set forth in the specification. If solid dosage forms are used, the formulation may include conventional lubricants, binders, and excipients which include glycerol, sorbitol, boric acid, propylene glycol, polyethylene glycols, dextran, methylcellulose, hydroxyethylcellulose, water soluble salts of carboxymethylcellulose, or naturally occurring hydrophilics such as gelatin, alginates, tragacanth, pectin, acacia and soluble starches.

Typical compositions and protocols useful in cleaning contact lens include the following:

1. The composition contains 1–100 μg/ml Type II endoglycosidase. The lenses are removed and placed in contact with the solution for a period of 12 hours at 22° C. The lenses are removed from the cleaning solution and rinsed.

2. Solution A contains 10 μg/ml of Type II endoglycosidase; solution B contains 5 μg/ml subtilisin. The lenses are soaked in solution A for 30 minutes at 25° C., removed, and immersed in solution B for 10 hours at 25° C.

3. The cleaning solution contains 10 μg/ml of the protease pepsin and 10 μg/ml of Type II endoglycosidase. The lenses are soaked in this solution for 5 hours at 20° C.

4. The cleaning solution contains 5 μg/ml subtilisin, 5 μg/ml Type II endoglycosidase, and 10 mM 2-mercaptoethanol. The lenses are immersed in this solution for 5 hours at 30° C.

5. The cleaning solution contains 7 μg/ml subtilisin, 3 μg/ml Type II endoglycosidase, 10 mM 2-mercaptoethanol, and 2% sodium dodecyl sulfate (SDS). The lenses are soaked in this solution for 3 hours at 20° C.

6. The cleaning solution contains 4 μg/ml subtilisin, 2 μg/ml trypsin, 10 μg/ml Type II endoglycosidase, and 2% SDS. The lenses are soaked in this solution for 7 hours at 20° C.

7. Solution A contains 4 μg/ml subtilisin and 2 μg/ml trypsin in 2% SDS. Solution B contains mercaptoethanol. The lenses are immersed in solution B for 20 minutes at 30° C. and then in solution A for 6 hours at 25° C.

In all the foregoing examples, the lenses are thoroughly rinsed in saline before being returned to the wearer's eyes.

The compositions herein can be formulated in a variety of physical forms, including liquids, gels, pastes and solid particles such as powders and granules. The compositions can be formulated as laundry detergents, such as disclosed in U.S. Pat. Nos. 4,507,219, 4,318,818, 4,605,509 and 4,412,934; dishwashing detergents such as disclosed in U.S. Pat. Nos. 4,714,562, 3,630,923, 4,133,779, 4,316,824 and 4,555,360; hard surfaces cleaners such as disclosed in U.S. Pat. Nos. 4,414,128, 3,679,608, 3,985,668 and 4,005,027; fabric softeners such as disclosed in U.S. Pat. Nos. 3,944,694, 4,073,996, 4,424,134 and 4,661,269; bar soaps such as disclosed in U.S. Pat. Nos. 3,993,722 and 3,070,547; shampoos such as disclosed in U.S. Pat. Nos. 4,345,080, 4,704,272 and 4,741,855; antiperspirants such as disclosed in U.S. Pat. No. 4,725,432; anti-acne products such as disclosed in U.S. Pat. Nos. 4,318,907 and 4,608,370; and oral compositions such as disclosed in U.S. Pat. No. 4,684,518. The above patents are incorporated herein by reference.

The compositions preferably have a pH from about 4 to 10, more preferably from about 5 to 8 for good enzyme performance.

Laboratory work on microorganism removal has shown that, in order to obtain effective removal, the bathing of the surface holding the microorganisms in some instances requires a physical or chemical action to remove the microorganisms. Microorganisms tested include:

*Escherichia coli* including Type 1 and 3 fimbriae
*Staphylococcus aureus*
*Staphylocooous epidermidis*
*Serratia marcescens*
*Streptococcus mutans*
*Streptococcus sanguis*
*Bacillus sp.*
*Candida sp.*
*Aspergillus sp.*

In the case of removal of bacteria such as *E. coli*, for example, the surface-bound microorganisms may be treated with Endo-H and then removed by chemical action, such as by treatment with an antimicrobial agent, or a physical action, such as by rinsing with water or hand wiping. It is preferred for liquid and bar soaps, dental enamel cleaners, antiperspirants, anti-odor fabric softeners and anti-acne compositions that the composition include an anti-microbial agent, such as Irgasan ® (Ciba-Geigy) or chlorhexidine, in addition to the Endo-H. An antimicrobial agent is not required in the composition (for example a hard surface cleaner) when physical action such as water rinsing or wiping by hand will occur.

Preferred herein are detergent cleaning compositions, especially granular and liquid laundry detergent compositions. These detergent cleaning compositions preferably comprise from about 1% to 90%, more preferably from about 5% to 50%, by weight, of detergent surfactants, most preferably from about 10% to 40% by weight.

Surfactants useful in the detergent compositions herein include well-known synthetic anionic, nonionic, amphoteric and zwitterionic surfactants. Typical of these are the alkyl benzene sulfonates, alkyl- and alkylether sulfates, paraffin sulfonates, olefin sulfonates, alkoxylated (especially ethoxylated) alcohols and alkyl phenols, amine oxides, alpha-sulfonates of fatty acids and of fatty acid esters, alkyl betaines, and the like, which are well known from the detergency art. In general, such detersive surfactants contain an alkyl group in the $C_9$–$C_{18}$ range. The anionic detersive surfactants can be used in the form of their sodium, potassium or triethanolammonium salts; and the nonionic surfactants generally contain from about 5 to about 17 ethylene oxide groups. $C_{11}$–$C_{16}$ alkyl benzene sulfonates, $C_{12}$–$C_{18}$ paraffin-sulfonates and alkyl sulfates are especially preferred in the compositions of the present type.

A detailed listing of suitable surfactants for the compositions herein can be found in U.S. Pat. No. 3,936,537, Baskerville, issued Feb. 3, 1976, incorporated by reference herein. Commercial sources of such surfactants can be found in McCutcheon's *Emulsifiers and Detergents*, North American Edition, 1984, McCutcheon Division, MC Publishing Company, also incorporated herein by reference.

Useful detergency builders for the detergent compositions herein include any of the conventional inorganic and organic water-soluble builder salts, as well as various water-insoluble and so-called "seeded" builders. The instant laundry detergent compositions preferably comprise from about 1% to 75%, more preferably from about 5% to 40%, most preferably from about 10% to 20%, by weight of detergent builders. These compositions preferably have a pH of from about 6 to 10.

Nonlimiting examples of suitable water-soluble, inorganic alkaline detergent builder salts include the alkali metal carbonates, borates, phosphates, polyphosphates, tripolyphosphates, bicarbonates, silicates and sulfates. Specific examples of such salts include the sodium and potassium tetraborates, bicarbonates, carbonates, tripolyphosphates, pyrophosphates, and hexametaphosphates.

Examples of suitable organic alkaline detergency builder salts are: (1) water-soluble amino polyacetates, e.g., sodium and potassium ethylenediaminetetraacetates, nitrilotriacetates, and N-(2-hydroxyethyl)nitrilodiacetates; (2) water-soluble salts of phytic acid, e.g., sodium and potassium phytates; (3) water-soluble polyphosphonates, including sodium, potassium and lithium salts of ethane-1-hydroxy-1,1-diphosphonic acid, sodium, potassium, and lithium salts of methylenediphosphonic acid and the like.

Seeded builders include such materials as sodium carbonate or sodium silicate, seeded with calcium carbonate or barium sulfate. Hydrated sodium zeolite A having a particle size less than about 5 microns is particularly desirable.

A detailed listing of suitable detergency builders can be found in U.S. Pat. No. 3,936,537, incorporated herein by reference. Preferred builders are fatty acids, polycarboxylates, polyphosphates and mixtures thereof.

Optional detergent composition components include enzymes (e.g., proteases and amylases), peroxygen bleaches and bleach activators, halogen bleaches (e.g., sodium and potassium dichloroisocyanurates), soil release agents (e.g., methylcellulose), soil suspending agents (e.g., sodium carboxymethylcellulose), fabric brighteners, enzyme stabilizing agents, color speckles, suds boosters or suds suppressors, anticorrosion agents, dyes, fillers, germicides, pH adjusting agents, nonbuilder alkalinity sources, and the like.

Endoglycosidase Plus Antimicrobial Agents

Of the Type II endoglycosidases, endo-$\beta$-N-acetylglucosaminidase H, D, F and/or PNGase F are preferred for formulating antimicrobial compositions and for use in the antimicrobial methods herein. Endo-H is most preferred.

When the Type II endoglycosidase is used alone, it is formulated such that its concentration produces an antimicrobial effect. When the antimicrobial composition comprises at least two different components, i.e. a Type II endoglycosidase and one or more antimicrobial agents, each of the components are present at a concentration sufficient to produce an antimicrobial effect. The amount of at least one component in said compositions is generally less than the amount required for that component to produce the same antimicrobial effect if used alone in a similar composition.

As used herein, an "antimicrobial effect" includes the removal, killing, inhibition of growth, change in gross morphology, protoplast formation and/or degradation of the cell wall of a microorganism when contacted with a Type II endoglycosidase alone or in combination with a second component comprising an antimicrobial agent.

As used herein, an "antimicrobial method" refers to a method which produced an antimicrobial effect. In one aspect of the invention, the antimicrobial method causes the killing of microorganisms, the inhibition of microorganism growth, and/or changes in the gross morphology of the microorganism. In another aspect of the invention, the antimicrobial method causes the removal of a microorganism from a surface. In the antimicrobial methods to remove microorganisms from surfaces, it is preferred that the surface be treated with the antimicrobial agent and the Type II endoglycosidase simultaneously, rather than treating with the additional antimicrobial agent immediately after treating with Type II endoglycosidase. In some applications of the antimicrobial methods, a combined antimicrobial effect may be produced, e.g. killing and/or growth inhibition may occur in combination with microorganism removal from a surface.

As used herein, an "antimicrobial composition" refers to a composition containing at least two different components: a Type II endoglycosidase and a different component comprising an antimicrobial agent. Such antimicrobial compositions have variable antimicrobial effects depending upon the amount and choice of Type II endoglycosidase and antimicrobial agent. Observed antimicrobial effects include the killing of microorganisms and/or inhibiting microorganism growth, the removal of microorganisms from a surface and the prevention of microorganism attachment to surfaces.

As used herein, an "antimicrobial-effective concentration" of Type II endoglycosidase generally refers to the final concentration of Type II endoglycosidase used alone to contact a microorganism to produce an antimicrobial effect.

As used herein, an "antimicrobial agent" is a second different component of an antimicrobial composition. Such antimicrobial agents in general are antibiotics and include agents which kill microorganisms and those which inhibit microorganism growth. Examples of such antimicrobial agents include bacteriocides, fungicides and algicides each of which are capable of killing or inhibiting the growth of bacteria, fungi or algae, respectively. Bacteriocides include compounds such as chlorhexidine, 2,4,4'-trichloro-2'-hydroxydiphenyl ether, Triclocarban ®, penicillins, tetracycline and Bacitracin ®. Fungicides include Nystatin ®, Amphotericin B ®, Benomyl ®, Captan ® and Dichloran ®. Other examples of antimicrobial agents include surfactant-stable antimicrobial enzymes such as surfactant-stable β-1,3-glucanases, lysozymes, proteases and chitinases, and detergent surfactants such as anionic, nonionic, zwitterionic, ampholytic and cationic surfactants known to those skilled in the art. The latter should be employed in an amount sufficient to produce an antimicrobial effect. The above antimicrobial agents identified by generic name or trademark are compositions as identified in the Merck Index, 10th Ed. (1983), Merck & Co., Inc., Rahway, N.J.

Type II endoglycosidases different from the first component of the antimicrobial compositions may also be used as an antimicrobial agent. Thus, to the extent Type II endoglycosidases are themselves antimicrobial agents (e.g. are capable of producing an antimicrobial effect, such as morphological changes or protoplast formation), they may be combined with a different Type II endoglycosidase to form an antimicrobial composition. Antimicrobial compositions may therefore comprise one or more different Type II endoglycosidase with or without one or more antimicrobial agents not comprising Type II endoglycosidase.

Preferred antimicrobial agents for use herein are chlorhexidine, 2,4,4'-trichloro-2'-hydroxydiphenyl ether, Triclocarban ®, Nystatin ® Amphotericin B ® antibiotic, anionic and nonionic detergent surfactants. A surfactant-stable antimicrobial lysozyme is disclosed in U.S. Pat. No. 5,041,236 entitled Methods and Compositions Employing Certain Lysozymes and Endoglycosidases in the names of Richard S. Carpenter and Ann M. Wolff, filed on even date as this application. Other lysozymes, e.g. hen egg white lysozyme, have been used in combination with Endo-H to produce antimicrobial effects albeit to a lesser extent and with variability in the results obtained.

The antimicrobial compositions and methods of the invention can produce an antimicrobial effect on a wide range of microorganisms including Gram-positive and negative bacteria, fungi, and algae. Such bacteria include *Escherichia coli, Streptococcus mutans, Staphylococcus epidermidis*, and *Staphylococcus aureus*. Such fungi include yeasts such as Candida and Saccharomyces, and species and filamentous fungi such as Aspergillus, Sporobolomyces, Basidiobolus and Entomophthora.

A specific advantage of combining a Type II endoglycosidase (e.g. Endo-H, D, F and/or PNGase F) with an antimicrobial agent is that less of the antimicrobial agent can be used to produce an antimicrobial effect. In some aspects of the invention, the antimicrobial agent when used with a Type II endoglycosidase produces an antimicrobial effect comprising the removal of microorganisms attached to surfaces or the prevention of their attachment to such surfaces. In other aspects, there is a negative effect on microorganism viability or microorganism morphology.

Surface treatment(s) with Type II endoglycosidase and antimicrobial agent can be performed periodically so as to prevent further growth or attachment or adhesion of microorganisms to the surfaces exposed to the treatment.

Of the Type II endoglycosidases, Endo-H, D, F and/or PNGase F are preferred. Of these, Endo-H is most preferred. In general, an antimicrobial-effective amount of Type II endoglycosidases for use in combination with antimicrobial agents is from about 1 to 1200 ppm Endo-H, D, F, and/or PNGase F, preferably from about 1 to 1200 ppm Endo-H, more preferably from about 20 to 1000 ppm Endo-H, most preferably from about 50 to 400 ppm Endo-H. The amount used depends upon the type of treatment and amount of exposure to the surface or microorganism to be treated. In general, an effective amount of antimicrobial agent, which depends upon which agent is used, is from about 0.5 to 1200 ppm, preferably 2 to 1200 ppm, most preferably from about 5 to 350 ppm chlorhexidine or 2,4,4'-trichloro-2'-hydroxydiphenyl ether, or 0.5 to 100 ppm Nystatin ®.

When Type II endoglycosidase is used alone to kill and/or inhibit microorganisms, the use of substantially more Type II endoglycosidase is generally required. For example, about 100 ppm to 1000 ppm of Endo-H has been shown to substantially decrease the viability of yeast cells exposed to such concentrations. When yeast is exposed to less than 100 ppm of Endo-H, however, a significant decrease in viability has not been observed. Although the lower limit of Endo-H necessary to adversely affect yeast viability has not yet been determined, the lower limit of its antimicrobial-effective concentration is believed to be between 10 and 100 ppm. Similar amounts of Endo-H are believed to be useful to kill and/or inhibit other microorganisms such as algae and fungi. The exact effect of Endo-H and other Type II endoglycosidases on these organisms and others, e.g., bacteria, when not used in combination with antimicrobial agents has not yet been determined. The range of antimicrobial-effective concentrations of Type II endoglycosidase for use against such organisms, however, can be routinely determined.

The antimicrobial methods and compositions of the invention have a wide applicability and include antimicrobial methods and compositions for personal care, health care and household and industrial cleaning. Thus, such methods and compositions may be used to formulate and use antimicrobial mouthwash, dentifrice or denture cleaner, as well as antimicrobial liquid or solid hand or body soaps, anti-acne medication, deodorant, shampoo and face creams and compositions for cleansing wounds or suppressing infections. Typical household applications include antimicrobial cleaning products such as liquid soap, hard surface cleaners, and liquid and granular laundry detergents. Heavy duty antimicrobial detergent compositions may also be formulated for industrial use.

Chlorhexidine is an effective oral antibacterial agent and is preferred for use in dental applications. 2,4,4'-trichloro-2'-hydroxydiphenyl ether is available as Irgasan ® DP 300 from Ciba-Geigy and is a broad-spectrum antimicrobial effective in personal care and laundry applications. Triclocarban ® from Monsanto is a bacteriostat useful in bar soaps. Traditional antibiotics can also be employed as the additional antimicrobial agent herein. Lastly, surfactant-stable antimicrobial enzymes can be used in dental applications and for preservation of shampoos and other surfactant-containing formulations. A preferred surfactant-stable antimicrobial enzyme is the lysozyme disclosed in the previously identified copending application in the names of Carpenter and Wolff. Surfactant-stability of antimicrobial enzymes can be gauged herein by retained activity in the presence of representative amounts of alkyl ether sulfate or linear alkylbenzene sulfate, for example.

The antimicrobial composition may be formulated as an antimicrobial mouthwash, dentifrice, or denture cleaner. The treatment of microorganisms to produce an antimicrobial effect (e.g. to remove or prevent microorganism attachment to natural or synthetic soft and/or hard surfaces in the oral cavity or to kill microorganisms or inhibit their growth in the oral cavity), then, essentially comprises rinsing with an antimicrobial mouthwash, cleaning the teeth with an antimicrobial dentifrice, and/or cleaning dentures with an antimicrobial denture cleaner. The antimicrobial mouthwash, dentifrice and denture cleaners herein preferably comprise Endo-H, and chlorhexidine and/or surfactant stable antimicrobial enzyme as the antimicrobial agent. Where chlorhexidine is used, the antimicrobial mouthwash, dentifrice, or denture cleaner preferably comprises from about 50 to 1200 ppm Endo-H and from about 50 to 350 ppm chlorhexidine. Where surfactant-stable antimicrobial enzyme is used, the antimicrobial mouthwash, dentifrice or denture cleaner preferably comprises from about 50 to 150 ppm Endo-H and from about 50 to 1,000 ppm surfactant-stable antimicrobial enzyme.

The antimicrobial composition may also be formulated as antimicrobial personal care or household cleaning products. In such products, Endo-H is preferably used at a concentration of from about 1 to 1200 ppm. The antimicrobial agent for use in these products is preferably chlorhexidine, most preferably at a concentration of from about 150 to 1200 ppm, or 2,4,4'-trichloro-2'-hydroxydiphenyl ether, most preferably at a concentration of from about 2 to 500 ppm. Preferred personal care or household cleaning products are liquid hand soaps, hard surface cleaners, laundry detergents and shampoo (described below).

A preferred antimicrobial liquid hand soap comprises from about 50 to 400 ppm Endo-H, from about 5 to 100 ppm 2,4,4'-trichloro-2'-hydroxydiphenyl ether, and preferably from about 1 to 40 weight % to detergent surfactant. Preferably from about 2 to 20 weight %, most preferably from about 3 to 10 weight %, detergent surfactant is employed, preferably selected from the group consisting of anionic, nonionic, zwitterionic, ampholytic and cationic surfactants. The liquid hand soap can further comprise emollient (up to about 30 weight %) and minor amounts of perfume, colorant, solvent, and opacifier.

The antimicrobial hard surface cleaners herein can be glass cleaners, abrasive hard surface cleaners, scouring cleansers, or toilet bowl cleaners. These should be substantially free of hypochlorite-generating bleaches, and other endoglycosidase-incompatible ingredients. A preferred hard surface cleaner comprises from about 100 to 1000 ppm Endo-H, and antimicrobial agent, and from about 0.1 to 20 weight % detergent surfactant. From about 2 to 10 weight %, detergent surfactant is most preferred, preferably selected from the group consisting of anionic, nonionic, zwitterionic, ampholytic and cationic surfactants. The antimicrobial hard surface cleaners herein optionally further comprise abrasive, builder, diluent, solvent, suspending agent (such as clay, carboxymethylcellulose, and polyacrylate), perfume, and/or colorant.

The antimicrobial laundry detergent herein, in addition to Type II endoglycosidase and antimicrobial agent, preferably comprises from about 1 to 99 weight %, more preferably from about 5 to 60 weight %, most preferably from about 10 to 40 weight % detergent surfactant, preferably selected from the group consisting of anionic, nonionic, zwitterionic, ampholytic and cationic surfactants. A preferred liquid or granular antimicrobial laundry detergent comprises from about 2 to 250 ppm Endo-H, from about 2.5 to 40 ppm 2,4,4'-trichloro-2'-hydroxydiphenyl ether, and from about 1 to 99 weight %, preferably from about 5 to 60 weight %, detergent surfactant. The antimicrobial laundry detergents herein optionally further comprise builder, perfume, bleach, diluent, suds suppressor, colorant, brightener, soil suspending agent, antiredeposition aids, softeners, and/or soil release agents.

The antimicrobial shampoo for use herein preferably comprises Endo-H, an antimicrobial agent, and from about 5 to 60 weight % detergent surfactant, preferably selected from the group consisting of lauryl sulfate, isoethionate, acyl amidobetaine, alkyl glyceryl ether sulfonate, and alkyl ether sulfate. Optional ingredients are suds booster, conditioner, dye, colorant, perfume and/or anti-dandruff agent.

The present antimicrobial compositions may also be in the form of a preservative or microorganism control agent for treatment of plant surfaces. Preferred are a preservative for the surfaces of fruits or vegetables or an antimicrobial product to be applied on crops for microorganism control. The latter is preferably in the form of a solution to be sprayed on crops such as corn, citrus, wheat, tobacco, soybeans, tomatoes and strawberries for control and prevention of microorganism growth.

The following is presented by way of example only and is not to be construed as limiting the scope of the invention.

EXAMPLE 1

Removal of Blood and Fecal Matter from Fabric

Separate blood and fecal matter stained (cotton fabric) swatches were washed with commercial detergents in an automatic washing machine using a warm (approximately 37° C.) wash cycle. The swatches were then rinsed and air dried. They were then incubated with various amounts and types of endoglycosidase [(0.005 U of Endo-D (Boehringer Mannheim Biochemical), or Endo-H (Boehringer Mannheim Biochemical from *S. griseus*, Catalog No. 752 967), and 0.25 U N-glycanase (PNGase F or peptide endoglycosidase F) Genzyme, Boston, Mass.] in 0.75 ml of 50 mM Tris-HCl, pH 7.0 at 37° C. for 30 minutes in a test tube. The control contained buffer but no endoglycosidase. At the end of the incubation period, 0.25 ml of detergent solution (1:125 dilution of a commercial liquid detergent composition which did not contain dyes, perfumes, enzymes or brighteners in 1M Tris-HCl, pH 7.5) containing 80 ug of subtilisin BPN'/ml was added to the control and enzyme containing samples and incubated for an additional 20 minutes. At the end of this treatment, the tubes were centrifuged and the protein content in the supernatants were determined by measuring absorbance at 280 nm. For each treatment, a reaction blank was prepared which contained no swatch during the assay. The blank values were subtracted from the absorbance of treated samples to determine the release of 280 nm absorbing material during incubation. Higher absorbance represents increased release of protein from fibers. The results are shown in Table III.

TABLE III

| Treatment | Absorbance at 280 nm | |
|---|---|---|
| | Blood Stain | Fecal Matter Stain |
| Control | 0.79 | 2.07 |
| Endo-D | 0.84 | 2.14 |
| Endo-H | 0.83 | 2.12 |
| N-Glycanase | 0.78 | 2.10 |

These results suggested that the endoglycosidases, Endo-D and Endo-H, in combination with the second enzyme subtilisin increased the release of 280 nm absorbing material from the blood stained swatches as compared to the control. In addition, Endo-D, Endo-H and N-glycanase all showed an increase in the release of 280 nm absorbing material from the fecal stained swatches.

EXAMPLE 2

Effect of Endo-H on Removal of Fecal Matter Stain

Figure 6A:
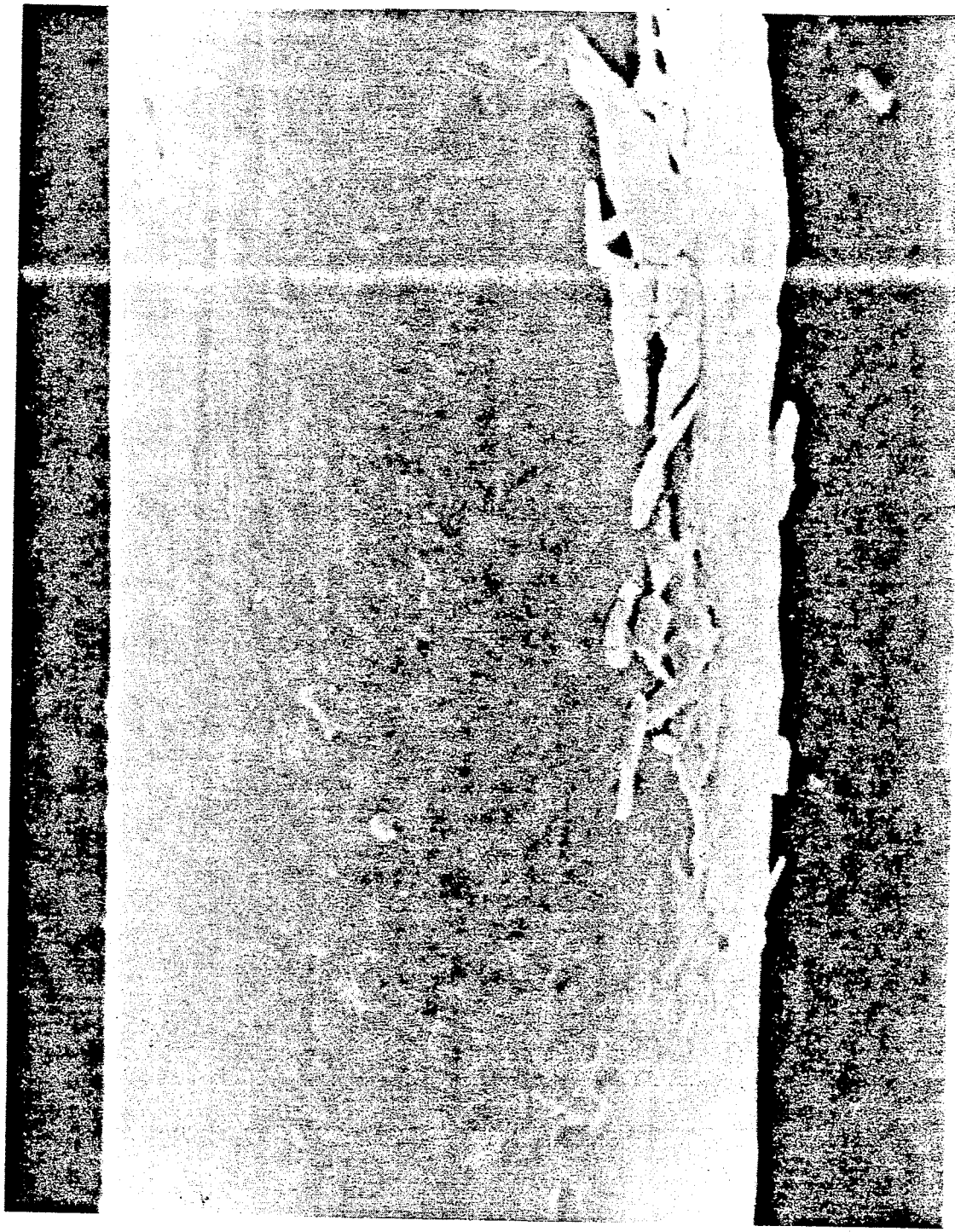
FIGS. 6A and 6B are electron micrographs (8100×) of nylon swatches stained with fecal matter and treated either with or without Endo-H.
Figure 6B:
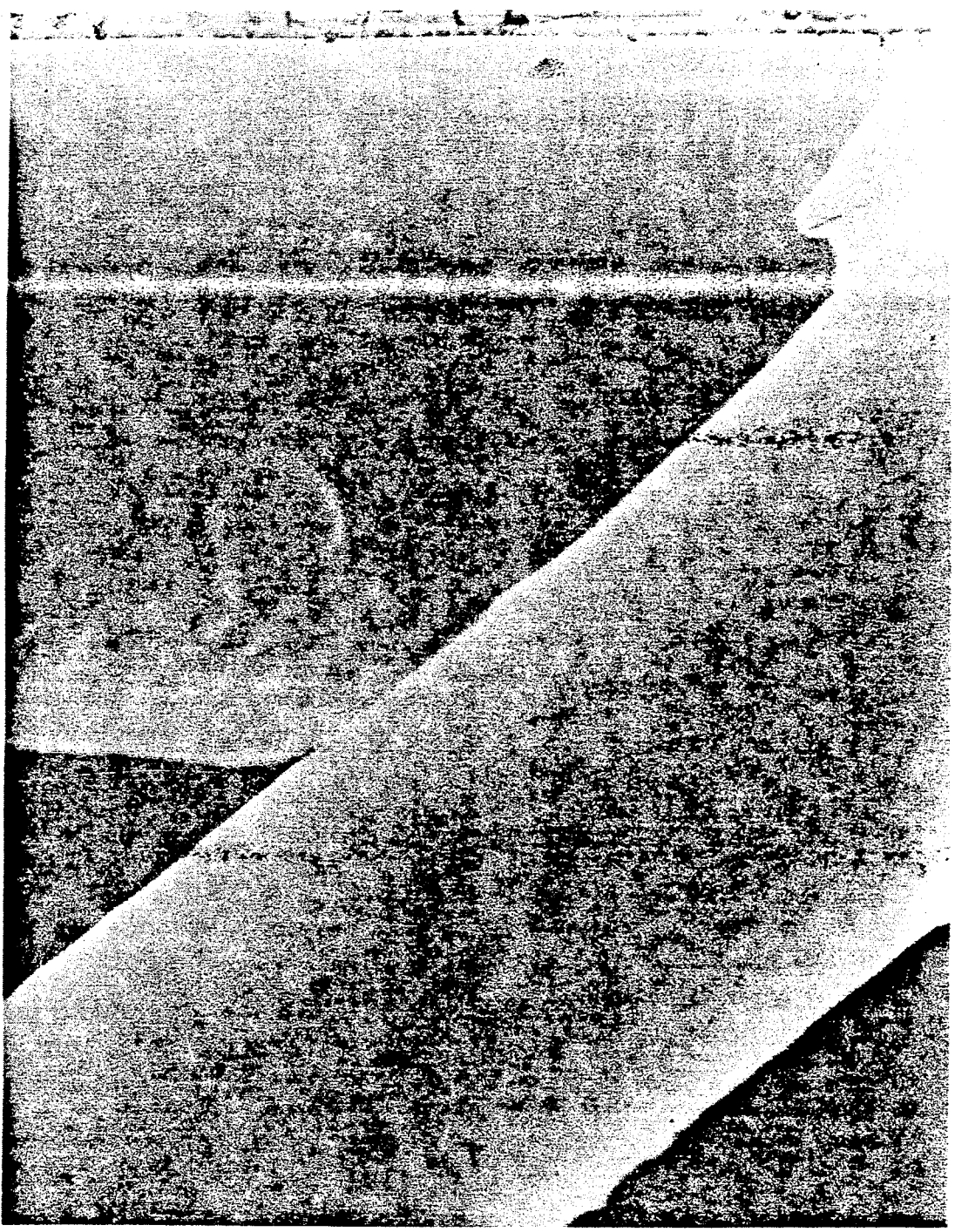

This example is similar to Example 1 but was performed by using fecal matter stained swatches made of nylon fabric. The swatches were washed in detergent solution, rinsed and dried. The detergent consisted of liquid commercial detergent which did not contain enzymes, brighteners, dyes or perfumes. One set of swatches was kept aside and referred as "untreated control". These swatches were treated the same as the sample swatches except that they were not treated with Endo-H. The sample swatches were incubated with 0.01 U Endo-H (Boehringer Mannheim Biochemical Catalog No. 752 967) in buffer (10 mM Na-acetate, pH 6.0) at 37° C. for 15 minutes. Then 0.25 ml of detergent solution (1:125 dilution in 1.0M Tris-HCl, pH 7.5) was added and incubated for an additional 15 minutes. At the end, tubes were centrifuged and the supernatants removed by suction. The swatches were air dried. Fibers from the swatches were examined by scanning electron microscopy following critical point drying. An electron micrograph of a detergent-washed swatch stained with fecal matter is shown in FIG. 6A. As can be seen, rod like bacteria and particulate matter are found on the surface of the fabric. FIG. 6B shows a swatch treated with Endo-H and detergent. This figure shows a smooth clean fabric which demonstrates that Endo-H and detergents facilitates the removal of particulate material and bacterial debris.

EXAMPLE 3

Effect of Endo-F on Fecal Matter Stain

Swatches stained with fecal matter (1 inch diameter) were washed in detergent solution, rinsed and dried. Swatches were cut into quarters and used in the following experiments.

A. Swatches were incubated in 1 ml 10 mM sodium-acetate buffer, pH 5.5 with or without Endo-F (Boehringer Mannheim Biochemical) (0.15 units) for 30 minutes at 37° C. The tubes were then centrifuged for eight minutes. Supernatants were removed and the absorbance of each was measured at 280 mm. Change in A280 was determined by subtracting appropriate blanks (see Example 1). Higher absorbance includes the increase in the amount of protein or material absorbing at 280 mm released from the swatches. For the controls, the average change in A280 was 0.93. For swatches treated with Endo-F the average change in A280 was 1.05. This indicated that Endo-F increases the efficiency of fecal stain removal.

B. Swatches were incubated in 0.75 10 mM sodium-acetate buffer pH 5.5 with or without Endo-F (0.15 units) for 15 minutes at 37° C. At the end of this treatment, 0.25 ml of detergent solution (in 0.1M Tris-HCl, pH 7.5) containing 10 µg of the protease subtilisin BPN' was added and the tubes were incubated at 37° C. for another 15 minutes. At the end, tubes were centrifuged, supernatants were removed and absorbance at 280 nm was measured. In the case of the control (no Endo-F), the average change in A280 was 1.08 whereas the sample treated with Endo-F showed a change in A280 of 1.36. This indicated that the effect of Endo-F was enhanced by the presence of the detergent.

C. An experiment similar to "B" was performed except the detergent solution contained 10 mM 2-mercaptoethanol instead of subtilisin. The average change in A280 for the control was 1.05 whereas the sample treated with Endo-F produced a change in A280 of 1.24. These results demonstrated the ability of Endo-F in the presence of disulfide cleaving reagents to remove fecal stains.

D. An experiment similar to "B" was performed except that the detergent solution contained 10 mM 2-mercaptoethanol and 10 µg subtilisin BPN'. The average change in A280 for the control was 1.14 whereas the Endo-F treated sample had a change in A280 of 1.29. These results indicate that Endo-F is capable of removing fecal matter in the presence of detergent, a protease and a disulfide cleaving reagent (2-mercaptoethanol).

EXAMPLE 4

Comparison of Endo-H with Other Enzymes

Figure 7A:
FIGS. 7A through 7H are electron micrographs (5000×) showing the effect of Endo-H and other carbohydrase enzymes on cotton swatches strained with fecal matter.
Figure 7B:
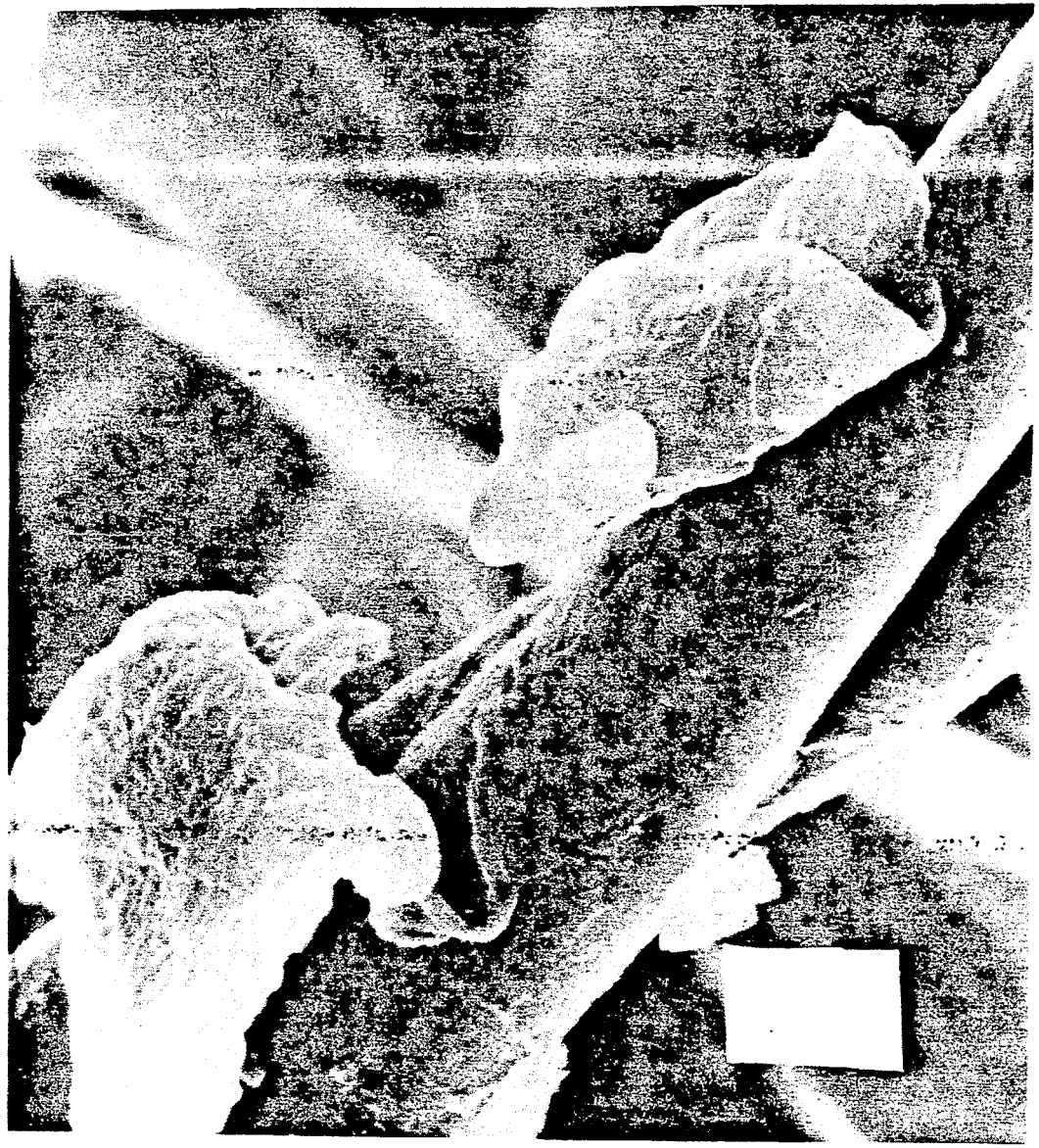
Figure 7C:
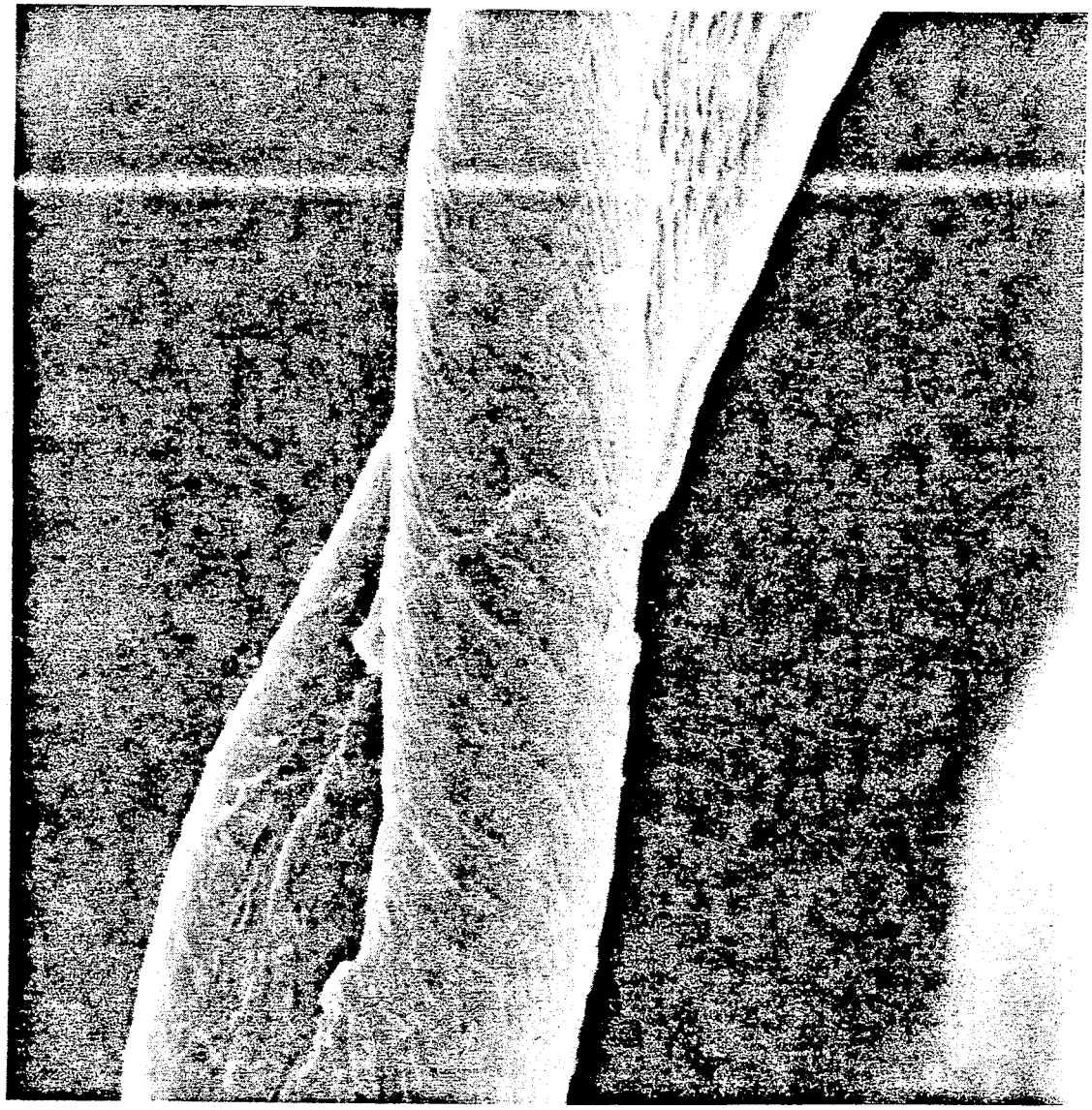
Figure 7D:
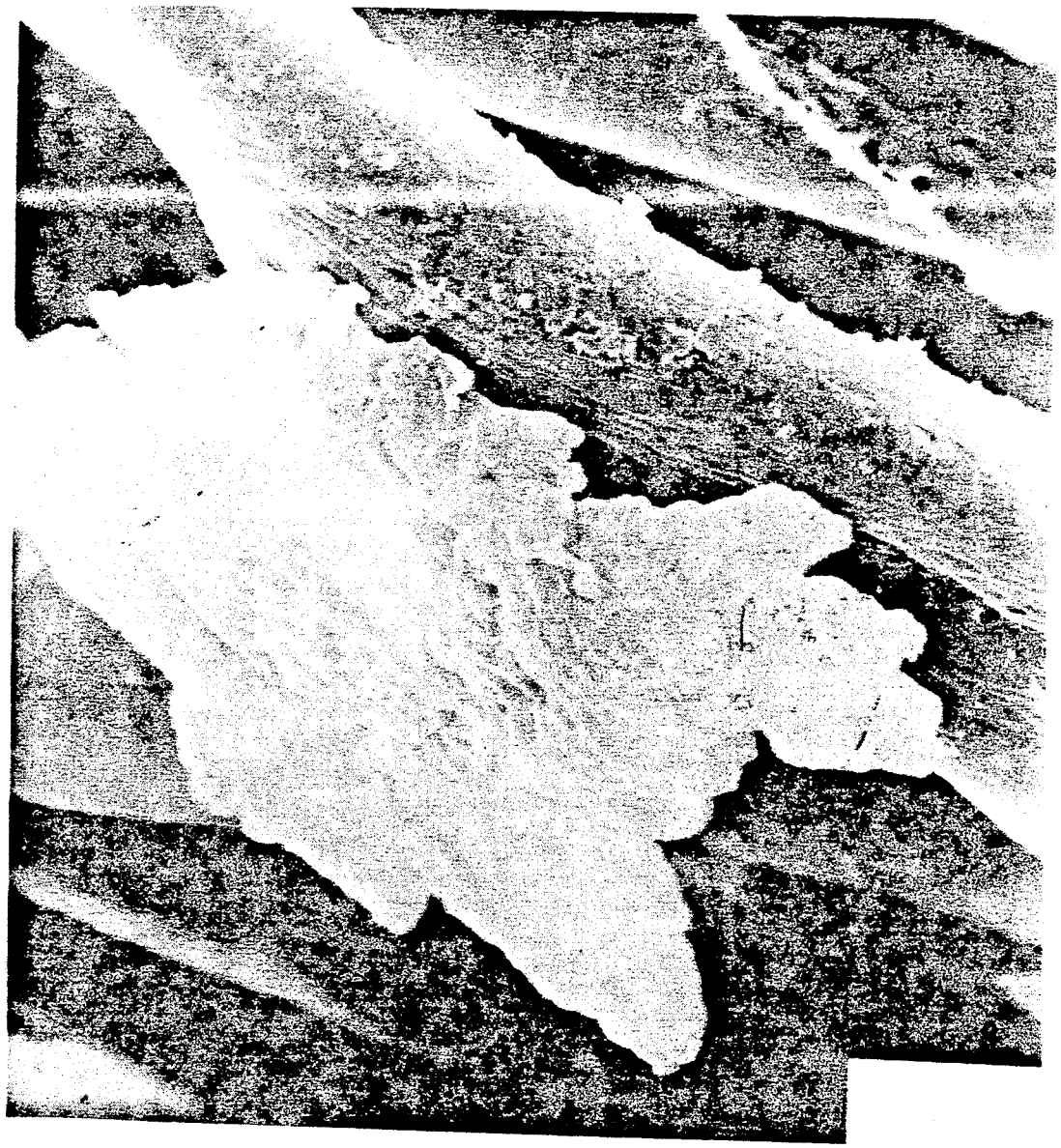
Figure 7E:
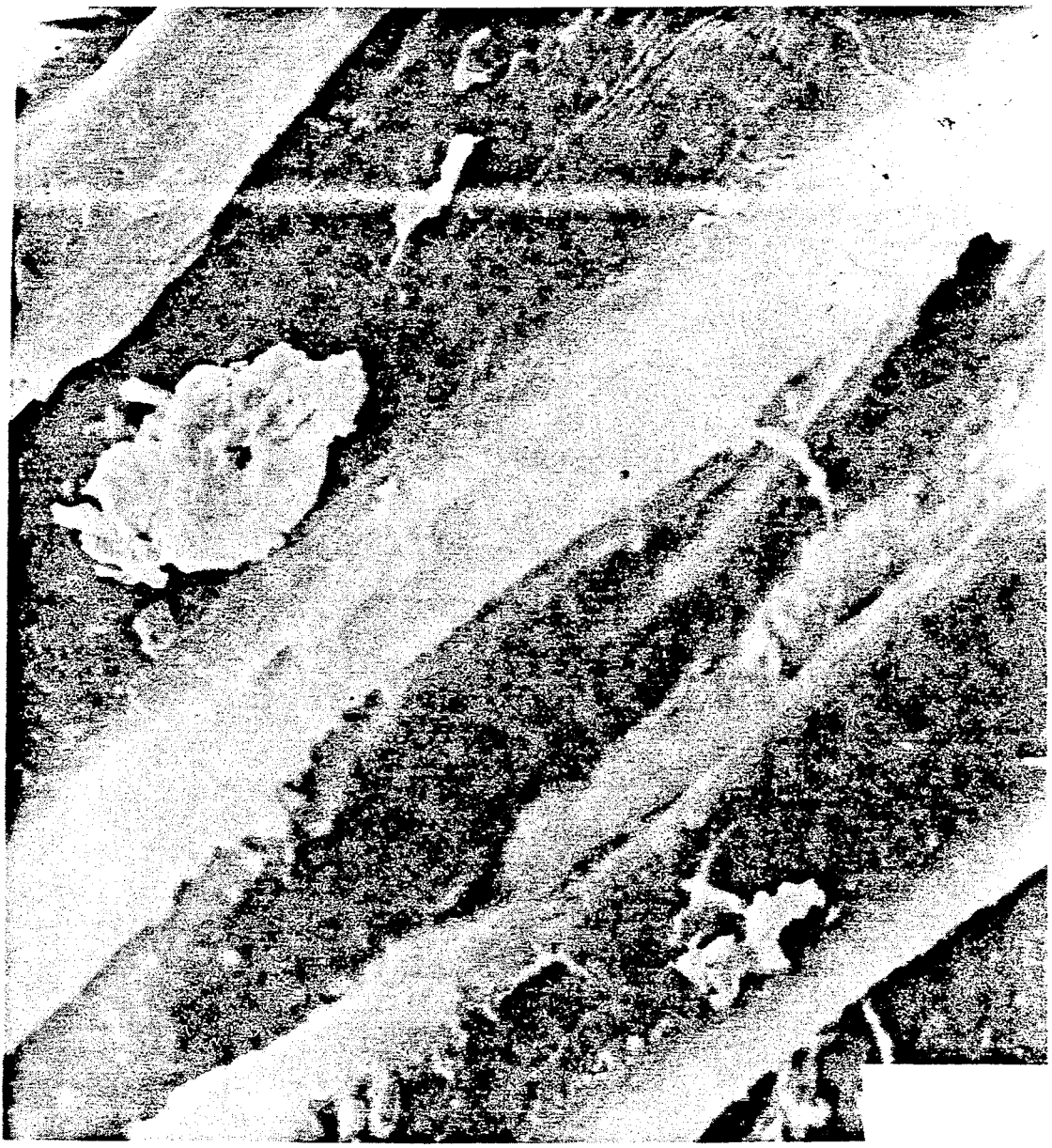
Figure 7F:
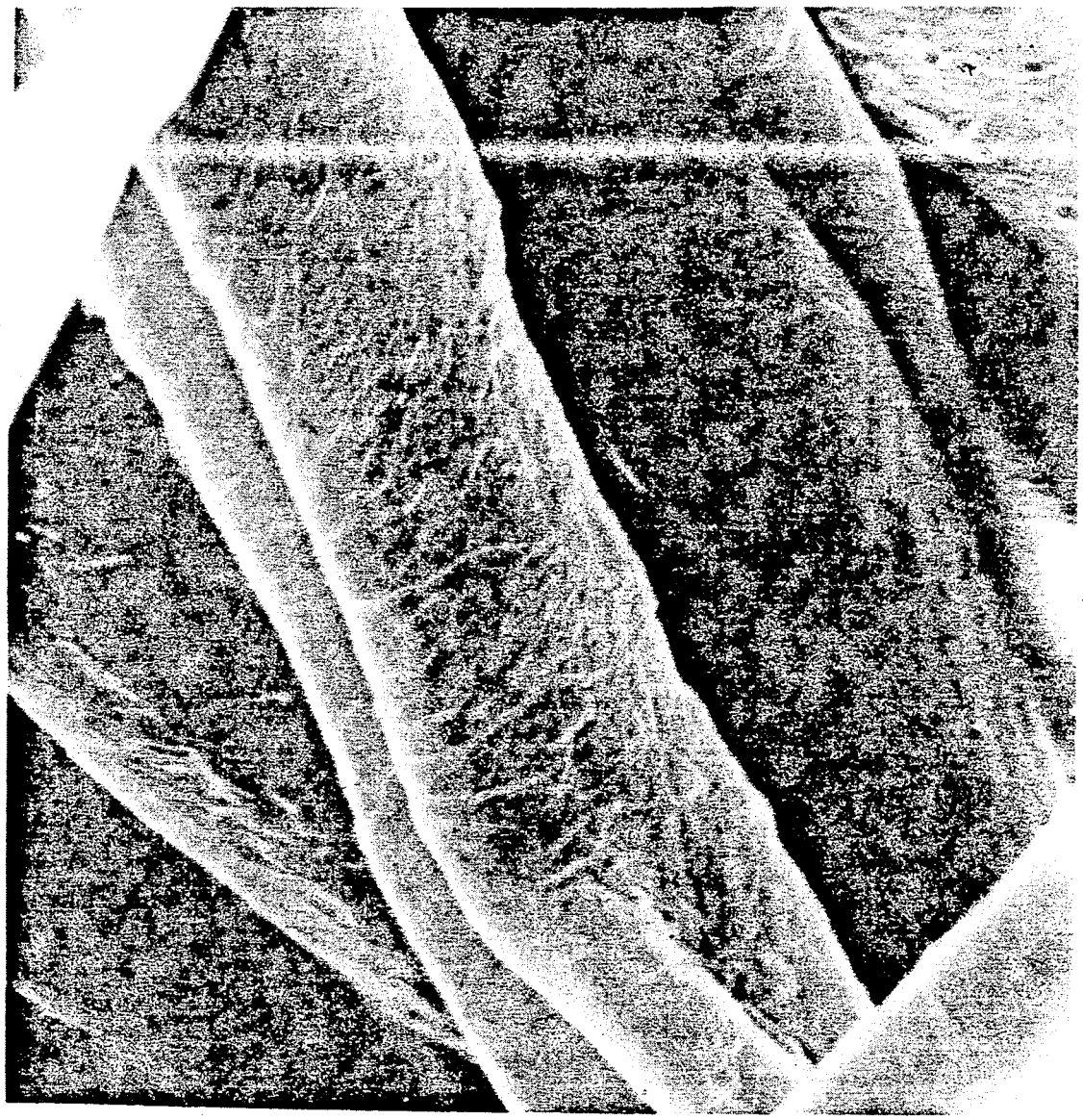
Figure 7G:
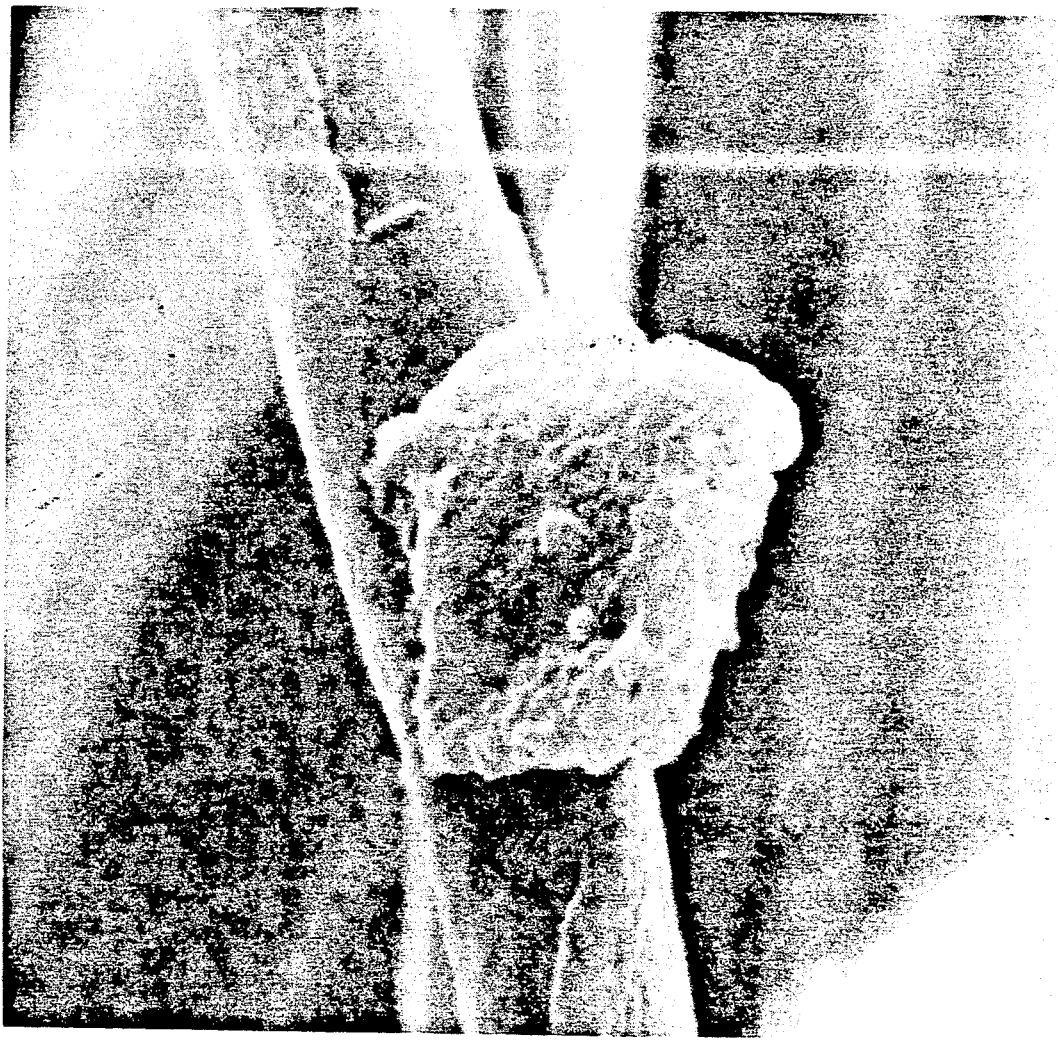
Figure 7H:
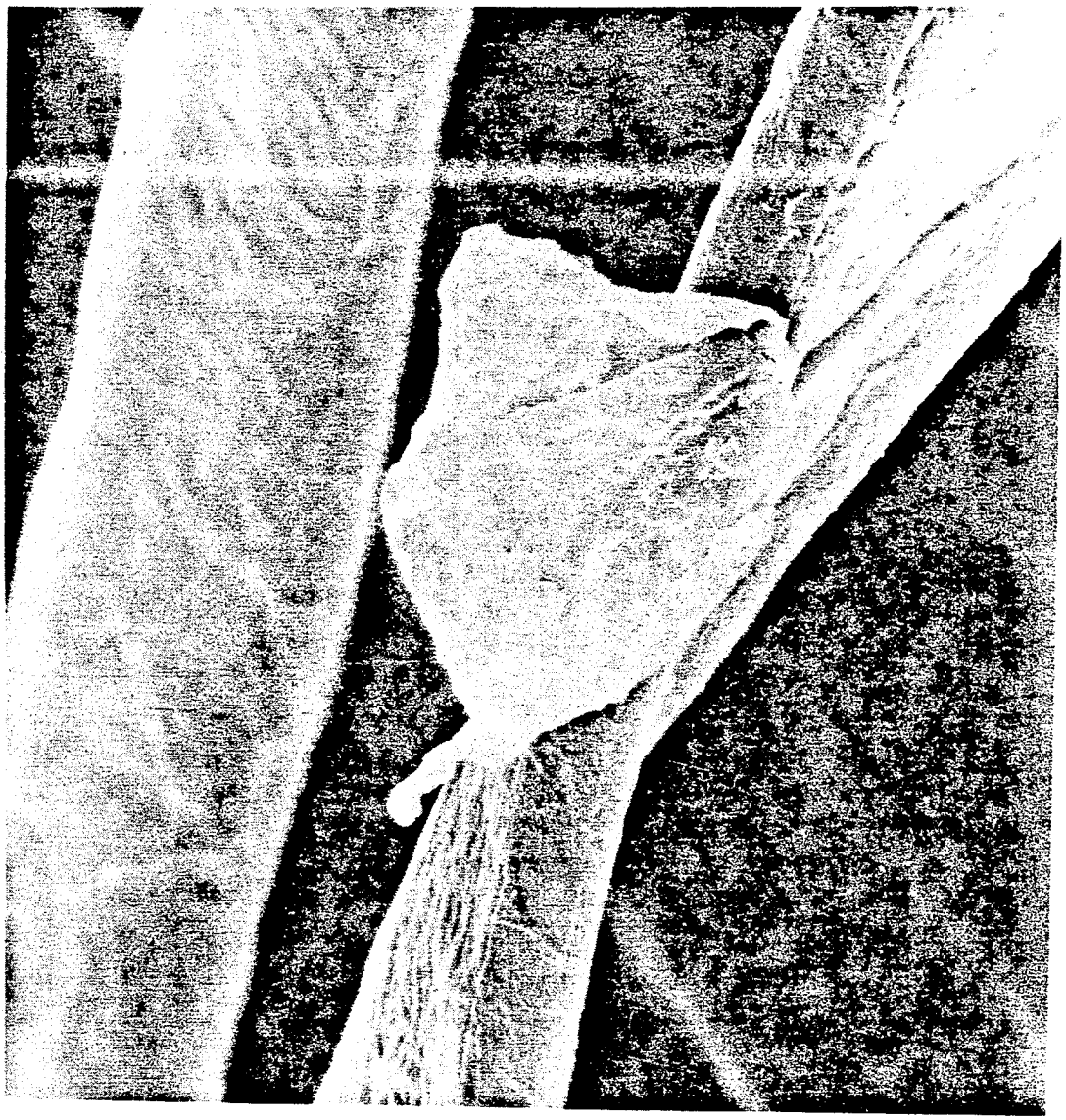

Experiments similar to those described in part B of Example 3 were repeated with Endo-H (Boehringer Mannheim Biochemical Catalog No. 100 119) and other carbohydrase enzymes except that no protease such as subtilisin was used. Changes in A280 were monitored and fibers were examined by scanning electron microscopy. Removal of particulate and bacterial debris from fabric was seen with Endo-H and "Lysing Enzymes" (a mix of proteases and glyconases obtained from Sigma Chemical Company). However, the enzymes, lysozyme, α-glycosidase, β-glucosidase and β-glucorinadase, showed little or no benefit. (Results not shown.) The results of electron microscopy for this experiment for treatment with or without the above enzymes are shown in FIGS. 7A through 7H. FIG. 7A is a control which was not treated with endoglycosidase. FIG. 7B is an electron micrograph of a swatch treated with lysozyme; FIG. 7C is a swatch treated with Endo-H; FIG. 7D is a swatch treated with α-glucosidase; FIG. 7E is a swatch treated with β-glucosidase; FIG. 7F is an electron micrograph of a fiber treated with "Lysing Enzymes"; FIG. 7G is an electron micrograph of a swatch treated with β-glucorinadase; and FIG. 7H is an electron micrograph of a swatch treated with chitinase. As can be seen, the swatch treated with Endo-H (FIG. 7C) has been thoroughly cleansed of the fecal matter stain. Similar results were obtained for the swatches treated with "Lysing Enzymes" as shown in FIG. 7F.

EXAMPLE 5

Removal of Bacteria from a Solid Surface

To test the effect of Endo-H on removal of bacteria from solid surfaces (glass), the following protocol was used. Trypticase soy broth (TSB) (10 ml) was inoculated with a microbial species (*Staphylococcus aureus* ATCC culture #6538 or *Escherichia coli* ATCC culture #10536) from a stock culture slant and incubated overnight at 37° C. A suspension of about $10^8$ cells/ml TSB was prepared and 100 μl of this suspension was placed within the etched ring on a glass slide. Each slide was incubated for 5 minutes at 37° C. in a dry incubator oven after which excess microbial solution was tapped off. The slides were then rinsed with 100 μl of sterile distilled water. The excess solution and loose organisms were then tapped off.

After the bacteria were adhered to the glass slides (2 or more hours at 37° C.), 100 μl of the following solutions were applied to separate slides: (a) 10 mM acetate buffer, pH 5.5, (b) 10 mM acetate buffer, pH 5.5+1 ppm Endo-H (Boehringer Mannheim Biochemical Catalog No. 100 119), (c) detergent solution, (d) detergent solution+1 ppm Endo-H. A set of slides were kept aside as untreated controls and were not treated with any solutions. The noncontrol slides were then incubated for 15 minutes at 37° C. At the end of the incubation, the solutions were tapped off. The slides were then rinsed with 100 μl of sterile distilled water and air dried at room temperature. The bacteria which remained after this treatment were heat fixed and stained by a standard Gram staining method. The slides were then examined by a light microscope (bright field illumination, 125× magnification) and the number of organisms/field was determined. Twenty fields were counted for each slide from which the average organisms/field was calculated.

The following results were obtained:

A. For *Staphylococcus aureus*

| | |
|---|---|
| i) No treatment | >100 organisms/field |
| ii) Buffer | >100 organisms/field |
| iii) Buffer + Endo-H | <10 organisms/field |
| iv) Detergent solution | >100 organisms/field |
| v) Detergent + Endo-H | <10 organisms/field |

These results indicate that Endo-H buffer alone or in combination with detergent reduced the number of S. aureus bacteria retained on the glass slides 10 fold as compared to treatment with detergent alone.

B. For *Escherichia coli*

| | |
|---|---|
| i) No treatment | >100 organisms/field |
| ii) Buffer | >100 organisms/field |
| iii) Buffer + Endo H | >100 organisms/field |
| iv) Detergent | >100 organisms/field |
| v) Detergent + Endo H | <10 organisms/field |

These results indicate that Endo-H in combination with a detergent reduced the number of *E. coli* retained on the glass slide 10-fold as compared to treatment with detergent alone.

EXAMPLE 6

Removal of Bacteria from a Solid Surface

An experiment similar to Example 5 was performed with two slime-producing *Staphylococcus aureus* cultures (determined by their abilities to bind to polystyrene tubes). Microscope slides were modified by forming two rings (≈1.7 cm diameter) with nail polish. Overnight culture of the organisms were diluted 1:10 with 1% peptone solution. Diluted culture (100 μl) was put in rings. Slides were put in 150 cm petri dishes and incubated at 37° C. After two hours incubation, slides were rinsed with distilled water and treated with three different conditions (A. Na-acetate buffer, B. detergent, and C. detergent plus 1 μg Endo-H/ml) as in Example 5. The Endo-H was obtained from *E. coli* transformed to produce Endo-H from *S. plicatus*. At end of 15 minutes, incubation slides were rinsed with distilled water and Gram stained. The number of bacteria was counted under microscope per 100× field for 20 fields. The results are expressed as the average number of cells per field.

| | Condition | Culture I | Culture II |
|---|---|---|---|
| A. | Control | 23 | 202 |
| B. | Detergent | 9 | 58 |
| C. | Detergent + Endo-H | 2 | 33 |

EXAMPLE 7

Removal of Bacteria from a Cloth Surface

To test the effect of Endo-H on the removal of bacteria from a cloth surface, the following protocol was used. *Staphylococcus aureus* (ATCC 6538) and *Staphylococcus epidermidis* (ATCC 155) were separately cultured in 5 ml of Luria's broth and allowed to grow at 37° C. for 12 hours. The cultures were then added to 30 ml of 0.2M NaCitrate, pH 5.5 buffer at about $10^3$ cells/ml, in two 100 ml shake flasks. Twelve cloth swatches (0.5×0.5 inch cotton swatches) were also added to the flasks after inoculation. After incubation at 37° C. for two hours with gentle rotation (150 rpm), the swatches were transferred to sterile tubes and washed 3× with buffer comprising 200 mM NaCitrate, pH 5.5 which had been previously sterilized by 0.22 micron filtration. Six swatches were then added to a shake flask containing 0.5 mg/ml Endo-H in 30 ml citrate buffer, and six swatches were added to a shake flask containing only citrate buffer as the control. The Endo-H was obtained from *E. coli* producing *S. plicatus* Endo-H. After incubation at 37° C. for 1.5 hours with gentle rotation (100 rpm), the swatches were transferred to sterile tubes and washed as previously described. Swatches were then plated carefully on trypticase soy agar plates and overlaid with enough liquid trypticase soy agar to cover the swatches. After the plates were dry, they were incubated at 37° C. for 18 hours, and colonies of *Staphylococcus aureus* and *Staphylococcus epidermidis* on the cloth surface were counted using a dissecting scope.

The following results were obtained:

A. For *Staphylococcus aureus*

| | |
|---|---|
| Control | 103 +/− 24 colonies per swatch |

| | |
|---|---|
| Endo-H | 53 +/− 18 colonies per swatch |

49% decrease in bacterial colonies by Endo-H treatment

B. For *Staphylococcus epidermidis*

| | |
|---|---|
| Control | 57 +/− 11 colonies per swatch |
| Endo-H | 16 +/− 10 colonies per swatch |

72% decrease in bacterial colonies by Endo-H treatment.

These results indicate that Endo-H treatment significantly reduces the number of bacteria adhered to a cloth surface.

EXAMPLE 8

Binding of Endo-H to Bacteria

The following experiment was conducted to determine if the Type II endoglycosidase, Endo-H, interacts with a surface component on the bacteria *Staphylococcus aureus* and *Streptococcus mutans*. Such an interaction was detected. Although not completely characterized herein, this interaction was not previously known and may form the basis of the above described ability of Endo-H to remove such bacteria from a surface.

Endo-H from transformed *E. coli* and purified by modifying the methods described by Trimble R. J. et al. (1985), *J. Biol. Chem.*, 260, 5638–5690, was labelled with biotin according to the procedure described by Updyke, T. V. and Nicolson, G. L. (1986), *Methods in Enzymology*, 121, 717–725. After such labelling, the Endo-H retained most of its reactivity with the glycoprotein ovalbumin.

Overnight cultures of *Staphylococcus aureus* (ATCC 6538) grown in Luria's broth, and *Streptococcus mutans* (ATCC 27607) grown in Difco Brain Heart Infusion media, were centrifuged and washed three times with 200 mM NaCitrate pH 5.5 buffer and suspended in the same buffer to a concentration of about $10^9$ cells/ml. Aliquots of 0.5 ml were placed in 31.5 ml Eppendorf tubes and incubated under various conditions and times.

| Tube | Cells | 2% BSA | Biotinylated Endo-H | 0.2M NaCitrate pH 5.5 | Incubation Time (min.) |
|---|---|---|---|---|---|
| 1 | 0.5 ml | 5 μl | — | 0.5 ml | 30 |
| 2 | 0.5 ml | — | 5 μl | 0.5 ml | 2 |
| 3 | 0.5 ml | — | 5 μl | 0.5 ml | 30 |

Incubation was done at room temperature using a slow speed rocker for either two or 30 minutes. BSA (bovine serum albumin), diluted in tris-buffered saline was used as a control solution in order to prevent any non-specific protein binding to the cells. After incubation, the tubes were centrifuged and the supernatants were discarded. Two cell washes with 2% BSA solution were done by adding 1.0 ml BSA to the cells, vortexing well, centrifuging and discarding the supernatant. To the washed cells, 0.5 ml of streptavidin-HRP (streptavidin-labeled horse radish peroxidase, Kirkegaard and Perry Laboratories, Inc.) was used and incubated for 30 minutes at room temperature. The tubes were again centrifuged and washed as previously described. Detection of Endo-H binding to the bacterial cells was determined by the detection of HRP-streptavidin, which will bind very tightly to the biotinylated Endo-H bound to the cells. HRP detection was determined by adding 0.5 ml of the HRP substrate OPD (O-phenylenediamine) diluted in citrate phosphate buffer solution containing hydrogen peroxide. The chromogen generation was quenched with 2M $H_2SO_4$ one minute after adding OPD. The cells were centrifuged and the supernatant was read at 490 nm The following results were obtained:

| | OD 490 nm |
|---|---|
| For *Staphylococcus Aureus* | |
| Control | 0.13 |
| Endo-H, 2 minutes | 1.89 |
| Endo-H, 30 minutes | 1.90 |
| For *Streptococcus mutans* | |
| Control | 0.18 |
| Endo-H, 2 minutes | 3.76 |
| Endo-H, 30 minutes | 3.80 |

These results indicate that there is binding of Endo-H to the bacteria *Staphylococcus aureus* and *Streptococcus mutans*. The data show that the majority of Endo-H that binds occurs in the first two minutes or less after contact with the cells. The higher absorbance obtained with *Streptococcus mutans* may indicate a higher level of Endo-H binding.

EXAMPLE 9

A heavy duty liquid laundry detergent composition of the present invention is as follows:

| Component | Active Weight % |
|---|---|
| $C_{13}$ linear alkylbenzene sulfonic acid | 8.00 |
| $C_{14-15}$ alkyl polyethoxylate (2.25) sulfonic acid | 12.00 |
| 1,2 propanediol | 3.50 |
| Sodium diethylenetriamine pentaacetate | 0.30 |
| Monoethanolamine | 2.00 |
| $C_{12-13}$ alcohol polyethoxylate (6.5)* | 5.00 |
| Ethanol | 8.50 |
| Potassium hydroxide | 1.80 |
| Sodium hydroxide | 3.85 |
| $C_{12-14}$ fatty acid | 10.00 |
| Citric acid | 4.00 |
| Calcium formate | 0.12 |
| Sodium formate | 0.86 |
| $C_{12}$ alkyltrimethylammonium chloride | 0.50 |
| Tetraethylene pentamine ethoxylate (15-18) | 2.00 |
| Water | 35.12 |
| Dye | 0.08 |
| Perfume | 0.25 |
| Protease** | 0.125 |
| Endoglycosidase H | 2000 ppm |

Notes
*Alcohol and monoethoxylated alcohol removed.
**mg active enzyme/g (@34 mg active enzyme/g stock)

The ingredients listed above are added to a mixing tank with a single agitator in the order in which they appear. Before the protease enzyme, dye and perfume are added, the pH of the mix is adjusted so that a 10% by weight solution in water at 20° C. has a pH of about 8.5.

This composition provides superior cleaning of carbohydrate-containing stains, even compared to protease-containing and/or amylase-containing detergents.

EXAMPLE 10

A heavy duty liquid laundry detergent composition of the present invention is as follows:

| Component | Active Weight % |
|---|---|
| $C_{13}$ linear alkylbenzene sulfonic acid | 8.00 |
| $C_{14-15}$ alkyl polyethoxylate (2.25) sulfonic acid | 12.00 |
| 1,2 Propanediol | 3.50 |
| Sodium diethylenetriamine pentaacetate | 0.30 |
| Monoethanolamine | 2.00 |
| $C_{12-13}$ alcohol polyethoxylate (6.5)* | 5.00 |
| Ethanol | 8.50 |
| Potassium hydroxide | 1.80 |
| Sodium hydroxide | 3.85 |
| $C_{12-14}$ fatty acid | 10.00 |
| Citric acid | 4.00 |
| Calcium formate | 0.12 |
| Sodium formate | 0.86 |
| $C_{12}$ alkyltrimethylammonium chloride | 0.50 |
| Tetraethylene pentamine ethoxylate (15-18) | 2.00 |
| Water | 37.12 |
| Dye | 0.08 |
| Perfume | 0.25 |
| Protease** | 0.125 |
| Endoglycosidase H | 125 ppm |

Notes
*Alcohol and monoethoxylated alcohol removed.
**mg active enzyme/g (@34 mg active enzyme/g stock)

The ingredients listed above are added to a mixing tank with a single agitator in the order in which they appear. Before the protease enzyme, dye and perfume are added, the pH of the mix is adjusted so that a 10% by weight solution in water at 20° C. has a pH of about 8.5.

This composition provides superior cleaning of carbohydrate-containing stains, particularly fecal stains.

Other compositions of the present invention are obtained when the Endo H level is reduced to 0.40 mg/ml, water is decreased to 35.72, and 1% Irgasan (a Ciba-Geigy antibacterial) is added.

EXAMPLE 11

A liquid soap composition of the present invention is as follows:

| Component | Active Weight % |
|---|---|
| Ammonium lauryl sulfate | 6.0 |
| Sodium lauryl sarcosinate | 5.7 |
| Cocamidopropyl betaine | 6.3 |
| Coconut fatty acid | 1.0 |
| Quaternary amine | 0.3 |
| Ethylenediamine tetraacetic acid | 0.2 |
| Ammonium sulfate | 0.4 |
| Perfume | 0.25 |
| Kathon | 5 ppm |
| Water | 72.0 |
| Endoglycosidase H | 1000 ppm |
| Triclocarban | 1.50 |

The ingredients listed above are added to a mixing tank with a single agitator in the order in which they appear below.

This composition provides antibacterial action for removal of common skin flora, even when compared to non-glycosidase containing, antibacterial soaps.

EXAMPLE 12

A hard surface scouring cleanser of the present invention is as follows:

| Component | Weight % |
|---|---|
| False Body Fluid Phase (Specific Gravity 1.1) | 93.5 |
| Barasum NAS-100 (Sodium saponite clay) | 4.25 |
| Tetrapotassium pyrophosphate | 6.00 |
| Tripotassium phosphate | 2.00 |
| Sodium hypochlorite bleach | 0.90 |
| Sodium lauryl alkyl sulfate Surfactant | 0.25 |
| Dye and Perfume | 0.26 |
| Endoglycosidase H | 1000 ppm |
| Soft Water | 78.86 |
| Abrasive (Expanded Perlite-Specific Gravity 2.0 Average Particle Diameter 50 microns) | 5.0 |
| Hercoflat 135 Filler (powdered polypro-pylene, Specific Gravity 0.9 Average Particle Diameter 35 microns) | 1.50 |
| Ratio Average Particle Diameter Abrasive/Filler = 1.43:1 | |

The composition is prepared by mixing tetrapotassium pyrophosphate, tripotassium phosphate, sodium saponite clay, dye, perfume and deionized water using relatively high shear agitation to the extent necessary to form a false body fluid phase. The alkyl sulfate surfactant is then blended into this mixture followed by the polypropylene filler material. A separate aqueous slurry of sodium hypochlorite and perlite abrasive is prepared and then blended into the false body fluid phase while it is being liquified under moderate shear agitation. The resulting scouring composition is false bodied, i.e., gel-like in its quiescent state but easily fluidized by application of shear stress. Such a composition is especially effective for removal of stains and soil from hard surfaces.

EXAMPLE 13

A shampoo composition of the present invention is as follows:

| Component | Level |
|---|---|
| Ammonium alkyl sulfate (29% Aqueous solution) | 55.25% |
| Zinc pyridinethione crystals of Ex. I of U.S. Pat. No. 4,345,080 | 2.0 |
| Coconut monoethanolamide | 3.0 |
| Ethylene glycol distearate | 5.0 |
| Sodium citrate | 0.5 |
| Citric acid | 0.2 |
| Color solution | 0.1 |
| Perfume | 0.5 |
| Endoglycosidase H | 1000 ppm |
| Water | q.s. 100.00% |

EXAMPLE 14

An antiperspirant stick of the present invention is made utilizing the following components:

| Component | Level |
|---|---|
| Cyclomethicone | 42.55 |
| Fluid AP | 4.99 |
| Stearyl alcohol | 11.49 |
| Castor wax | 4.99 |
| Talc | 6.99 |

| Component | Level |
| --- | --- |
| Zirconium/aluminum/glycine complex | 26.67 |
| Fragrance masking agent | 0.80 |
| $C_{20}$ alcohol | 0.12 |
| Pyridoxal phosphate | 1.00 |
| Endoglycosidase H | 500 ppm |

EXAMPLE 15

A liquid soap composition of the present invention is as follows:

| Component | Active Weight % |
| --- | --- |
| Ammonium lauryl sulfate | 6.0 |
| Sodium alkyl sarcosinate | 5.7 |
| Cocamidopropyl betaine | 6.3 |
| Coconut fatty acid | 1.0 |
| Ethylenediamine tetraacetic acid | 0.2 |
| Ammonium sulfate | 0.4 |
| Perfume | 0.25 |
| Dye | 5 ppm |
| Water | 80.15 |
| Endo-H | 50 ppm |
| 2,4,4'-trichloro-2'-hydroxydiphenyl ether | 100 ppm |

The ingredients listed above are added to a mixing tank with a single agitator in the order in which they appear above. Before the dye and perfume are added, the pH of the mix is adjusted so that a 10% by weight solution in water at 20° C. has a pH of about 6.5.

This composition provides antibacterial action for the removal of common skin flora.

EXAMPLE 16

A hard surface cleanser of the present invention is as follows:

| Component | Active Weight % |
| --- | --- |
| Sodium lauryl alkyl sulfate | 0.5 |
| Sodium alkyl sulfate | 0.5 |
| Butyl carbitol | 4.0 |
| Sodium bicarbonate | 0.5 |
| Citric acid | 0.04 |
| Formaldehyde | 0.03 |
| Perfume | 0.05 |
| Tartrate mono/disuccinate | 5.0 |
| Endo-H | 1000 ppm |
| Water | 88.4 |

The ingredients listed above are added to a mixing tank with a single agitator in the order in which they appear above. Before the perfume is added, the pH of the mix is adjusted so that a 10% by weight solution in water at 20° C. has a pH of about 7.

This composition is effective for the removal of soap scum and mold from hard surfaces, and is more efficacious than a cleanser without the endoglycosidase.

EXAMPLE 17

A composition used for the cleaning and/or preservation of whole fruit, vegetables or other plant surfaces is as follows:

| Component | Active Weight % |
| --- | --- |
| Water | 96.4 |
| $C_{12-13}$ alcohol polyethoxylate (6.5) | 0.1 |
| Endo-H | 3500 ppm |

This composition is prepared by mixing the alcohol polyethoxylate and Endo-H in water at their respective levels and adjusting the final pH to between 6–7. The final composition, when sprayed on plant surfaces such as whole fruit or vegetables, is useful in preventing microbial growth on said surfaces.

EXAMPLE 18

Potentiation of Bacteriocidal Effect of Antimicrobial by Endo-H

An overnight culture of *Escherichia coli* was diluted into fresh nutrient broth and grown for four hours at 37° C. Cells were obtained by centrifugation and washed in 0.2M Na-citrate buffer (SCB) pH 5.5. After centrifuging, cells were resuspended in SCB. The following tubes (in duplicate) were prepared:

| Condition | 1000 ppm Endo-H | 5000 ppm Chlorhexidine | SCB | Water |
| --- | --- | --- | --- | --- |
| Control | 0 µl | 0 µl | 200 µl | 10 µl |
| Chlorhexidine | 0 µl | 10 µl | 200 µl | 10 µl |
| Endo-H | 200 µl | 0 µl | 0 µl | 10 µl |
| Endo-H + Chlorhexidine | 200 µl | 10 µl | 0 µl | 0 µl |

The Endo-H was from *E. coli* producing *S. plicatus* Endo-H. To each tube, 790 µl of cell suspension added (final volume now 1 ml) and 10 µl samples were taken out as a 0 min control. Tubes were incubated at 37° C., on a rotary shaker and 10 µl samples were removed at 1 and 3 hours. The 10 µl aliquots were mixed with 990 µl of PBS (Phosphate buffered saline) ($10^{-2}$ dilution) and diluted further sequentially (1:10) in PBS (100 µl in 900 µl of PBS). 10 µl of each diluted solution was plated on Luria-Bertani agar plates. The plates were incubated at 37° C. overnight and colonies were counted. Number of colony forming bacteria in tubes were calculated according to dilutions made and the logarithm of this number used for further graphs and calculations.

| Condition | 0 minute Control | 1 hour (log kill) | 3 hours (log kill) |
| --- | --- | --- | --- |
| Control | 8.62 | 8.57 (.05) | 8.53 (.09) |
| 200 ppm Endo-H | 8.64 | 8.55 (.09) | 8.55 (.09) |
| 50 ppm Chlorhexidine | 8.60 | 4.42 (4.15) | 2.44 (6.59) |
| 200 ppm Endo-H + Chlorhexidine | 8.61 | 2.40 (6.17) | 2.00 (>6.53) |

Figure 8:
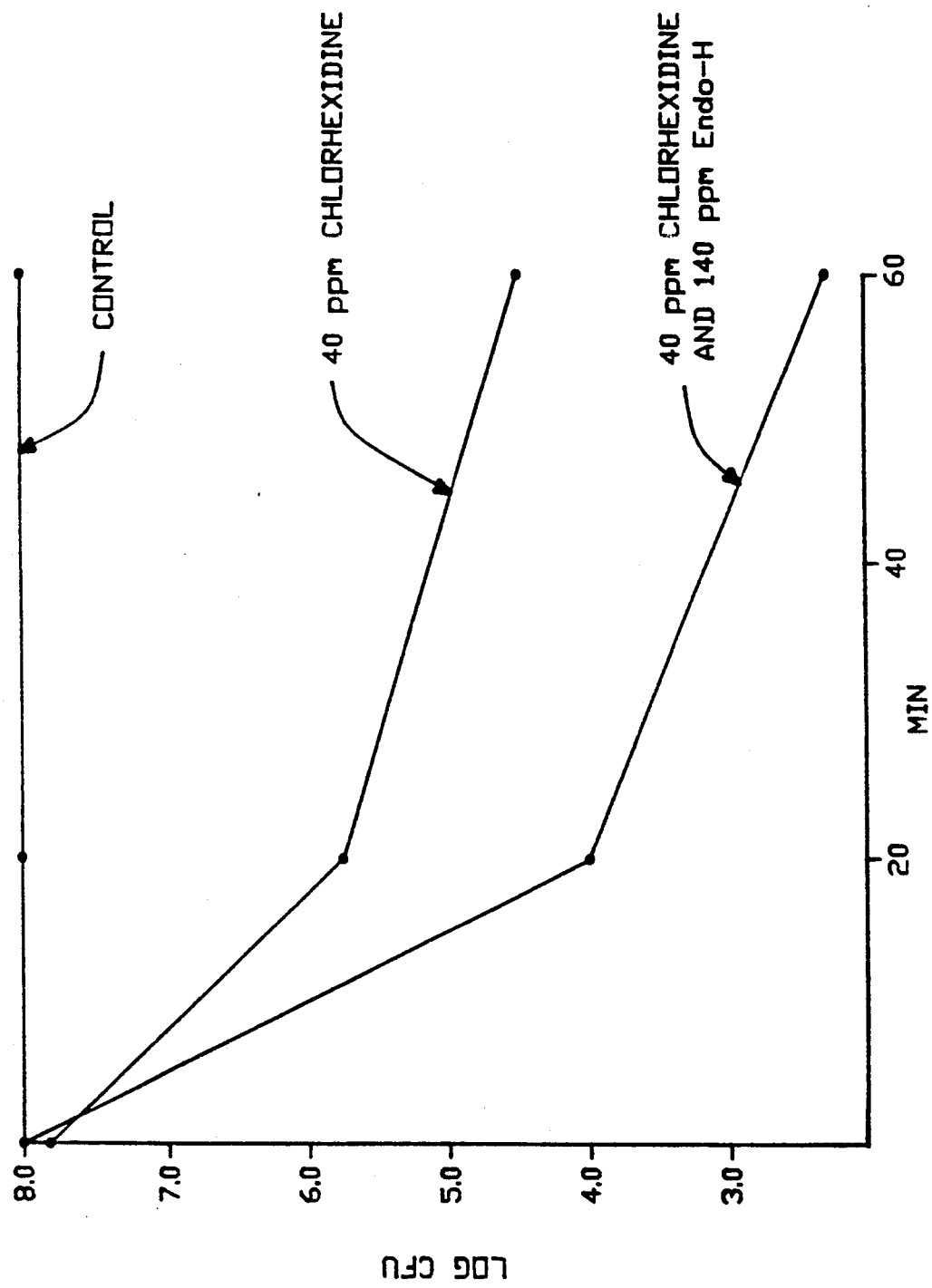

These results are plotted in FIG. 8. As can be seen, 200 ppm Endo-H enhances the bacteriocidal effect of 50 ppm chlorhexidine.

Similar results were obtained for slightly different concentrations of chlorhexidine and Endo-H as measured over a one hour time period. These results are depicted in FIG. 9. As can be seen, 140 ppm of Endo-H enhances the efficacy of 40 ppm chlorhexidine.

To further investigate this effect, a similar experiment was conducted using 20 ppm chlorhexidine (final concentration) with varying concentrations of Endo-H.

The results are shown in FIGS. 10A and 10B. These plots represent the change in the log of colony forming units (CFU). As can be seen, a relatively linear relationship exists between the amount of Endo-H added through about 280 ppm Endo-H. Further increases in Endo-H concentration enhance the adverse effect on bacterial viability through at least 1000 ppm Endo-H in combination with 20 ppm chlorhexidine.

EXAMPLE 19

Effect of Endo-H Alone and in Combination with Antimicrobial on Viability of Fungi A log phase culture of *Candida albicans* was grown, diluted into fresh growth medium, and treated with 0, 1, 10, 100 and 1000 ppm Endo-H (final concentration) for 4 hours while incubating with agitation at 37° C. The Endo-H was from *Bacillus subtilis* transformed to produce Endo-H from *S. plicatus*. One, ten and one hundred fold dilutions were made and plated to give viable cell counts. Zero through 10 ppm Endo-H did not significantly reduce cell viability, although in one case 10 ppm Endo-H reduced viability by about 36% after 18 hours of incubation. However, 100 ppm to 1000 ppm Endo-H reduced the number of viable cells recovered by about 50% to 88%, respectively, compared to the control not treated with Endo-H when treated for four hours.

In a separate experiment, a culture of *Candida albicans* was grown, diluted into fresh medium, and treated with 2.5 µg/ml Nystatin ® in addition to either 0, 1, 10, 100 or 1000 ppm Endo-H (final concentration) for 18 hours, while incubating with agitation at 37° C. One, ten, one hundred and one thousand fold dilutions were made and plated to give viable cell counts. Endo-H reduced viable cells recovered as follows as compared to that obtained with Nystatin ® alone:

| ppm Endo-H | % Reduction |
|---|---|
| 0 | 0% |
| 1 ppm | 69% |
| 10 ppm | 93% |
| 100 ppm | 99% |

As can be seen, as little as 1 ppm Endo-H significantly enhances the mycocidal effect of Nystatin ® whereas 10 ppm and 100 ppm Endo-H kill almost all of the fungi surviving Nystatin ® treatment alone.

A similar experiment was conducted using Amphotericin B ® at a concentration of 0.5 micrograms per ml for three hours. The results were as follows:

| ppm Endo-H | % reduction in viability |
|---|---|
| 0 | 0 |
| 1 | 17% |
| 10 | 5% |
| 100 | 96% |
| 1000 | 94% |

As can be seen, 100 ppm of Endo-H enhances the mycocidal effect of Amphotericin B ®.

EXAMPLE 20

Antimicrobial Effect of Endo-H Alone or in Combination with a Lysozyme

A 48-hour subculture of *E. coli* (ATCC 31617) was used to test the effect of the lysozyme mutanolysin (Sigma Chemical Co.) alone or in combination with detergent and/or Endo-H. The Endo-H was from *E. coli* transformed to produce Endo-H from *S. plicatus*. The following protocol and results were obtained after treatment for two hours at 37° C.:

| | Mutano-lysin | Na Citrate pH 5.5 | Na Citrate pH 7.0 | Tide 200 ppm | Endo-H 200 ppm | Results |
|---|---|---|---|---|---|---|
| 1 | Control | | | | | Fimbriae, tight cell wall |
| 2 | 200 ppm | + | | | | Fimbriae, tight cell wall |
| 3 | 200 ppm | | + | | | Fimbriae, tight cell wall |
| 4 | 200 ppm | + | | + | | Fimbriae, tight cell wall |
| 5 | 200 ppm | | + | + | | Fimbriae, cell condensation |
| 6 | 200 ppm | + | | | + | Loss of fimbriae |
| 7 | 200 ppm | | + | | + | Few cells, some ghosts, cell wall disintegration |
| 8 | 200 ppm | + | | + | + | Some fimbriae |
| 9 | 200 ppm | | + | + | + | Cells in bad shape (condensed) but still present |

As can be seen, the gross morphology of the bacteria exposed to Endo-H and mutanolysin either with or without detergent at various pH, was significantly modified. The most dramatic effects occurred at pH 7 when Endo-H was used alone or in combination with detergent. Cell viability, however, was apparently not effected. Endo-H and mutanolysin did not reduce the number of colonies obtained in a plating experiment as compared to a buffer control.

EXAMPLE 21

Bacterial Removal from Glass Surfaces by Endo-H and PNGase F

*Escherichia coli* (ATCC 31617) and *Staphylococcus epidermidis* (ATCC 155) were used to inoculate glass slides. Each slide contained two etched circles and each was inoculated with *E. coli* or *S. epidermidis*.

The bacteria were allowed to incubate at 37° C. for two hours.

After rinsing with distilled water, the slides were treated with either 1) PBS buffer, 2) Endo-H (100 ppm) in PBS buffer, or 3) PNGase F (100 ppm) in PBS buffer. The Endo-H was derived from *E. coli* producing *S. plicatus* Endo-H. After 30 minutes at 37° C. the slides were rinsed in distilled water. After Gram staining, the slides were read with bright field optics on a light microscope.

In the case of the buffer control, the number of bacteria remaining on the slide was greater than 100 per field. The slides treated with Endo-H contained far fewer bacteria. In the case of *S. epidermidis*, only about 1 to 3 bacteria were observed per field. In the case of *E. coli*, about 5 to 10 were observed per field. For those slides treated with PNGase F, moderate numbers of bacteria were observed for both *S. epidermidis* and *E. coli* (approximately 20 per field).

These results indicated that PNGase F is capable of removing bacteria from glass surfaces albeit not as efficiently as Endo-H.

EXAMPLE 22

Tablet Denture Cleaner with Endo-H

Sodium bicarbonate, sodium perborate monohydrate, tartaric acid, sodium tripolyphosphate, sulphamic acid, polyethylene glycol (20,000 m.wt.) and ethylene diamine tetraacetate are separately granulated by fluidizing in a hot air bed at 60°-65° C. for 30 minutes. Such granulates are then tumble mixed with the other ingredients to produce a "first layer" mixture and a "second layer" mixture, wherein the "first layer" mixture has the following composition:

|  | % by Weight |
|---|---|
| Sodium bicarbonate | 30.00 |
| Tartaric acid | 23.00 |
| Potassium monopersulphate | 16.00 |
| Sulphamic acid | 11.00 |
| Oisodium pyrophosphate | 8.20 |
| Sodium carbonate | 3.90 |
| Polyethylene glycol | 12.60 |
| Sodium sulphate | 2.00 |
| Peppermint powder | 2.50 |
| Silicon dioxide | 1.30 |
| Sodium dodecyl benzene sulphonate | 0.50 | and the "second layer" mixture has the following composition:

|  | % by Weight |
|---|---|
| Sodium perborate monohydrate | 30.00 |
| Potassium monopersulphate | 28.00 |
| Sodium bicarbonate | 13.34 |
| Sodium tripolyphosphate | 10.00 |
| Sodium bicarbonate/colour | 4.00 |
| Trilon B | 3.00 |
| Sodium carbonate | 3.00 |
| Polyethylene glycol | 2.50 |
| Silicone dioxide | 2.00 |
| Peppermint powder | 1.50 |
| Wasag ester 7 | 0.70 |
| Wasag ester 15 | 0.70 |
| Hardened triglycerides | 0.50 |
| Sodium dodecyl benzene sulphonate | 0.40 |
| Succinate detergent | 0.30 |
| Blue Lake No. 1 | 0.06 |
| Endo-H | 100 ppm |

A tablet is produced by compressing in a HORN rotary tableting press of 39 stations. Compressing is in two stages: Initially the "second layer", blue mixture is compressed to very low pressure (10 kN per tablet) by way of tamping. The "first layer", white mixture is then instilled and pressed to 70 kN per tablet. In this way a tablet of 4 grams is produced being 2.7 grams blue and 1.3 grams white.

Tablets are dissolved in water by the consumer to clean dentures placed in the water.

EXAMPLE 23

Light Cream with Endo-H

An oil-in-water sunscreen emulsion base is made from the following ingredients, which are indicated by their chemical or Cosmetic, Toiletry and Fragrance Association (CTFA) name:

| Ingredient | Weight % |
|---|---|
| Water Phase: | |
| Methylparaben (preservative) | 0.20 |
| Pantethine (moisturizer) | 0.10 |
| Carbomer 934 (thickener) | 0.08 |
| Sodium hydroxide, 10% (neutralizer) | 1.00 |
| Endo-H | 100 ppm |
| Purified water, q.s. to | 100% |
| Oil Phase: | |
| Heavy mineral oil | 4.00 |
| Stearic acid, double pressed (anionic emulsifier) | 3.00 |
| Cholesterol (auxiliary emulsifier) | 1.00 |
| Cetyl alcohol (auxiliary emulsifier) | 1.80 |
| Castor oil (emollient) | 1.00 |
| Cetyl palmitate (emollient) | 1.20 |
| Octyl dimethyl PABA (U.V.-absorber) | 1.40 |
| Propylparaben (preservative) | 0.10 |

In a mixing vessel equipped with a mechanical stirrer, water and the water phase ingredients other than the sodium hydroxide and Endo-H aqueous solution are added and mixed with heating to about 75°-80° C. to form a uniform aqueous dispersion. The sodium hydroxide solution is then added and mixed into the aqueous phase to neutralize the acidic Carbomer thickener.

In a separate mixing vessel, the mineral oil and oil phase ingredients are added and mixed with heating to about 80°-82° C. to form a uniform oil phase. The heated oil phase is slowly added to the heated water phase using high speed mechanical dispersing means. Mixing is continued until a homogeneous oil/water emulsion is obtained. The emulsion is cooled to room temperature. If desired, optional colorants such as water-soluble dyes are preferably mixed into the emulsion at about 45°-50° C. and fragrant oils are preferably added at about 35°-40° C. Endo-H is mixed into the emulsion at about 35°-40° C.

EXAMPLE 24

Removal of S. aureus from Pig Skin

Pig skin was inoculated with S. aureus ($1.2 \times 10^7$ colonies/ml) by spreading 0.1 cc of the culture on the skin surface. The organisms were allowed to set on the skin for two hours at room temperature. Duplicate pieces of skin were then treated for 30 seconds with:

1) untreated control
2) water alone
3) 10% soap solution
4) #3 + Endo-H (20 ppm)
5) 20 ppm Endo-H in buffer The Endo-H was obtained from E. coli transformed to produce Endo-H from S. plicatus. After treatment the samples were rinsed in distilled water and placed in 2% osmium tetroxide followed by fixation in Ryter-Kellenberger fixative. The samples were then processed alternatively in osmium and thiosemicarbizone. After critical point drying, all samples were examined on the SEM. Photomicrographs were taken.

S. aureus colonies were found in abundance on the untreated, water treated, or plain soap treated samples. See, e.g. FIG. 11 which demonstrates the effect of treatment with liquid hand soap. The Endo-H-treated samples demonstrated a significant loss of organisms. See, e.g. FIG. 12 which demonstrates the removal of S. aureus from swine skin when treated with liquid hand soap plus Endo-H.

EXAMPLE 25

Mold Removal from Shower Curtain

A plastic shower curtain was moistened with tap water and placed in the dark for 3 weeks. At the end of that time, a small sample of the curtain that was covered with mold was treated with:
1) distilled water
2) +2000 ppm Joy detergent
3) +1000 ppm Endo-H
4) untreated The Endo-H was obtained from *E. coli* transformed to produce Endo-H from *S. plicatus*. The treatments lasted 10–15 seconds at room temperature. The shower curtain was wiped off after treatment with a cotton swab.

Figure 13:
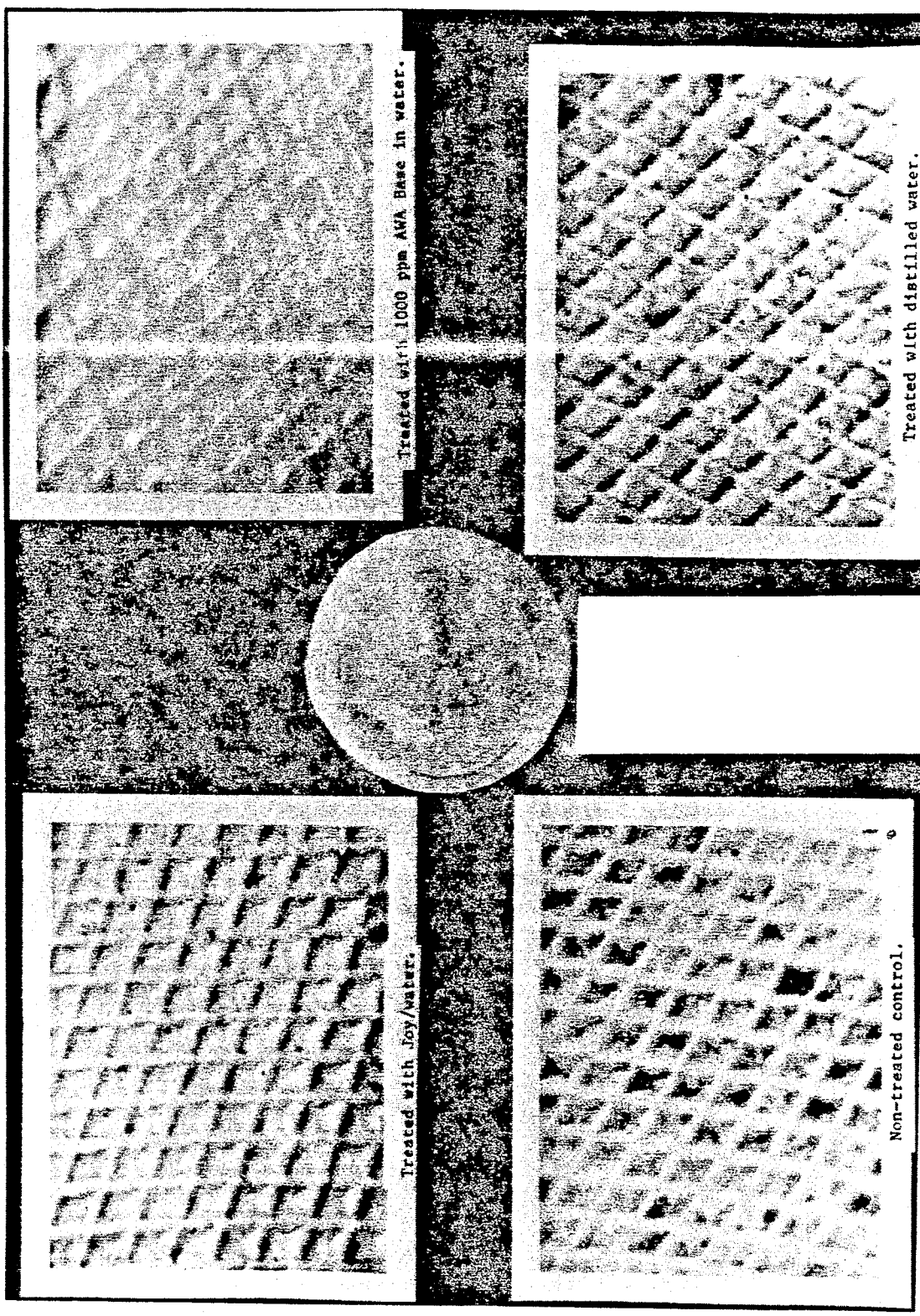
FIG. 13 demonstrates that Endo-H is more effective in removing mold from a shower curtain than water or a detergent composition. The center photograph is of a portion of the shower curtain. The other four photographs are enlargements of the corresponding quadrants of the center photograph.

FIG. 13 depicts the results obtained. The non-treated control (lower right photograph—lower right quadrant of center photograph) showed abundant mold and mildew particles both macro and microscopically.

The distilled water control (upper right photograph—upper right quadrant of center photograph) showed less organisms, although particles still remained and discoloration was evident.

The Joy-treated control (lower left photograph—lower left quadrant of center photograph) showed less organisms than the water treated sample, but discoloration was still evident.

The Endo-H treated sample (upper left photograph—upper left quadrant of center photograph) was free of both organisms and any discolorations.

EXAMPLE 26

Bacterial Removal from Fabric

Fabric swatches were cut to the size of a petri dish. Additional fabric was added to reach a 5% fabric load (which was not inoculated). The swatches were sterilized in an autoclave for 15 minutes at 15 lbs. 121° C. One fabric load is needed for each treatment. Glass beads (40 g) and 100 mls 0.2M pH 7.0 citrate buffer was placed into 250 ml Erlenmeyer flasks. The flasks were plugged with rubber stoppers and aluminum foil and sterilized in an autoclave. *E. coli* subcultured into fresh nutrient broth and allowed to incubate for 48 hours at 37° C. Half strength trypticase soy agar plates (10 g/500 mls) were prepared and sterilized. After cooling, tetrazolium (1 ml/liter) was added.

The agar plates were inoculated as follows:
1) serial dilutions from the 48-hour culture were prepared (1:10, and 10 fold dilutions through three more tubes in peptone water);
2) Thereafter, each swatch was inoculated with 2 mls of the last dilution ($10^4$).
3) The swatches were then incubated at 37° C. for two hours (two swatches/treatment).

Figure 14:
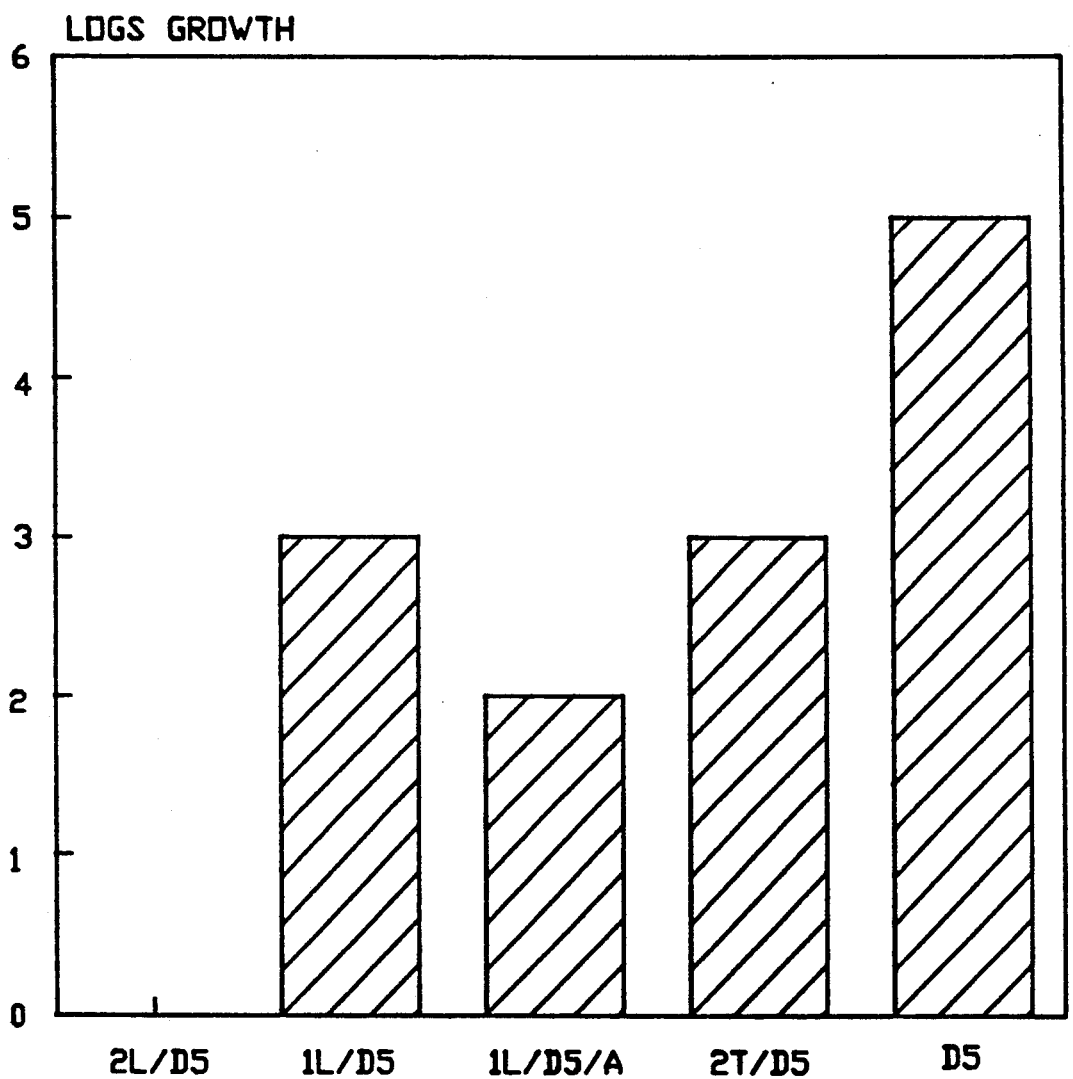
FIG. 14 demonstrates the antimicrobial effect of Endo-H in combination with different antimicrobial agents.

After incubation, the swatches were laundered as follows:

Wash 100 mls sterile 0.2M pH 7.0 citrate buffer+40 g glass beads+the treatment described in FIG. 14 (where AWA is Endo-H from *E. coli* transformed to produce Endo-H from *S. plicatus*) in a 250 ml Erlenmeyer flask (sterile). Two inoculated swatches+sterile fabric to make 5% fabric load were washed at 95° F. for 12 minutes with shaking.

Rinse

After washing, the swatches were rinsed by adding 100 mls sterile doubly distilled/deionized water+40 g glass beads in a 250 ml Erlenmeyer flask (sterile) at room temperature for two minutes with shaking.

The fabric swatches were then placed in petri dishes and overlaid with 3 mls of one-half strength trypticase soy agar with tetrazolium. After incubation for 48 hours, the colonies were counted.

The results are shown in FIG. 15. These results indicate that 2% Irgasan plus Liquid Tide provide a two log decrease in bacterial growth as compared to Tide alone. The addition of 40 ppm Endo-H, however, reduces bacterial growth another log unit.

EXAMPLE 27

Effect of Endo-H on Yeast

Broth cultures (18 hour) of *Candida albicans* and *Sacchromyces cerevisiae* were treated with:
1) 0.2M Na citrate buffer, pH 5.5
2) #1 plus 200 ppm Endo-H (from *E. coli* producing *S. plicatus* Endo-H)

The treatments lasted 2 hours at 37° C.

After treatment, an aliquot of each was placed on a formvar-coated 200 mesh copper grid, and examined by TEM. Photomicrographs of the examinations were taken and are presented in FIGS. 15 and 16.

Figure 15A:
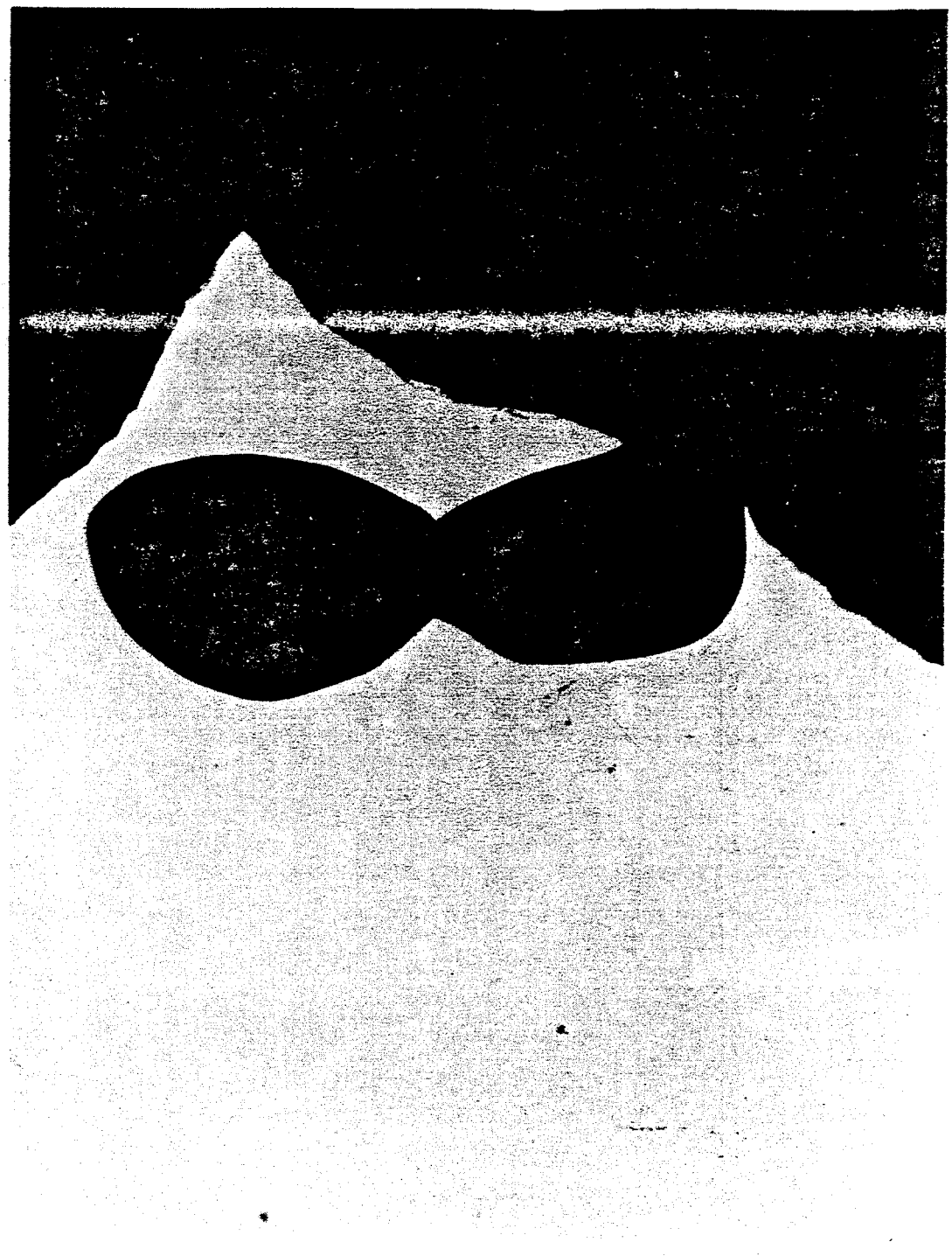
FIGS. 15A-B and 16A-B demonstrate the effect of Endo-H on different species of yeast.
Figure 15B:
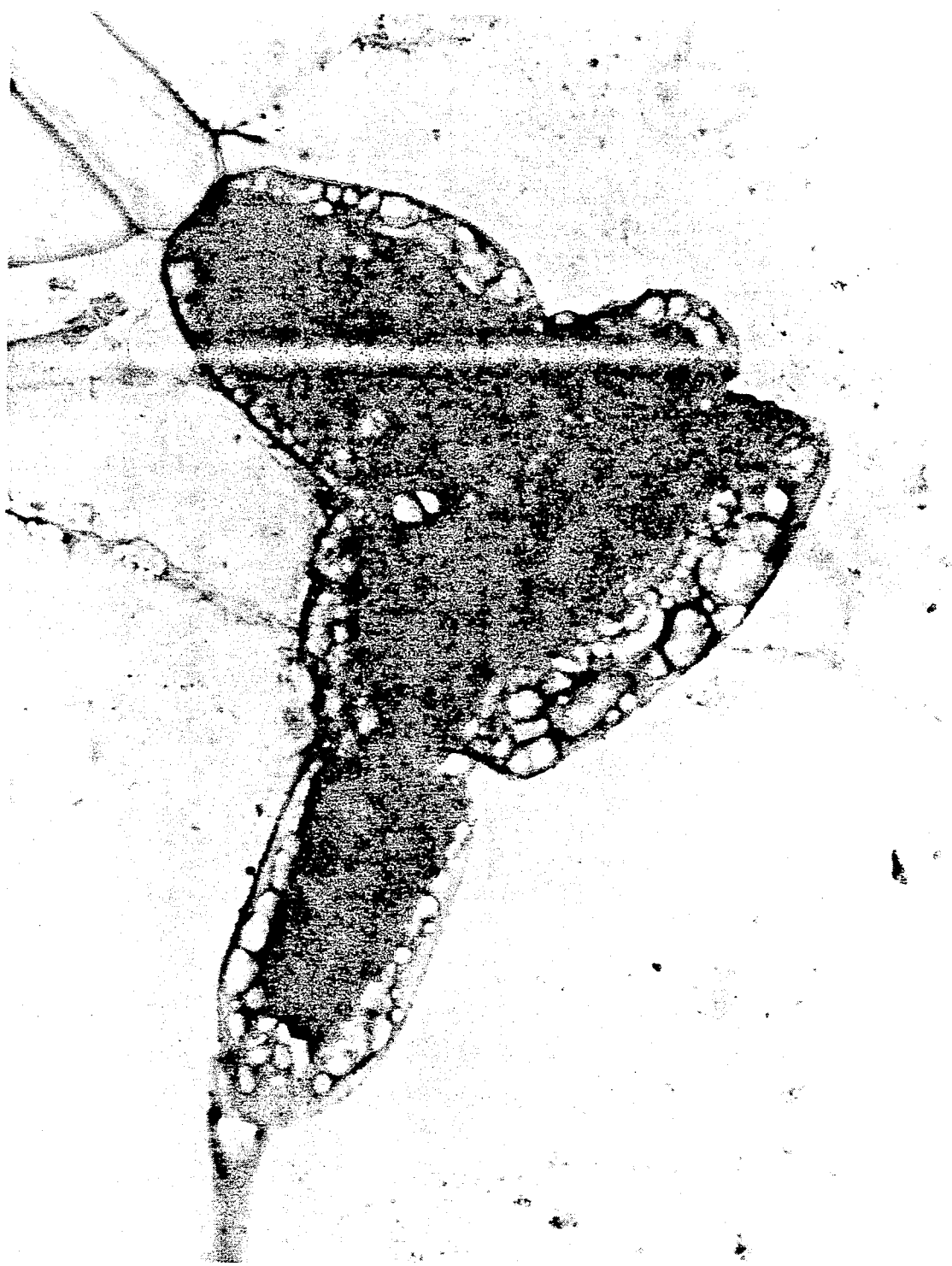

As can be seen in FIG. 15A, Candida treated with buffer alone was in good morphological condition. As indicated in FIG. 15B, Candida treated with Endo-H leaked material at a rapid rate and lost structural integrity.

Figure 16A:
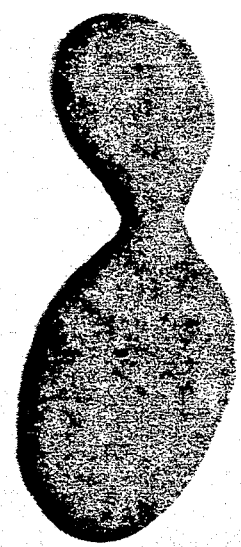
Figure 16B:
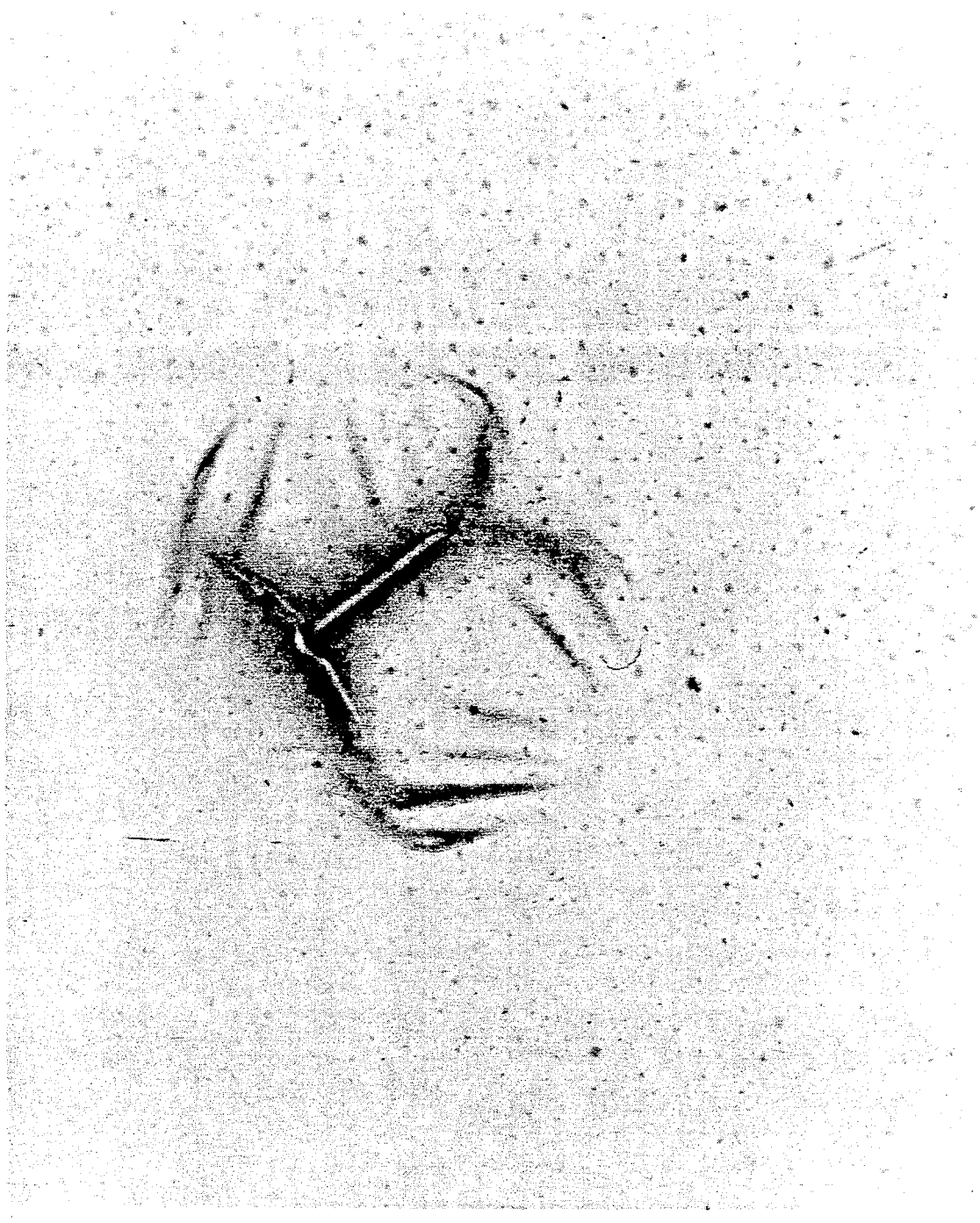

Sacchromyces treated with buffer alone was in good morphological condition as can be seen in FIG. 16A. When treated with Endo-H, however, all that remained were very limited pieces of membranous material. See FIG. 16B.

EXAMPLE 28

Effect of Endo-H and Lysozyme on Viability of *E. coli*

A culture of *E. coli* K12 grown overnight in Laurie Broth (LB), was diluted 1:1000 in LB and regrown for 4 hours at 37° C. Cells were centrifuged, washed and resuspended in 0-1M NA-acetate pH 5.5 (NA) buffer. Eight tubes were set up as follows:

| Tube Number | 1,2 | 3,4 | 5,6 | 7,8 |
| --- | --- | --- | --- | --- |
| μl cells | 800 | 800 | 800 | 800 |
| μl NA buffer | 200 | — | — | 200 |
| μl Endo-H (1 mg/ml) | — | 200 | 200 | — |

The Endo-H was from *B. subtilis* transformed to produce Endo-H from *S. plicatus*. Tubes were incubated for one hour at 37° C. Tubes were centrifuged, washed and resuspended in 8.00 μl of 0.1M Na-phosphate, pH 7.2 (NP) buffer containing 0.1M EDTA. Buffer or hen egg white lysozyme solution was added to tubes as follows:

| Tube Number | 1,2 | 34, | 56, | 7,8 |
| --- | --- | --- | --- | --- |
| μl NP buffer | 200 | 200 | | |
| μl lysozyme (1 mg/ml) | — | — | 200 | 200 |

Aliquots were taken at this time to determine colony forming units (CFU) (Column A). After incubation for one hour at 37° C. aliquots were used to determine CFUs (Column B). The log of colony forming units were calculated. The decrease in log CFUs was determined by subtracting B from A. The results are shown below:

| Condition | Log CFUs A | Log CFUs B | Change in log CFUs |
|---|---|---|---|
| Control | 7.89 | 7.90 | +0.01 |
| Endo-H (200 ppm) | 8.21 | 7.92 | −0.29 |
| Lysozyme (200 ppm) | 7.87 | 7.68 | −0.19 |
| Endo-H + lysozyme | 8.17 | 7.53 | −0.64 |

These results indicate that the combination of Endo-H and lysozyme decreases the viability of *E. coli* as compared to Endo-H or lysozyme alone.

EXAMPLE 29

Comparison of Endo-H with T-4 or Hen Egg White Lysozyme on Viability of *E. coli*

*E. coli* cells were washed and suspended in 0.1M Na-acetate pH 5.5 buffer. Cells were aliquoted (10 ml) in two tubes. To one tube, only buffer was added (control) and to another Endo-H was added (treated). The Endo-H was from *B. subtilis* transformed to produce Endo-H from *S. plicatus*. Cells were incubated for one hour at 37° C. Cells were centrifuged, washed and resuspended in 0.1M Na-phosphate (pH 7.2) buffer. Cells were aliquoted equally and incubated either with buffer or lysozyme. Hen egg white (HL) and T4 (TL) lysozymes were compared in this experiment. Tubes were incubated for 1.5 hours. Samples were diluted and plated for CFU determination before (A) and after (B) incubation. The log of CFUs were determined. The following results were obtained.

| Incubation Condition First | Incubation Condition Second | Log CFUs A | Log CFUs B | Change in log CFUs |
|---|---|---|---|---|
| Endo-H (300 ppm) | — | 7.60 | 7.23 | −0.37 |
| — | HEWL (445 ppm) | 6.69 | 6.73 | −0.23 |
| Endo-H (300 ppm) | HEWL (445 ppm) | 7.41 | 6.81 | −0.60 |
| — | TL (445 ppm) | 4.98 | 4.53 | −0.45 |
| Endo-H (300 ppm) | TL (445 ppm) | 5.27 | 4.30 | −0.93 |

These results indicate that T-4 lysozyme is also effective in reducing the viability of *E. coli* in combination with Endo-H.

EXAMPLE 30

Treatment of Soiled Diaper Material with Endo-H

Samples were obtained from a soiled diaper. Each sample was divided. The left side of the sample was washed in 2000 ppm Tide and 1 ppm BPN' (subtilisin protease from *Bacillus amyloliquifaciens*). The right side was washed in 2000 ppm Tide, 1 ppm BPN' and 40 ppm Endo-H (Boehringer Mannheim Biochemical Catalog No. 100 119). Each sample was washed for 12 minutes at 95° F. The results of two experiments are shown in FIGS. 17 and 18. As can be seen, the diaper material on the right side of FIGS. 17 and 18 contains substantially less fecal stain as compared to the Tide-protease treated diaper shown on the left of FIGS. 17 and 18.

Having described the preferred embodiments of the present invention, it will appear to those of ordinary skill in the art that various modifications may be made and that such modifications are intended to be within the scope of the present invention. Other compositions of the present invention are obtained when Endo-D or F or PNGase F are substituted for Endo-H in the Examples.

All references cited herein are expressly incorporated by reference.

What is claimed is:

1. A method for releasing at least a portion of a glycoside-containing substance from a surface to which said glycoside-containing substance is bound, said glycoside-containing substance comprising at least one glycosidic linkage, said method consisting of:
    contacting said substance bound to said surface with a Type II endoglycosidase in an amount sufficient to cleave one or more of said glycosidic linkages; and
    releasing at least a portion of said bound substance.

2. A method of claim 1 wherein the glycoside-containing substance is selected from the group consisting of: blood or components thereof, fecal matter or components thereof and microorganisms.

3. A method of claim 1 wherein said Type II endoglycosidase is selected from the group consisting of Endo-β-N-acetylglucosaminidase, Endo-α-N-acetylgalactosaminidase and Endo-β-N-galactosidase.

4. A method of claim 3 wherein the Type II endoglycosidase is selected from the group consisting of: Endo-D, Endo-H, Endo-L, Endo-CI, Endo-CII, Endo-F-Gal type, Endo-F and PNGaseF.

5. A method of claim 1 wherein said surface is selected from the group consisting of: fabric, biological tissue, tooth enamel, contact lens, glass, ceramic, metal, metal alloy, plastic, plant, fruit and vegetable.

6. A method of claim 2 wherein said surface is selected from the group consisting of: fabric, biological tissue, tooth enamel, contact lens, glass, ceramic, metal, metal alloy, plastic, plant, fruit and vegetable.

7. A method of claim 1 further comprising contacting said glycoside-containing substance with a fluid comprising a detergent other than SDS, to remove said released portion from said surface in said fluid.

8. A method of claim 1 further comprising contacting the portion of said substance released from said surface, with a washing solution to remove said portion from said surface in said washing solution.

9. A method of claim 1 further comprising contacting said substance with a disulfide cleaving reagent.

10. A method of claim 1 further comprising contacting said substance with a surfactant.

11. A method for cleaning a surface on which is bound a glycoside-containing substance, said glycoside-containing substance comprising at least one glycosidic linkage, said method consisting of:
    contacting said glycoside-containing substance or the surface to which it is bound with a Type II endoglycosidase in an amount sufficient to cleave said glycosidic linkage; and
    releasing at least a portion of said substance from said surface.

12. A method of claim 11 wherein said surface is selected from the group consisting of: fabric, biological tissue, tooth enamel, contact lens, glass, ceramic, metal, metal alloy, plastic, plant, fruit and vegetable.

13. A method of claim 11 wherein the glycoside-containing substance is selected from the group consisting of: blood or components thereof, fecal matter or components thereof and microorganisms.

14. A method of claim 12 wherein the glycoside-containing substance is selected from the group consisting of: blood or components thereof, fecal matter or components thereof and microorganisms.

15. A method of claim 11 wherein said the Type II endoglycosidase is selected from the group consisting of Endo-$\beta$-N-acetylglucosaminidase, Endo-$\alpha$-N-acetylgalactosaminidase and Endo-$\beta$-N-galactosidase.

16. A method of claim 15 wherein the Type II endoglycosidase is selected from the group consisting of: Endo-D, Endo-H, Endo-L, Endo-CI, Endo-CII, Endo-F-Gal type, Endo-F and PNGaseF.

17. A method of claim 11 further comprising contacting said glycoside-containing substance with a fluid comprising a detergent other than SDS, to remove said released portion from said surface in said fluid.

18. A method of claim 11 further comprising contacting the portion of said substance released from said surface, with a washing solution to remove said portion from said surface in said washing solution.

19. A method of claim 11 further comprising contacting said substance with a disulfide cleaving reagent.

20. A method of claim 11 further comprising contacting said substance with a surfactant.

21. A method of claim 11 wherein the glycoside-containing substance is blood, feces or a microorganism, or a component thereof, and the surface is fabric.

* * * * *